(12) United States Patent
Adam et al.

(10) Patent No.: US 6,548,495 B2
(45) Date of Patent: Apr. 15, 2003

(54) DIHYDRO-BENZO [B] [1,4] DIAZEPIN-2-ONE DERIVATIVES

(75) Inventors: Geo Adam, Schopfheim (DE); Erwin Goetschi, Reinach (CH); Vincent Mutel, Brunstatt (FR); Juergen Wichmann, Steinen (DE); Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/116,597

(22) Filed: Apr. 3, 2002

(65) Prior Publication Data

US 2002/0198197 A1 Dec. 26, 2002

(51) Int. Cl.$^7$ .................. C07D 243/12; C07D 409/04; C07D 405/04; C07D 471/04; A61K 31/55
(52) U.S. Cl. ........................................ 514/221; 540/517
(58) Field of Search ........................... 514/221; 540/517

(56) References Cited

U.S. PATENT DOCUMENTS 6,407,094 B1 * 6/2002 Adam et al. ................. 514/221

FOREIGN PATENT DOCUMENTS

| WO | WO 01/10846 | 2/2001 |
| WO | WO 01/29011 | 4/2001 |
| WO | WO 01/29012 | 4/2001 |

OTHER PUBLICATIONS

Bellamy et al., *Tetrahedron Letters*, vol. 25, No. 8, pp. 839–842 (1984).
Achmatowicz et al., *Tetrahedron Lett.*, vol. 27, pp. 1973–1996 (1971).
Boyer et al., *J. Heterocyclic Chem.*, vol. 25, pp. 1003–1005 (1988).
Ohmori et al., *J. Med. Chem.*, vol. 37, pp. 467–475 (1945).
Ishikawa et al., *J. Med. Chem.*, vol. 28, pp. 1387–1393 (1985).
Fanta et al., *Organic Syntheses*, vol. 25, pp. 78–80 (1945).
Corey et al., *J. Org. Chem.*, vol. 38, No. 18, pp. 3224 (1973).
Eicher et al., *Synthesis*, pp. 755–762 (1996).
Widmer, *Synthesis* pp. 135–136 (1983).
Bowman et al., *Org. Prep. Proc. Int.*, vol. 22, No. 5, pp. 636–638 (1990).
Quallich et al., *Synthesis* pp. 51–53 (1993).

* cited by examiner

*Primary Examiner*—Bruck Kifle
(74) *Attorney, Agent, or Firm*—George W. Johnston; Patricia S. Rocha-Tramaloni

(57) ABSTRACT

This invention is a dihydro-benzo[b][1,4]diazepin-2-one derivative of the formula

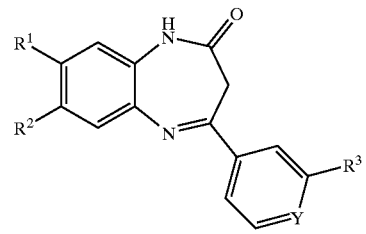

wherein $R^1$, $R^2$, $R^3$ and Y are as defined in the specification. The invention includes pharmaceutical compositions containing these compounds, a process for their preparation and a method of treatment or prevention of acute and/or chronic neurological disorders by administering an effective amount of the compound of formula I or a pharmaceuticall acceptable salt thereof.

24 Claims, No Drawings

DIHYDRO-BENZO [B] [1,4] DIAZEPIN-2-ONE DERIVATIVES

BACKGROUND

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

SUMMARY

The present invention is a compound of formula I

I wherein
R is selected from the group consisting of cyano,
   fluoro-lower alkyl,
   lower alkoxy,
   fluoro-lower alkoxy,
   unsubstituted pyrrol-1-yl, and pyrrol-1-yl substitued by one to three substituents selected from the group consisting of
      fluoro, chloro, cyano, unsubstituted phenyl or phenyl substituted by halogen,
      —(CH$_2$)$_{1-4}$-hydroxy, fluoro-lower alkyl, lower alkyl,
      —(CH$_2$)$_n$-lower alkoxy,
      —(CH$_2$)$_n$—C(O)O—R", —(CH$_2$)$_{1-4}$—NR'R",
      hydroxy-lower alkoxy and
      —(CH$_2$)$_n$—CONR'R";

$R^2$ is selected from the group consisting of
   halogen,
   hydroxy,
   lower alkyl,
   fluoro-lower alkyl,
   lower alkoxy,
   hydroxymethyl,
   hydroxyethoxy,
   lower alkoxy-(ethoxy)$_m$, wherein m=1 to 4,
   lower alkoxymethyl,
   cyanomethoxy,
   morpholine-4-yl,
   thiomorpholine-4-yl,
   1-oxothiomorpholine-4-yl,
   1,1-dioxothiomorpholine-4-yl,
   4-oxo-piperidine-1-yl
   4-alkoxy-piperidine-1-yl,
   4-hydroxy-piperidine-1-yl,
   4-hydroxyethoxy-piperidine-1-yl,
   4-lower alkyl-piperazine-1-yl,
   alkoxycarbonyl,
   2-dialkylamino-ethylsulfanyl,
   N,N-bis lower alkylamino lower alkyl,
   carbamoylmethyl,
   alkylsulfonyl
   lower alkoxycarbonyl-lower alkyl,
   alkylcarboxy-lower alkyl,
   carboxy-lower alkyl,
   alkoxycarbonylmethylsulfanyl,
   carboxymethylsulfanyl,
   1,4-dioxa-8-aza-spiro[4.5]dec-8-yl,
   carboxy-lower alkoxy,
   cyano-lower alkyl,
   2,3-dihydroxy-lower alkoxy,
   carbamoylmethoxy,
   2-oxo-[1,3]-dioxolan-4-yl-lower alkoxy,
   N-(2-hydroxy-lower alkyl)-N-lower alkyl amino,
   hydroxycarbamoyl-lower alkoxy,
   2,2-dimethyl-tetrahydro-[1,3]dioxolo[4,5c]-pyrrol-5-yl,
   lower alkoxy-carbamoyl-lower alkoxy,
   3R-hydroxy-pyrrolidin-1-yl,
   3,4-dihydroxy-pyrrolidin-1-yl,
   2-oxo-oxazolidin-3-yl,
   lower alkyl-carbamoylmethoxy,
   aminocarbamoyl-lower alkoxy, and, when $R_1$ is unsubstituted pyrrol-1-yl or pyrrol-1-yl substituted as described above, hydrogen;

Y is —CH= or =N—;

$R^3$ is selected from the group consisting of halogen,
   lower alkyl,
   fluoro-lower alkyl,
   lower alkoxy,
   cyano,
   —(CH$_2$)$_n$—C(O)—OR",
   (CH$_2$)$_n$—C(O)—NR'R",
an unsubstituted five-membered aromatic heterocycle and a five-membered aromatic hetero cycle substituted by halogen fluoro-lower alkyl, fluoro-lower alkoxy, cyano, —(CH$_2$)$_n$—NR'R", —(CH$_2$)$_n$—C(O)—OR",
—(CH$_2$)$_n$—C(O)—NR'R", —(CH$_2$)$_n$—SO$_2$—NR'R",
—(CH$_2$)$_n$—C(NH$_2$)=NR", hydroxy, lower alkoxy, lower alkylthio, unsubstituted lower alkyl, or lower alkyl substituted by fluoro, hydroxy, lower alkoxy, cyano or carbamoyloxy;

R' is selected from the group consisting of hydrogen,
  lower alkyl,
  C$_3$–C$_6$-cycloalkyl,
  fluoro-lower alkyl and
  2-lower alkoxy lower alkyl;

R" is selected from the group consisting of hydrogen,
  lower alkyl,
  C$_3$–C$_6$-cycloalkyl,
  fluoro-lower alkyl,
  2-lower alkoxy lower alkyl,
  —(CH$_2$)$_{2-4}$-di-lower alkylamino,
  —(CH$_2$)$_{2-4}$-morpholinyl,
  —(CH$_2$)$_{2-4}$-pyrrolidinyl,
  —(CH$_2$)$_{2-4}$-piperidinyl or
  3-hydroxy-lower alkyl;

n is 0, 1, 2, 3 or 4;

or a pharmaceutically acceptable addition salt thereof.

It has surprisingly been found that the compounds of formula I are metabotropic glutamate receptor antagonists. Compounds of formula I are distinguished by valuable therapeutic properties.

The compounds of formula I can also be used in form of their prodrugs. Examples are esters, N-oxides, phosphate esters, glycoamide esters, glyceride conjugates and the like. The prodrugs may add to the value of the present compounds advantages in absorption, pharmacokinetics in distribution and transport to the brain.

As compounds of the present invention are metabotropic glutamate receptor agonists, they can be used to treat or prevent acute and/or chronic neurological disorders responsive to a metabotropic glutamate receptor agonist in a method of treatment comprising administering a therapeutically effective amount of a compound of formula I or a pharmaceutically acceptable salt thereof to a patient in need of such treatment.

All tautomeric forms of the compounds of the invention are within the scope of the invention.

DETAILED DESCRIPTION

A preferred compound of the invention of formula I is the compound, wherein R$^1$ is trifluoromethyl. An exemplary preferred compound, wherein R$^2$ is morpholine, is selected from the group consisting of 4-(8-morpholin-4-yl-4-oxo-7-trifluoromethyl-4,5-dihydro-3H-benzo[b][1,4]diazepin-2-yl)-pyridine-2-carbonitrile, 4-[3-(3-methyl-isoxazol-5-yl)-phenyl]-7-morpholin-4-yl-8-trifluoromethyl-1,3-dihydro-benzo[b][1,4]diazepin-2-one, 4-[3-(2-methyl-2H-pyrazol-3-yl)-phenyl]-7-morpholin-4-yl-8-trifluoromethyl-1,3-dihydro-benzo[b][1,4]diazepin-2-one, 4-[3-(3-hydroxymethyl-isoxazol-5-yl)-phenyl]-7-morpholin-4-yl-8-trifluoromethyl-1,3-dihydro-benzo[b][1,4]diazepin-2-one, and 4-[3-(5-hydroxymethyl-isoxazol-3-yl)-phenyl]-7-morpholin-4-yl-8-trifluoromethyl-1,3-dihydro-benzo[b][1,4]diazepin-2-one.

Also preferred is a compound of formula I, wherein R$^1$ is trifluoromethyl and R$^2$ is thiomorpholine selected from the group consisting of 4-[3-(3-methyl-isoxazol-5-yl)-phenyl]-7-thiomorpholin-4-yl-8-trifluoromethyl-1,3-dihydro-benzo[b][1,4]diazepin-2-one, and 4-(4-oxo-8-thiomorpholin-4-yl-7-trifluoromethyl-4,5-dihydro-3H-benzo[b][1,4]diazepin-2-yl)-pyridine-2-carbonitrile.

A further preferred compound of formula I wherein R$^1$ is trifluoromethyl and R$^2$ is lower alkoxy is selected from the group consisting of 7-methoxy-4-[3-(3-methyl-isoxazol-5-yl)-phenyl]-8-trifluoromethyl-1,3-dihydro-benzo[b][1,4]diazepin-2-one, 7-methoxy-4-[3-(5-pyrrolidin-1-ylmethyl-[1,2,3]triazol-1-yl)-phenyl]-8-trifluoromethyl-1,3-dihydro-benzo[b][1,4]diazepin-2-one, 4-(8-ethoxy-4-oxo-7-trifluoromethyl-4,5-dihydro-3H-benzo[b][1,4]diazepin-2-yl)-pyridine-2-carbonitrile, 4-[3-(5-cyclopropylaminomethyl-[1,2,3]triazol-1-yl)-phenyl]-7-ethoxy-8-trifluoromethyl-1,3-dihydro-benzo[b][1,4]diazepin-2-one, 7-ethoxy-4-(3-{5-[(2,2,2-trifluoro-ethylamino)-methyl]-[1,2,3]triazol-1-yl}-phenyl)-8-trifluoromethyl-1,3-dihydro-benzo[b][1,4]diazepin-2-one, 7-ethoxy-4-(3-[1,2,3]triazol-1-yl-phenyl)-8-trifluoromethyl-1,3-dihydro-benzo[b][1,4]diazepin-2-one, and 7-methoxy-4-(3-[1,2,3]triazol-1-yl-phenyl)-8-trifluoromethyl-1,3-dihydro-benzo[b][1,4]diazepin-2-one.

Another preferred compound of formula I, wherein R$^1$ is trifluoromethyl and R$^2$ is lower alkyl or halogen is selected from the group consisting of 4-(8-methyl-4-oxo-7-trifluoromethyl-4,5-dihydro-3H-benzo[b][1,4]diazepin-2-yl)-pyridine-2-carbonitrile, 7-chloro-4-[3-(3-methyl-isoxazol-5-yl)-phenyl]-8-trifluoromethyl-1,3-dihydro-benzo[b][1,4]diazepin-2-one, 7-chloro-4-[3-(5-cyclopropylaminomethyl-[1,2,3]triazol-1-yl)-phenyl]-8-trifluoromethyl-1,3-dihydro-benzo[b][1,4]diazepin-2-one, 4-[3-(5-cyclopropylaminomethyl-[1,2,3]triazol-1-yl)-phenyl]-7-methyl-8-trifluoromethyl-1,3-dihydro-benzo[b][1,4]diazepin-2-one, 7-methyl-4-[3-(3-methyl-isoxazol-5-yl)-phenyl]-8-trifluoromethyl-1,3-dihydro-benzo[b][1,4]diazepin-2-one, 7-chloro-4-(3-[1,2,4]triazol-1-yl-phenyl)-8-trifluoromethyl-1,3-dihydro-benzo[b][1,4]diazepin-2-one, 7-chloro-4-(3-imidazol-1-yl-phenyl)-8-trifluoromethyl-1,3-dihydro-benzo[b][1,4]diazepin-2-one, 7-chloro-4-(3-[1,2,3]triazol-1-yl-phenyl)-8-trifluoromethyl-1,3-dihydro-benzo[b][1,4]diazepin-2-one, 7-methyl-4-(3-[1,2,4]triazol-1-yl-phenyl)-8-trifluoromethyl-1,3-dihydro-benzo[b][1,4]diazepin-2-one, 4-(3-imidazol-1-yl-phenyl)-7-methyl-8-trifluoromethyl-1,3-dihydro-benzo[b][1,4]diazepin-2-one, 7-methyl-4-(3-[1,2,3]triazol-1-yl-phenyl)-8-trifluoromethyl-1,3-dihydro-benzo[b][1,4]diazepin-2-one, 4-[3-(2-hydroxymethyl-5-methyl-thiazol-4-yl)-phenyl]-7-methyl-8-trifluoromethyl-1,3-dihydro-benzo[b][1,4]diazepin-2-one, and 4-[3-(4-hydroxymethyl-thiazol-2-yl)-phenyl]-7-methyl-8-trifluoromethyl-1,3-dihydro-benzo[b][1,4]diazepin-2-one.

A further preferred compound of formula I, wherein $R^1$ is unsubstituted pyrrol-1-yl and wherein $R^2$ is hydrogen, halogen, lower alkoxy-ethoxy or lower alkoxy, is selected from the group consisting of 4-(3-iodo-phenyl)-8-pyrrol-1-yl-1,3-dihydro-benzo[b][1,4]diazepin-2-one, 4-(3-imidazol-1-yl-phenyl)-8-pyrrol-1-yl-1,3-dihydro-benzo[b][1,4]diazepin-2-one, 4-[3-(4-hydroxymethyl-thiazol-2-yl)-phenyl]-8-pyrrol-1-yl-1,3-dihydro-benzo[b][1,4]diazepin-2-one, 8-pyrrol-1-yl-4-(3-[1,2,3]triazol-1-yl-phenyl)-1,3-dihydro-benzo[b][1,4]diazepin-2-one, 4-(3-oxazol-2-yl-phenyl)-8-pyrrol-1-yl-1,3-dihydro-benzo[b][1,4]diazepin-2-one, 5-[3-(4-oxo-7-pyrrol-1-yl-4,5-dihydro-3H-benzo[b][1,4]diazepin-2-yl)-phenyl]-oxazole-4-carboxylic acid ethyl ester, 4-[3-(4-hydroxymethyl-oxazol-2-yl)-phenyl]-8-pyrrol-1-yl-1,3-dihydro-benzo[b][1,4]diazepin-2-one, and 4-[3-(3-methyl-isoxazol-5-yl)-phenyl]-8-pyrrol-1-yl-1,3-dihydro-benzo[b][1,4]diazepin-2-one.

Further preferred is a compound of formula I, wherein $R^1$ is substituted pyrrol-1-yl and wherein $R^2$ is hydrogen or lower alkoxy selected from the group consisting of 4-(2-chloro-phenyl)-1-[2-(3-cyano-phenyl)-4-oxo-4,5-dihydro-3H-benzo[b][1,4]diazepin-7-yl]-1H-pyrrole-3-carbonitrile, 3-[4-oxo-7-(3-phenyl-pyrrol-1-yl)-4,5-dihydro-3H-benzo[b][1,4]diazepin-2-yl]-benzonitrile, and 3-[7-(2-tert.-butyl-pyrrol-1-yl)-8-methoxy-4-oxo-4,5-dihydro-3H-benzo[b][1,4]diazepin-2-yl]-benzonitrile.

Further preferred is a compound of formula 1, wherein $R^1$ is cyano.

Yet another preferred compound of formula 1, is wherein $R^2$ is morpholine or thiomorpholine. Preferred compounds of formula I in the scope of the present invention are further those, wherein $R^3$ is cyano, an unsubstsituted five-membered aromatic heterocycle or a five-membered aromatic heterocycle substituted by —CH$_2$OH.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" embraces fluorine, chlorine, bromine and iodine.

The term "fluoro-lower alkyl" means a lower alkyl residue, wherein one or more hydrogen-atoms may be replaced by fluoro.

The term "fluoro-lower alkoxy" denotes a lower alkoxy residue in the sense of the definition herein before, wherein one or more hydrogen-atoms is replaced by fluoro.

"Lower alkoxy-(ethoxy)$_m$" (m is 1, 2, 3 or 4) denotes a lower alkoxy residue in the sense of the foregoing definition bound via 1 to 4 —CH$_2$—CH$_2$—O— groups, for example 2-methoxy-ethoxy.

The term "C$_3$–C$_6$-cycloalkyl" means a cycloalkyl group containing 3 to 6 carbon atoms, such as cyclopropyl, cyclobutyl, cyclopentyl or cyclohexyl.

The term "alkylthio" denotes a lower alkyl residue in the sense of the foregoing definition bound via an sulfur atom, for example methylsulfanyl.

The expression "five-membered aromatic heterocycle" embraces furane, thiophene, thiazole, pyrrole, imidazole, pyrazole, oxazole, isoxazole, triazole, oxadiazole, thiadiazole and tetrazole. Preferred aromatic heterocycles are 1,2,3-triazole, isoxazole, 1,3-oxazole, 1,3-thiazole, 1,3,4-oxadiazole or imidazole.

"Substituted" means that a group is substituted with at least one, preferably one or two substituents independently selected from the specified group. The term "unsubstituted" in this document is consistent with the generally accepted usage of this term.

The term "pharmaceutically acceptable addition salt" refers to any salt derived from a pharmaceutically acceptable inorganic or organic acid or base.

The compounds of formula I or a pharmaceutically acceptable salt thereof can be manufactured according to methods, which process comprises reacting a compound of formula II

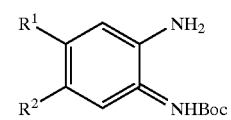

with a compound of formula IV or IVa

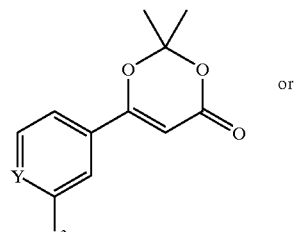

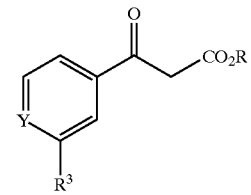

wherein R is lower alkyl, prefereably ethyl or tert.-butyl, thereby forming a compound of formula III

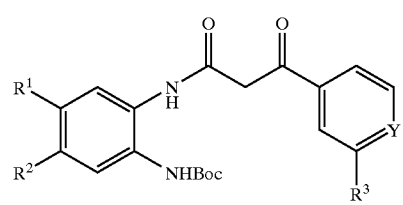

Deprotecting the amino group of the compound of formula III and cyclizing, forming a compound of formula I

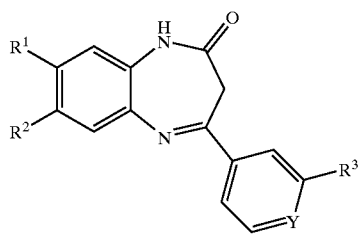

wherein R¹, R², R³ and Y are as described above, or reacting a compound of formula VI

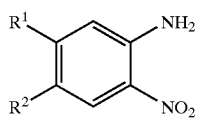

with a compound of formula IV

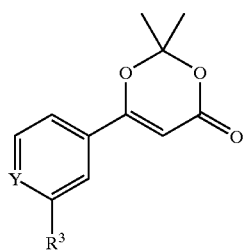

forming a compound of formula V

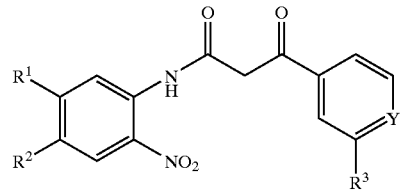

reducing the nitro group and cyclizing, thereby forming a compound of formula I

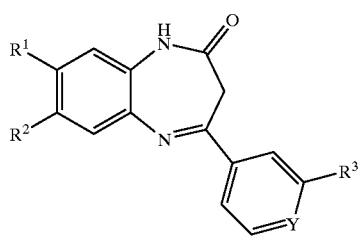

wherein R¹, R², R³ and Y are as described above and, if desired, converting the compound obtained into a pharmaceutically acceptable acid addition salt.

Scheme A

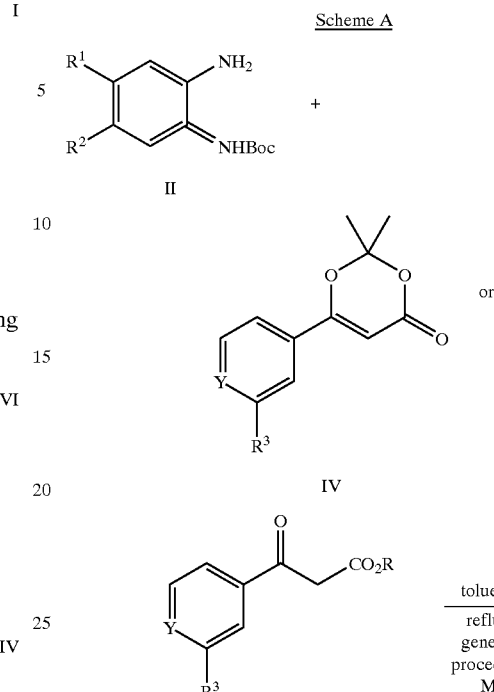

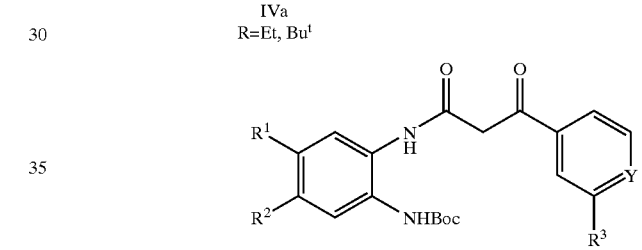

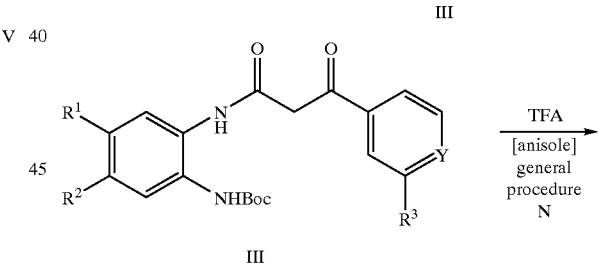

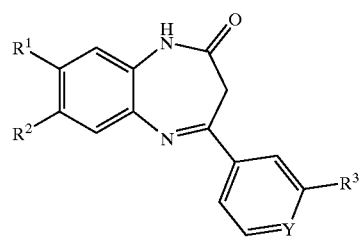

According to scheme A, compounds of formula I, in which Y, R¹, R² and R³ are as described above, can be prepared from compounds of formula II via an acylation-deprotection-cyclization sequence:

For example reacting compounds of formula II with a dioxinone IV, in which Y and R³ are as described above, in an inert solvent such as toluene or xylene at elevated temperatures, preferably between 80° C. and 160° C. gives rise to compounds of formula III.

Alternatively, compounds of formula III can also be prepared by for example reaction of a compound of formula II with a β-ketoester (formula IVa), in which Y and R³ are as described above using the same conditions as described for the reaction with the dioxinones.

Afterwards, cleaving the BOC protecting group in compounds of formula III and concomitant cyclization of the deprotected compound yields the desired compounds of formula I. Any other suitable amino protecting group, such as e.g. Fmoc or benzyloxycarbonyl (Z), can be alternatively used instead of the BOC group.

The deprotection-cyclization step can be carried out by treating the compounds of formula III with for example a Bronsted acid such as trifluoroacetic acid (TFA) in an inert solvent such as dichloromethane (DCM). The reaction is preferably carried out at temperatures between 0° C. and 50° C. It may be advantageous to use also anisole or 1,3-dimethoxybenzene as a carbocation scavenger in the reaction mixture.

Scheme B

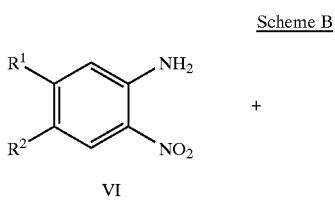

VI

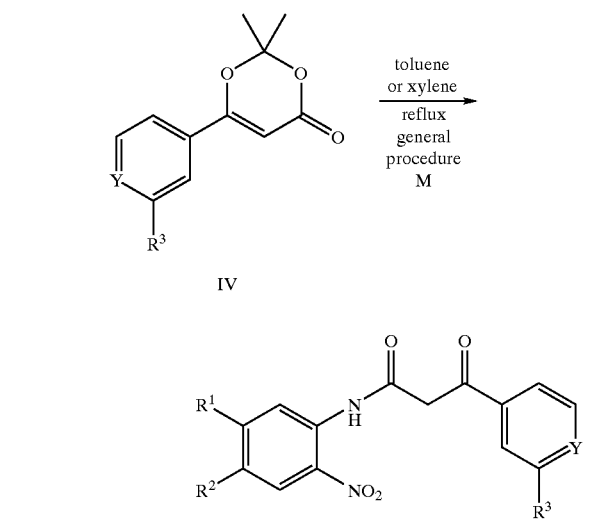

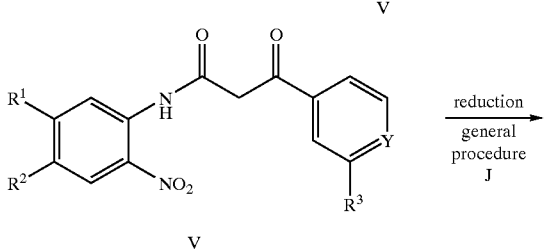

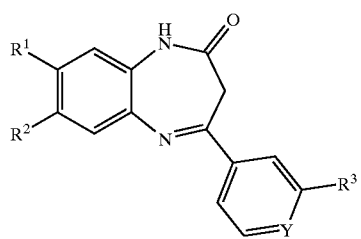

I

In addition, compounds of formula I, in which Y, R¹, R² and R³ are as described above, can be prepared according to scheme B, by for example reducing the nitro group in compounds of formula V to the amino group and subsequent heating of the reaction mixture to achieve the cyclization. The reduction can for example be carried out using hydrogen gas in presence of a suitable catalyst like for example Raney-Nickel. Other possible reduction methods are using tin(II)chloride (SnCl₂·2H₂O) in ethanol at temperatures between 70° C. and 80° C., iron-powder and acetic acid in mixtures of THF, water and ethanol at temperatures between 50° C. and 80° C., and also zinc-powder in the presence of ammonium chloride at temperatures between 20° C. and 80° C. The exact conditions for the respective compounds of formula I can be found in the experimental part.

Compounds of formula V, in which Y, R¹, R² and R³ are as described above, can be prepared according to scheme B by for example reacting a compound of formula VI, with a dioxinone (formula IV) in an inert solvent like for example toluene or xylene at elevated temperatures, preferably between 80° C. and 160° C.

Scheme C

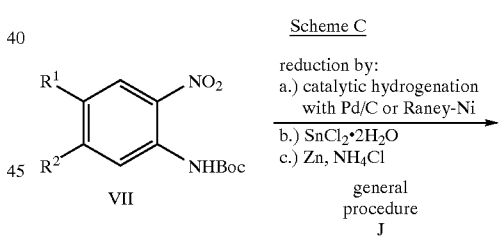

Compounds of formula II, in which R¹ and R² are as described above, can be prepared according to scheme C by reducing the nitro group in compounds of formula VII, in which R¹ and R² are as described above, to the amino group. The reduction can for example be carried out using hydrogen gas in presence of a suitable catalyst like for example Raney-Nickel or Palladium on carbon. Another possible reduction method is using tin(II)chloride (SnCl₂·2H₂O) in ethanol at temperatures between 70° C. and 80° C. (as described in *Tetrahedron Lett.* 1984, 25, 839), or alternatively in polar aprotic solvents, like DMF, DMA or NMP and the like, optionally in the presence of bases, like for example pyridine or triethylamine and the like, at temperatures between 0° C. and 80° C. Another suitable method is using zinc-powder in the presence of ammonium chloride in protic solvents like for example water or ethanol at temperatures between 20° C. and 80° C. The exact conditions for the respective compounds of formula II can be found in the experimental part.

Compounds of formula VII, in which $R^1$ and $R^2$ are as described above, can be prepared by different routes depending on the individual residues $R^1$ and $R^2$.

Scheme D

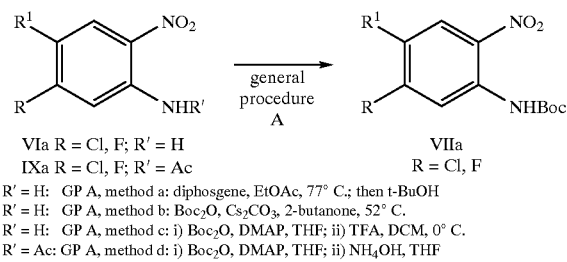

VIa R = Cl, F; R' = H
IXa R = Cl, F; R' = Ac
VIIa
R = Cl, F

R' = H: GP A, method a: diphosgene, EtOAc, 77° C.; then t-BuOH
R' = H: GP A, method b: Boc$_2$O, Cs$_2$CO$_3$, 2-butanone, 52° C.
R' = H: GP A, method c: i) Boc$_2$O, DMAP, THF; ii) TFA, DCM, 0° C.
R' = Ac: GP A, method d: i) Boc$_2$O, DMAP, THF; ii) NH$_4$OH, THF As described in scheme D, compounds of the formula VIIa, in which $R^1$ is as described above, R is chloro or fluoro and R' is hydrogen, can be prepared by protection of the amino group of compounds of the formula VIa, in which $R^1$ is as described above, R is chloro or fluoro and R' is hydrogen, with a tert.-butoxycarbonyl-group (BOC). One possibility for the protection of the amino function is for example reacting compounds of formula VIa with di-tert.-butyl-carbonate in the presence of a base such as cesium carbonate. The reaction can be carried out in polar solvents such as acetone or butanone and the like at temperatures between 20° C. and 80° C.

Alternatively, the protection of the amino group can be achieved by preparing the intermediate isocyanate by treatment of compounds of the formula VIa, in which $R^1$ is as described above, R is chloro or fluoro and R' is hydrogen, with diphosgene, preferably in aprotic solvents such as EtOAc or 1,4-dioxane at temperatures from 0° C. to 100° C., and subsequent treatment of the isocyanate with tert.-butanol in solvents such as dichloromethane or 1,2-dichloroethane and the like at temperatures between 20° C. and 85° C. to give the desired compounds of formula Va.

Another suitable method to achieve this protection step is the intermediate formation of a di-BOC compound by treatment of compounds of the formula VIa, in which $R^1$ is as described above, R is chloro or fluoro and R' is hydrogen, with di-tert.-butyl-carbonate in the presence of DMAP in an aprotic solvent such as tetrahydrofuran and the like, followed by selective removal of a single BOC-group by treatment with a Bronsted-acid, like e.g. TFA, in aprotic solvents such as dichloromethane, chloroform or 1,2-dichloroethane at temperatures between 0° C. and 20° C. to give the desired compounds of formula Va.

Yet another suitable method to produce compounds of formula IXa is the intermediate formation of a N—Ac-BOC compound by treatment of compounds of the formula VIa, in which $R^1$ is as described above, R is chloro or fluoro and R' is acetyl, with di-tert.-butyl-carbonate in the presence of DMAP in an aprotic solvent such as tetrahydrofuran and the like, followed by selective removal of a single BOC-group by treatment with a Bronsted-base, like e.g. aqueous ammonia (NH$_4$OH), in aprotic solvents such as tetrahydrofuran, diethylether or 1,4-dioxane and the like, at temperatures between 0° C. and 20° C. to give the desired compounds of formula Va.

Apparently, the protection of the amino function as shown in scheme D can be applied to a number of commercially available starting materials or compounds synthesized by standard transformations [e.g. nitration followed by selective ammonolysis of the halide in ortho-position to the newly introduced nitro-group as described in J. Med. Chem. 1994, 37,467; or ortho-nitration of acetanilide-compounds followed by deacetylation with for example aqueous potassium hydroxide solution or aqueous hydrochloric acid as described in Org. Synth. 1945, 25, 78 or in J. Med. Chem. 1985, 28, 1387] known to anyone skilled in the art to produce the corresponding 2-nitroanilines with the formula VIa, in which $R^1$ is as described above, R is chloro or fluoro and R' is hydrogen, or 2-nitroacetanilides with the formula IXa, in which $R^1$ is as described above, R is chloro or fluoro and R' is acetyl. The exact conditions for the respective compounds used in this invention can be found in the experimental part.

According to scheme E, compounds of formula VIb, in which $R^1$ is pyrrol-1-yl optionally substituted as described above, and R is hydrogen or chloro, can be prepared from commercially available 2-nitro-1,4-phenylenediamine [CAS-No. 5307-14-2] [for R=H] or known 5-chloro-2-nitro-1,4-phenylenediamine [CAS-No. 26196-45-2] [for R=Cl] by selective condensation of the 4-amino-group with a suitable substituted 2,5-dimethoxytetrahydrofuran with the formula X, as described in J. Heterocycl. Chem. 1988, 25, 1003.

Scheme E

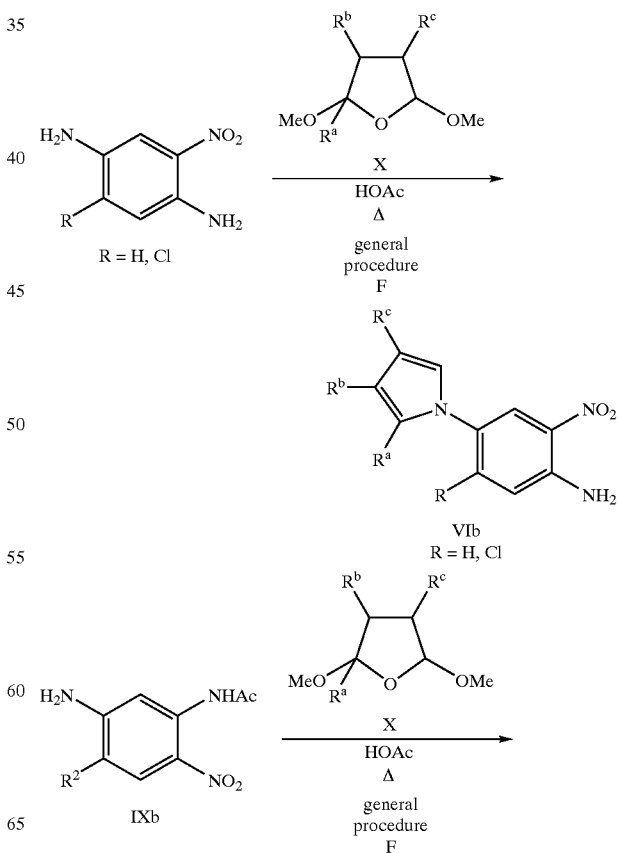

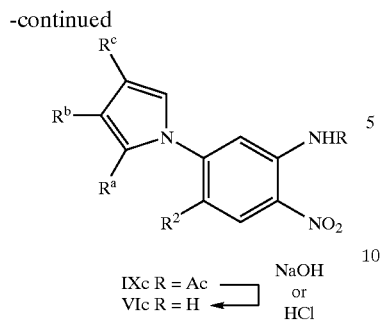

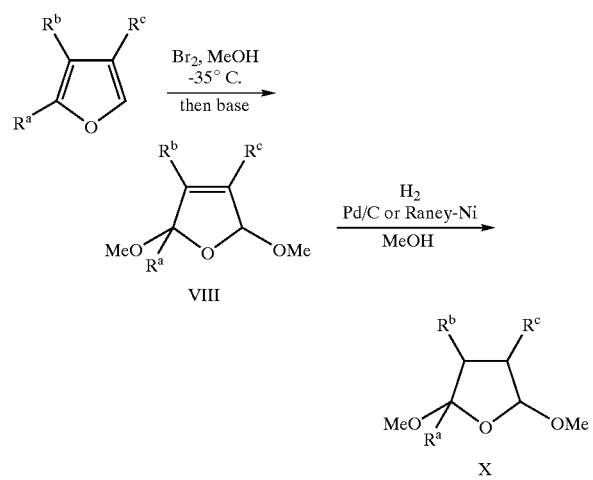

The reaction is preferably carried out in acidic media, like for example acetic acid or propionic acid and the like, at temperatures between 40° C. to 120° C. The exact conditions for the respective compounds can be found in the experimental part.

Also according to scheme E, compounds of the formula VIc, in which $R^1$ is pyrrol-1-yl and optionally substituted as described above and $R^2$ is also as described above, can be prepared from N-(5-amino-2-nitro-phenyl)-acetamide-compounds of the formula IXb, in which $R^2$ is as described above, by performing the same condensation reaction of the 5-amino-group with a suitable substituted 2,5-dimethoxytetrahydrofuran with the formula X as described for the reaction with the 2-nitro-1,4-phenylenediamine. The deacetylation of the compounds of formula IXc, in which $R^1$ is pyrrol-1-yl and optionally substituted as described above and $R^2$ is also as described above, to produce compounds of the formula VIc, in which $R^1$ is pyrrol-1-yl and optionally substituted as described above and $R^2$ is also as described above, can be done by standard acidic or basic hydrolysis reaction known to someone skilled in the art and the exact conditions for the respective compounds used in this invention can be found in the experimental part.

The synthesis of the corresponding N-(5-amino-2-nitro-phenyl)-acetamides with the formula IXb, in which $R^2$ is as described above, follows standard procedures known to someone skilled in the art and the exact conditions for the respective compounds used in this invention can be found in the experimental part.

The corresponding substituted 2,5-dimethoxytetrahydrofurans with the formula X, in which $R^a$, $R^b$ and $R^c$ are as described above in the general claim for the pyrrol-1-yl compounds, are either commercially available, or synthesized from the suitable substituted furan, as shown in scheme F. The corresponding substituents can optionally be protected with suitable protecting groups, known to someone skilled in the art, or alternatively can be introduced after the pyrrol ring synthesis. The two-step sequence consists of reacting the furan with bromine in MeOH at low temperature, like for example -35° C., followed by treatment with base, like for example triethyl-amine and the like or potassium carbonate or sodium hydrogen carbonate and the like. The resulting 2,5-dimethoxydihydrofuran with the formula VIII, in which $R^a$, $R^b$ and $R^c$ are as described above, can be reduced by catalytic hydrogenation, preferably in MeOH with catalysts like for example Palladium on carbon or Raney-Nickel and the like, to produce the desired 2,5-dimethoxytetrahydrofurans with the formula X. An example for this sequence can be found in *Tetrahedron* 1971, 27, 1973–1996.

The exact conditions for the individual compounds to be synthesized can be found in the experimental part.

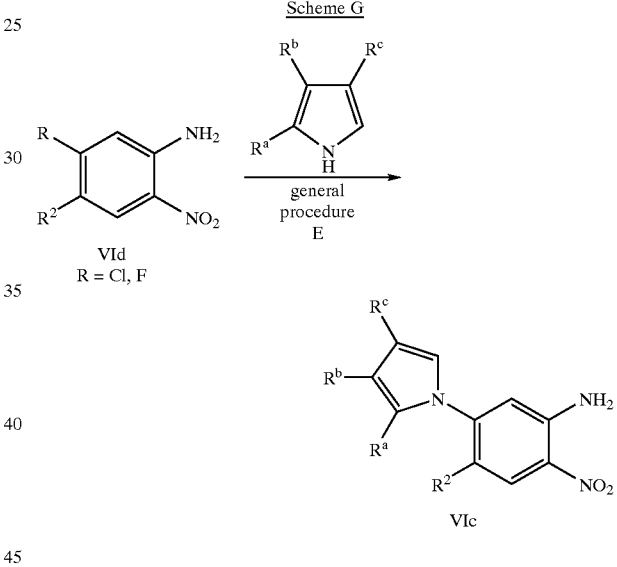

Another method of preparing compounds with the formula VIc, in which $R^1$ is pyrrol-1-yl, optionally substituted as described above, is by nucleophilic substitution reaction of compounds of the formula VId, in which R is chloro or fluoro and $R^2$ is as described above, with the corresponding pyrrol as shown in scheme F. The reaction is preferably carried out in a polar, aprotic solvent such as dimethyl formamide, N-methyl-pyrrolidone or dimethyl sulfoxide and the like. The base can be selected from the sterically hindered amines such as triethylamine or Hünig's base, alkoxides such as sodium methoxide and tert.-butoxide, or hydrides such as sodium hydride. The reaction can be performed at temperatures between 20° C. and 110° C., depending on the individual compounds to be synthesized. The exact conditions for the respective compounds used in this invention can be found in the experimental part.

As shown in scheme H, compounds of formula VIb and VIIc, in which $R^2$ is attached via a sulfur- or nitrogen-atom, respectively, and substituted with R' and R" as described above, can be prepared from compounds with the formula VIIa, in which $R^1$ is as described as above and R is chloro or fluoro, by a nucleophilic substitution reaction with the respective amines or mercaptanes in the presence of a suitable base.

Scheme H

Nitrogen nucleophiles

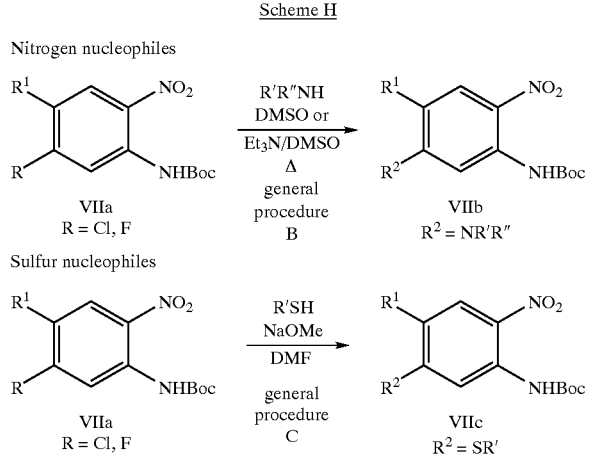

Sulfur nucleophiles

Oxygen alkylation

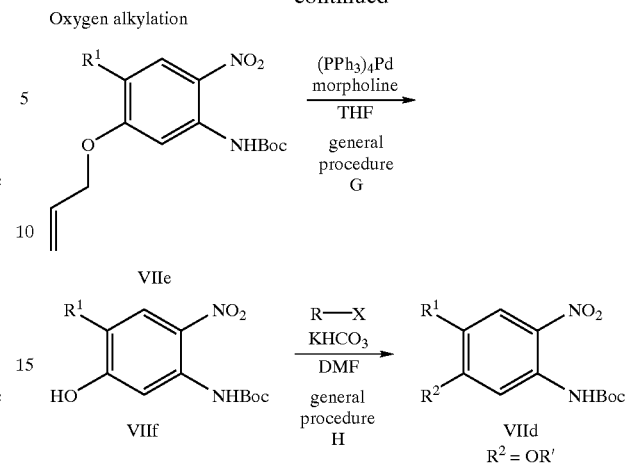

The reaction is preferably carried out in a polar, aprotic solvent such as dimethyl formamide, N-methyl-pyrrolidone or dimethyl sulfoxide and the like. The base can be selected from the sterically hindered amines such as triethylamine or Hünig's base, alkoxides such as sodium methoxide and tert.-butoxide, or hydrides such as sodium hydride. The reaction can be performed at temperatures between 20° C. and 110° C., depending on the individual compounds to be synthesized.

As shown in scheme I, compounds of formula VId, in which $R^2$ is attached via an oxygen atom and R' is as described as above, can be prepared from compounds of the formula VIa, in which $R^1$ is as described above and R is chloro or fluoro, by a nucleophilic aromatic substitution reaction with the respective alcohol (R'OH) in the presence of a suitable base to produce compounds of the formula VIe, where the protection of the amino function can be performed as described earlier. The base can be selected from the class of Bronsted bases such as potassium hydroxide and the like. The reaction is preferably carried out in a polar, aprotic solvent such as dimethyl formamide, N-methyl-pyrrolidone or dimethyl sulfoxide and the like at temperatures between 20° C. and 100° C.

Scheme I

Oxygen nucleophiles

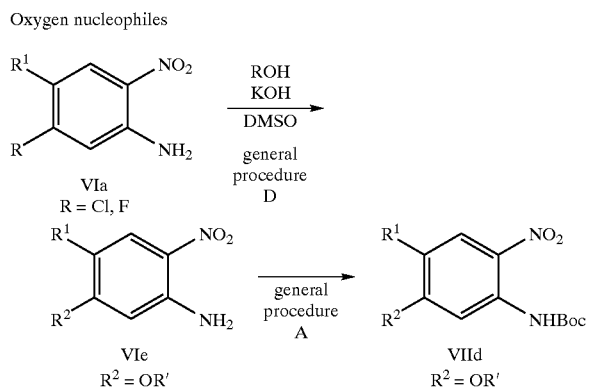

GP A, method a: diphosgene, EtOAc, 77° C.; then t-BuOH
GP A, method b: Boc₂O, Cs₂CO₃, 2-butanone, 52° C.
GP A, method c: i) Boc₂O, DMAP, THF; ii) TFA, DCM, 0° C.

Yet another method of preparing compounds of the formula VIId is using O-allyl compounds with the formula VIIe, in which $R^1$ is as described above, and perfoming a deallylation-alkylation sequence as outlined in scheme I. The deallylation is preferably carried out by transition-metal catalyzed isomerisation, e.g. in the presence of Rhodium(I)-salts like for example Wilkinson's catalyst [(PPh₃)₃RhCl] or Palladium(II)-salts such as [(PPh₃)₂PdCl₂], followed by aqueous acid hydrolysis of the resulting vinyl ether. An example for this procedure can be found in *J. Org. Chem.* 1973, 38, 3224. Another method for the deallylation is the reaction with Palladium(0)-complexes such as [(PPh₃)₄Pd] in the presence of excess of a secondary amine, as for example morpholine, as described for example in *Synthesis* 1996, 755. The alkylation of the resulting phenols with the formula VIIf, in which $R^1$ is as described above, to the desired compounds of the formula VIId can be carried out with electrophilic reagents of the formula R—X, in which R has the meaning of lower alkyl, lower alkenyl, alkyl acetate or benzyl and X represents a leaving group, for example iodide, bromide, methanesulfonate or tolylsulfonate, in a suitable solvent in the presence of a base. The reaction is preferably carried out in polar, aprotic solvents, for example chlorinated solvents such as dichloromethane, chloroform or dichloroethane, or amides, for example dimethylformamide, dimethylacetamide and N-methyl-pyrrolidone, or sulfoxides, for example dimethyl sulfoxide. The base can be selected from the sterically hindered amines such as Hünig's base, alkoxides such as sodium methoxide and tert.-butoxide, hydrides such as sodium hydride, hydroxides such as potassium hydroxide, carbonates such as potassium carbonate or hydrogen carbonates such as potassium hydrogen carbonate. The reaction can be performed at temperatures between −20° C. and 80° C., depending on the individual compounds to be synthesized. For the synthesis of the O-tert.-butyl compounds with the formula VIId, in which $R^1$ is as described above and $R^2$ is tert.-butoxy, the phenols with the formula VIIf can be treated with DMF-di-tert.-butylacetal in toluene or benzene at 80° C. as described in *Synthesis* 1983, 135.

Scheme J

Carbon nucleophiles

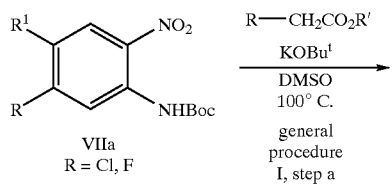

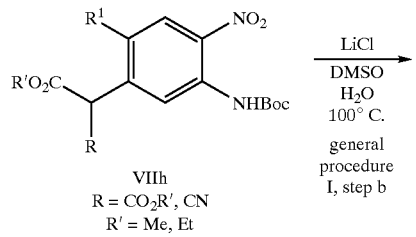

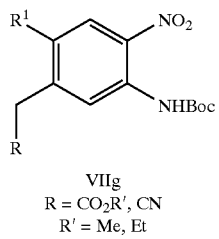

According to synthetic scheme J, compounds of formula VIIg, in which $R^2$ is attached via a carbon atom and is as described above, can be prepared from compounds with the formula VIIa, in which $R^1$ is as described as above and R is chloro or fluoro, by a nucleophilic substitution reaction with a malonic acid ester or -half-ester in the presence of a base as described for example in *Org. Prep. Proc. Int.* 1990, 22, 636–638, followed by the removal of one of the alkyl carboxylates via decarboxylation as described for example in *Synthesis* 1993, 51. The exact reaction conditions vary with the identity of the individual compounds and are described in the examples.

Scheme K

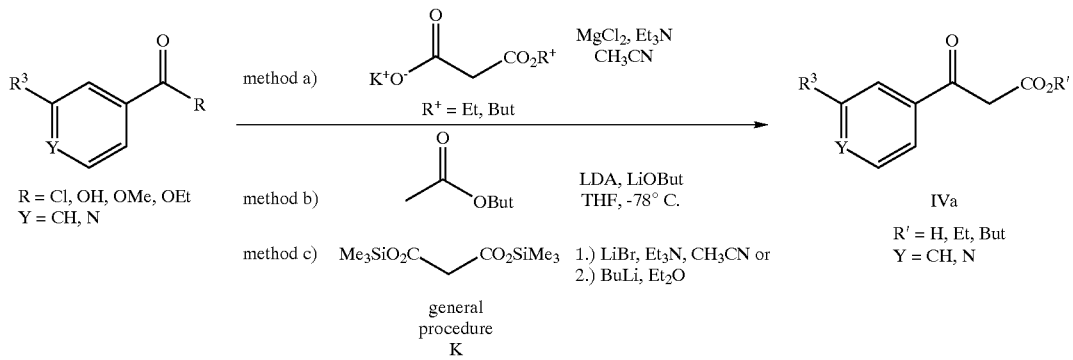

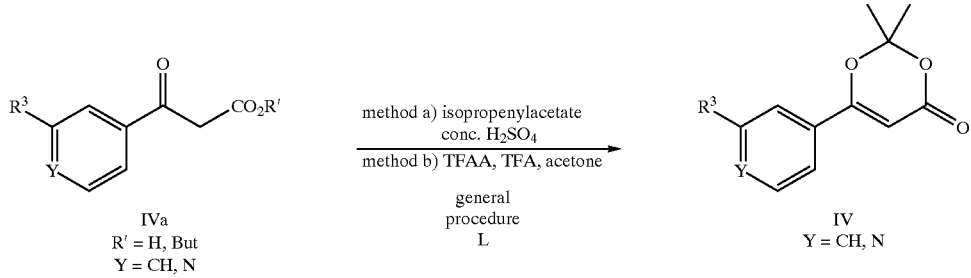

According to Scheme K, the dioxinones and β-keto esters building blocks with the formula IV and IVa can be prepared by methods known to someone skilled in the art from the corresponding carboxylic acid derivatives R³—COR, i.e. free acids, methyl or ethyl esters and acid chlorides. The exact conditions for the corresponding compounds can be found in the experimental part.

The pharmaceutically acceptable salts of the compound of formula I can be manufactured readily according to known methods and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The compounds of formula I and or pharmaceutically acceptable salts thereof are metabotropic glutamate receptor antagonists. A method of treatment or prevention of acute and/or chronic neurological disorders, such as psychosis, schizophrenia, Alzheimer's disease, cognitive disorders and memory deficits comprises administering an effective amount of the compound of formula I or a salt thereof to a person in need of such treatment. The method of the invention is useful for other indications such as restricted brain function caused by bypass operations or transplants, poor blood supply to the brain, spinal cord injuries, head injuries, hypoxia caused by pregnancy, cardiac arrest and hypoglycaemia. Further indications treatable by the method of the invention are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of formula I or a pharmaceutically acceptable salt thereof can be used as medicaments, e.g. in the form of pharmaceutical preparations in a suitable pharmceutical carrier. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I or a pharmaceutically acceptable salt thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a compound of formula I or a pharmaceutically acceptable salt thereof and a therapeutically inert excipient are also an object of the present invention, as is a process for the production of such compositions which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The present invention relates also to the use of compounds of formula I and of pharmaceutically acceptable salts thereof for in a method of treatment, especially for the control or prevention of acute and/or chronic neurological disorders of the aforementioned kind.

In Table I below some specific $K_i$ values of preferred compounds of the invention are presented. These values were obtained by indirect measurement of the affinity of the compounds for the recombinant rat mGluR2 expressed in CHO cells using a displacement binding assay with 3H-LY354740.

TABLE I

| Compound | $K_i$ mGlu2 ($\mu$M) |
|---|---|
| 4-[3-(5-hydroxymethyl-[1,2,3]triazol-1-yl)-phenyl]-7-morpholin-4-yl-8-trifluoromethyl-1,3-dihydro-benzo[b][1,4]diazepin-2-one | 0.074 |
| 4-(8-morpholin-4-yl-4-oxo-7-trifluoromethyl-4,5-dihydro-3H-benzo[b][1,4]diazepin-2-yl)-pyridine-2-carbonitrile | 0.020 |
| 3-(4-oxo-7-pyrrol-1-yl-4,5-dihydro-3H-benzo[b][1,4]diazepin-2-yl)-benzonitrile | 0.035 |
| 3-(8-iodo-4-oxo-7-pyrrol-1-yl-4,5-dihydro-3H-benzo[b][1,4]diazepin-2-yl)-benzonitrile | 0.075 |
| 3-[4-oxo-7-(3-phenyl-pyrrol-1-yl)-4,5-dihydro-3H-benzo[b][1,4]diazepin-2-yl]-benzonitrile | 0.075 |
| 4-(3-imidazol-1-yl-phenyl)-8-pyrrol-1-yl-1,3-dihydro-benzo[b][1,4]diazepin-2-one | 0.025 |
| 3-(8-methoxy-4-oxo-7-pyrrol-1-yl-4,5-dihydro-3H-benzo[b][1,4]diazepin-2-yl)-benzonitrile | 0.044 |
| 3-[7-(2-tert.-butyl-pyrrol-1-yl)-8-methoxy-4-oxo-4,5-dihydro-3H-benzo[b][1,4]diazepin-2-yl]-benzonitrile | 0.080 |
| 4-[3-(4-hydroxymethyl-thiazol-2-yl)-phenyl]-8-pyrrol-1-yl-1,3-dihydro-benzo[b][1,4]diazepin-2-one | 0.028 |
| 8-pyrrol-1-yl-4-(3-[1,2,3]triazol-1-yl-phenyl)-1,3-dihydro-benzo[b][1,4]diazepin-2-one | 0.0075 |
| 4-(3-oxazol-2-yl-phenyl)-8-pyrrol-1-yl-1,3-dihydro-benzo[b][1,4]diazepin-2-one | 0.023 |
| 5-[3-(4-oxo-7-pyrrol-1-yl-4,5-dihydro-3H-benzo[b][1,4]diazepin-2-yl)-phenyl]-oxazole-4-carboxylic acid ethyl ester | 0.029 |
| 2-[3-(4-oxo-7-pyrrol-1-yl-4,5-dihydro-3H-benzo[b][1,4]diazepin-2-yl)-phenyl]-oxazole-4-carboxylic acid amide | 0.062 |

TABLE I-continued

| Compound | $K_i$ mGlu2 ($\mu$M) |
|---|---|
| 2-[3-(4-oxo-7-pyrrol-1-yl-4,5-dihydro-3H-benzo[b][1,4]diazepin-2-yl)-phenyl]-oxazole-4-carboxylic acid (2-hydroxy-ethyl)-amide | 0.091 |
| 4-[3-(2-methyl-2H-pyrazol-3-yl)-phenyl]-7-morpholin-4-yl-8-trifluoromethyl-1,3-dihydro-benzo[b][1,4]diazepin-2-one | 0.006 |
| 4-(4-oxo-8-thiomorpholin-4-yl-7-trifluoromethyl-4,5-dihydro-3H-benzo[b][1,4]diazepin-2-yl)-pyridine-2-carbonitrile | 0.0009 |
| 7-ethoxy-4-[3-(5-hydroxymethyl-[1,2,3]triazol-1-yl)-phenyl]-8-trifluoromethyl-1,3-dihydro-benzo[b][1,4]diazepin-2-one | 0.0835 |
| 4-(8-ethoxy-4-oxo-7-trifluoromethyl-4,5-dihydro-3H-benzo[b][1,4]diazepin-2-yl)-pyridine-2-carbonitriie | 0.008 |
| 4-(8-methyl-4-oxo-7-trifluoromethyl-4,5-dihydro-3H-benzo[b][1,4]diazepin-2-yl)-pyridine-2-carbonitrile | 0.0085 |
| 2-[3-(3-methyl-isoxazol-5-yl)-phenyl]-4-oxo-8-thiomorpholin-4-yl-4,5-dihydro-3H-benzo[b][1,4]diazepine-7-carbonitrile | 0.0325 |
| 7-chloro-4-[3-(5-cyclopropylaminomethyl-[1,2,3]triazol-1-yl)-phenyl]-8-trifluoromethyl-1,3-dihydro-benzo[b][1,4]diazepin-2-one | 0.0155 |
| 4-[3-(5-cyclopropylaminomethyl-[1,2,3]triazol-1-yl)-phenyl]-7-methyl-8-trifluoromethyl-1,3-dihydro-benzo[b][1,4]diazepin-2-one | 0.026 |
| 7-methyl-4-(3-pyrazol-1-yl-phenyl)-8-trifluoromethyl-1,3-dihydro-benzo[b][1,4]diazepin-2-one | 0.070 |
| 4-[3-(2-hydroxymethyl-5-methyl-thiazol-4-yl)-phenyl]-7-methyl-8-trifluoromethyl-1,3-dihydro-benzo[b][1,4]diazepin-2-one | 0.0065 |

[$^3$H]-LY354740 Binding on mGlu2 Transfected CHO Cell Membranes

Transfection and Cell Culture cDNA encoding the rat mGlu2 receptor protein in pBluescript II was obtained from Prof. S. Nakanishi (Kyoto, Japan), and subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco BRL (Basel, Switzerland). Selection was made in the presence of G-418 (1000 ug/mL final). Clones were identified by reverse transcription of 5 $\mu$g total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM (NH4)$_2$SO$_4$, 2 mM MgCl$_2$, 25 units/mL Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[$^3$H]-LY354740 Binding

After thawing, the membranes were resuspended in cold 50 mM Tris-HCl buffer containing 2 mM MgCl$_2$ and 2 mM CaCl$_2$, (pH 7) (binding buffer). The final concentration of the membranes in the assays was 25 $\mu$g protein/mL. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/C glass fiber filters and washed 5 times with cold binding buffer. Non specific binding was measured in the presence of 10 $\mu$M DCG IV. After transfer of the filters into plastic vials containing 10 mL of Ultima-gold scintillation fluid (Packard, Zürich, Switzerland), the radioactivity was measured by liquid scintillation in a Tri-Carb 2500 TR counter (Packard, Zürich, Switzerland).

Data Analysis.

The inhibition curves were fitted with a four parameter logistic equation giving IC$_{50}$ values, and Hill coefficients and the K$_i$ values were calculated using the Cheng and Prusoff equation (Cheng, Y. and Prusoff, W. H., *Biochem. Pharmacol.* 1973, 22, 3099–3108). A small K$_i$ value expresses high affinity of the compound towards the receptor.

EXAMPLES

Unless stated to the contrary, all of the examples listed below were prepared and characterized as described.

General Procedure A

Preparation of (2-Nitro-phenyl)-carbamic Acid tert.-Butyl Esters from 2-Nitroanilines or 2-Nitroacetanilides Method a (from 2-nitroanilines): To a solution of diphosgene (4.1 mL, 34.1 mmol) in EtOAc (40 mL) at 0° C. was added a solution of the 2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 2-nitrophenylisocyanate as a yellow solid. This material was refluxed in a mixture of excess tert.-BuOH in CH$_2$Cl$_2$ for 2.5 h. Removal of the solvent left an orange solid which was purified by silica gel column chromatography with hexane/EtOAc to give the (2-nitro-phenyl)-carbamic acid tert.-butyl ester as a yellow solid.

Method b (from 2-nitroanilines): To a mixture of the 2-nitroaniline (142 mmol) and cesium carbonate (55.5 g, 170 mmol) in 2-butanone (740 mL) was dropwise added a solution of Boc$_2$O (37.8 g, 173 mmol) in 2-butanone (170 mL) and the resulting mixture was stirred at 50° C. to 80° C. until tlc indicated complete conversion. The solvent was removed in vacuum, the residue was treated with a mixture of H$_2$O (240 mL) and MeOH (240 mL) and extracted with hexane (3×500 mL). The combined hexane layer was washed with brine (200 mL) and all aqueous layers were reextracted with hexane (300 mL). All combined hexane layers were dried over MgSO$_4$, filtered and the solvent was removed in vacuum to give an orange solid, which was purified by silica gel column chromatography with hexane/EtOAc to give the (2-nitro-phenyl)-carbamic acid tert.-butyl ester as a yellow solid.

Method c (from 2-nitroanilines): To a solution of the 2-nitroaniline (550 mmol) and DMAP (1.22 g, 10 mmol) in THF (1000 mL) at 23° C. was dropwise added within 70 min a solution of Boc$_2$O (246 g, 1128 mmol) in THF (500 mL)

and stirring was continued at 23° C. for 75 min. The entire mixture was evaporated to dryness and dried at HV to leave a dark brown solid. This material was dissolved in DCM (1100 mL), cooled to 0° C. and TFA (84 mL, 1100 mmol) was added dropwise. The mixture was stirred at 0° C. for 2 h, poured into icecold sat. $NaHCO_3$-sol., extracted with DCM, washed with brine and dried over $MgSO_4$. Removal of the solvent in vacuum left a dark brown solid which was coated on silica gel and purified by silica gel column chromatography with hexane/EtOAc to give the (2-nitro-phenyl)-carbamic acid tert.-butyl ester as a yellow solid.

Method d (from 2-nitroacetanilides): To a solution of the 2-nitroacetanilide (100 mmol) and DMAP (122 mg, 1 mmol) in THF (100 mL) at 23° C. was dropwise added within 15 min a solution of $Boc_2O$ (22.92 g, 105 mmol) in THF (100 mL) and stirring was continued at 23° C. until tlc indicated completed conversion. The entire mixture was evaporated to dryness and dried at HV to leave a yellow to dark brown solid. This material was dissolved in THF (200 mL) and 25% $NH_4OH$ (77 mL, 500 mmol) was added dropwise. The mixture was stirred at 23° C. until tlc indicated complete conversion, poured into 1N HCl-sol., extracted with EtOAc, washed the organic layer with sat. $NaHCO_3$-sol. and brine, dried over MgSO4. Removal of the solvent in vacuum left an yellow to brown solid which was generally pure enough for further transformation or—if necessary—coated on silica gel and purified by silica gel column chromatography with hexane/EtOAc to give the (2-nitro-phenyl)-carbamic acid tert.-butyl ester as a yellow solid.

Example A1

(5-Fluoro-2-nitro-4-trifluoromethyl-phenyl)-carbamic Acid tert.-Butyl Ester

The title compound was prepared via the di-Boc-compound from 5-fluoro-2-nitro-4-trifluoromethyl-phenylamine [prepared from commercially available 4-amino-2-fluorobenzotrifluoride by: i.) acetylation with $Ac_2O$ in toluene at 23° C.; ii.) nitration with 100% nitric acid from 10–23° C.; iii.) deacetylation with 2N NaOH in THF at 50° C.] (5.21 g, 23.2 mmol) and $Boc_2O$ (10.63 g, 48.7 mmol), followed by treatment with 2 eq. TFA in $CH_2Cl_2$ according to the general procedure A (method c). Obtained as a light yellow solid (6.33 g, 84%).

MS (ISN) 323 [(M−H)$^-$]; mp 104° C.

Example A2

(2-Nitro-4-pyrrol-1-yl-phenyl)-carbamic Acid tert.-Butyl Ester

The title compound was prepared via the di-Boc-compound from 2-nitro-4-pyrrol-1-yl-phenylamine (Example F1) (13.5 g, 66.4 mmol) and $Boc_2O$ (30.45 g, 139 mmol), followed by treatment with 2 eq. TFA in $CH_2Cl_2$ according to the general procedure A (method c). Obtained as a yellow solid (16.0 g, 79%).

MS (ISN) 302 [(M−H)$^-$].

Example A3

[5-(2-Methoxy-ethoxy)-2-nitro-4-pyrrol-1-yl-phenyl]-carbamic Acid tert.-Butyl Ester The title compound was prepared from 5-(2-methoxy-ethoxy)-2-nitro-4-pyrrol-1-yl-phenylamine (Example D1) (711 mg, 2.6 mmol), $Cs_2CO_3$ (1.75 g, 5.4 mmol) and $Boc_2O$ (1.12 g, 5.1 mmol) in 2-butanone (20 mL) at 80° C. for 3.5 h according to the general procedure A (method b). Obtained as a yellow solid (865 mg, 89%).

MS (ISN) 376 [(M−H)$^-$]; mp 89–91° C.

Example A4

(5-Methoxy-2-nitro-4-pyrrol-1-yl-phenyl)-carbamic Acid tert.-Butyl Ester

The title compound was prepared via the di-Boc-compound from 5-methoxy-2-nitro-4-pyrrol-1-yl-phenylamine (Example D2) (5.77 g, 24.7 mmol) and $Boc_2O$ (11.1 g, 51 mmol), followed by treatment with 2 eq. TFA in $CH_2Cl_2$ according to the general procedure A (method c). Obtained as a yellow solid (5.56 g, 66%).

MS (ISN) 332 [(M−H)$^-$].

Example A5

[4-(2-tert.-Butyl-pyrrol-1-yl)-5-methoxy-2-nitro-phenyl]-carbamic Acid tert.-Butyl Ester The title compound was obtained as a side product in the preparation of Example A4 as a yellow solid (534 mg, 5.5%).

MS (ISN) 388 [(M−H)$^-$].

Example A6

(5-Cyanomethyl-4-iodo-2-nitro-phenyl)-carbamic Acid tert.-Butyl Ester

The title compound was prepared via the isocyanate from (5-amino-2-iodo-4-nitro-phenyl)-acetonitrile [prepared from 5-chloro-2-nitro-phenylamine by: i.) iodination with ICl/NaOAc in HOAc at 60° C.; ii.) reaction with ethyl cyanoacetate and KOBu$^t$ in DMSO at 100° C. for 2 h.; iii.) deacarboxylation with LiCl/$H_2O$ in DMSO at 120° C. for 2.5 h] (5.15 g, 17 mmol) and diphosgene (2.05 mL, 17 mmol) in EtOAc (150 mL), followed by treatment with tert.-BuOH (25 mL) in $CH_2Cl_2$ (25 mL) according to the general procedure A (method a). Obtained as a yellow solid (4.00 g).

MS (ISN) 402 [(M−H)$^-$]; mp 124–126° C.

Example A7

(5-Methoxy-2-nitro-4-trifluoromethyl-phenyl)-carbamic Acid tert.-Butyl Ester

The title compound was prepared via the di-Boc-compound from 5-methoxy-2-nitro-4-trifluoromethyl-phenylamine (Example D3) (4.14 g, 17.5 mmol) and $Boc_2O$ (8.04 g, 36.8 mmol), followed by treatment with 2 eq. TFA in $CH_2Cl_2$ according to the general procedure A (method c). Obtained as a yellow solid (5.86 g).

MS (ISN) 335 [(M−H)$^-$]; mp 68° C.

Example A8

(5-Fluoro-2-nitro-4-trifluoromethyl-phenyl)-carbamic Acid tert.-Butyl Ester

The title compound was prepared via the di-Boc-compound from 5-fluoro-2-nitro-4-trifluoromethyl-phenylamine [prepared from 3-fluoro-4-(trifluoromethyl)-aniline [CAS-No. 69411-68-3] by the following sequence: i.) acetylation with $Ac_2O$ in toluene at 23° C.; ii.) nitration 100% $HNO_3$ at 10–23° C. for 45 min; iii.) deacetylation with 2 N NaOH in THF at 50° C. for 6 h.] (5.21 g, 23.2 mmol) and Boc₂O (10.63 g, 48.7 mmol), followed by treatment with 2 eq. TFA in CH₂Cl₂ according to the general procedure A (method c). Obtained as a light yellow solid (6.33 g).

MS (ISN) 323 [(M−H)⁻]; mp 104° C.

Example A9

(5-Ethoxy-2-nitro-4-trifluoromethyl-phenyl)-carbamic Acid tert.-Butyl Ester The title compound was prepared via the di-Boc-compound from 5-ethoxy-2-nitro-4-trifluoromethyl-phenylamine (Example D4) (4.16 g, 16.6 mmol), and Boc₂O (7.62 g, 34.9 mmol), followed by treatment with 2 eq. TFA in CH₂Cl₂ according to the general procedure A (method c). Obtained as a yellow solid (5.54 g).

MS (ISN) 349 [(M−H)⁻]; mp 67° C.

Example A10

(4-Cyano-5-fluoro-2-nitro-phenyl)-carbamic Acid tert-Butyl Ester

The title compound was prepared via the di-Boc compound from 4-cyano-5-fluoro-2-nitroaniline (24.9 g, 137 mmol) [Ohmori et al. J. Med. Chem. 1994,37, 467–475] and Boc₂O (61.5 g, 282 mmol), followed by treatment with 2 eq. TFA in CH₂Cl₂ according to the general procedure A (method c). Obtained by column chromatography (hexane/ethylacetate 4:1) as a light yellow solid (14.5 g, 39%).

MS (ISN) 280.1 [(M−H)⁻].

Example A11

(5-Chloro-2-nitro-4-trifluoromethyl-phenyl)-carbamic Acid tert-Butyl Ester

The title compound was prepared via the di-Boc-compound from commercially available 5-chloro-2-nitro-4-trifluoromethyl-phenylamine [CAS-No. 35375-74-7] (22.61 g, 94 mmol) and Boc₂O (42.06 g, 193 mmol), followed by treatment with 2 eq. TFA in CH₂Cl₂ according to the general procedure A (method c). Obtained as a yellow solid (31.82 g, 99%).

MS (ISN) 339.1 [(M−H)⁻] and 341 [(M+2−H)⁻]; mp 113–115° C.

General Procedure B

Preparation of 5-N-Substituted-(2-nitro-phenyl)-carbamic Acid tert.-Butyl Esters (5-Chloro or -fluoro-2-nitro-phenyl)-carbamic acid tert.-butyl ester was stirred with the desired amine optionally with DMSO, DMF, DMA, NMP or THF and/or DIPEA or Et₃N at temperatures from 23° C. to 130° C. until tlc indicated complete disappearance of the chloride or fluoride. The reaction was cooled to 23° C. poured into ice-water, the precipitate was filtered off, washed with water and dried in vacuum. In cases were the product did not precipitate, the mixture was extracted with EtOAc, washed with water and brine, dried over Na₂SO₄. Filtration and removal of the solvent in vacuum left a crude product, which was—if necessary—purified by silica gel column chromatography with hexane/EtOAc to give the pure title compound.

Example B1

(5-Morpholin-4-yl-2-nitro-4-trifluoromethyl-phenyl)-carbamic Acid tert.-Butyl Ester The title compound was prepared from (5-fluoro-2-nitro-4-trifluoromethyl-phenyl)-carbamic acid tert.-butyl ester (Example A1) (1.62 g, 5.0 mmol) and morpholine (2.18 mL, 25.0 mmol) in DMSO (10 mL) at 23° C. according to the general procedure B. Obtained as a yellow solid (1.83 g).

MS (ISN) 390 [(M−H)⁻]; mp 75° C.

Example B2

(2-Amino-5-thiomorpholin-4-yl-4-trifluoromethyl-phenyl)-carbamic Acid tert.-Butyl Ester The title compound was prepared from (5-fluoro-2-nitro-4-trifluoromethyl-phenyl)-carbamic acid tert.-butyl ester (Example A1) (2.9 g, 8.94 mmol), Et₃N (5.6 mL, 40.23 mmol) and thiomorpholine (2.6 mL, 26.82 mmol) was stirred in DMSO (36 mL) at 23° C. according to the general procedure B. Obtained as a yellow solid (3.6 g).

MS (ISN) 406.4 [(M−H)⁻]; mp 97–99° C.

Example B3

(4-Cyano-5-morpholin-4-yl-2-nitro-phenyl)-carbamic Acid tert-Butyl Ester

The title compound was prepared from (4-cyano-5-fluoro-2-nitro-phenyl)-carbamic acid tert-butyl ester (Example A10) (4.67 g, 16.6 mmol) and morpholine (7.21 ml, 82.8 mmol) in DMSO (30 mL) at RT according to the general procedure B. Obtained as a yellow solid (5.01 g, 87%).

MS (ISP) 349.4 [(M+H)⁺].

Example B4

(4-Cyano-2-nitro-5-thiomorpholin-4-yl-phenyl)-carbamic Acid tert-Butyl Ester The title compound was prepared from (4-cyano-5-fluoro-2-nitro-phenyl)-carbamic acid tert-butyl ester (Example A10) (2.00 g, 7.11 mmol) and thiomorpholine (3.38 ml, 35.6 mmol) in DMSO (30 mL) at RT according to the general procedure C. Obtained as a light yellow solid (2.20 g, 85%).

MS (ISP) 363.1 [(M−H)⁻].

Example B5

(5-Methyl-2-nitro-4-trifluoromethyl-phenyl)-carbamic Acid tert-Butyl Ester

To a suspension of (5-chloro-2-nitro-4-trifluoromethyl-phenyl)-carbamic acid tert-butyl ester (Example A11) (5.00 g, 14.7 mmol) and tetrakis(triphenylphosphine)-palladium in dioxane/water (9:1; 50 ml) was added at RT trimethyl-boroxine (2.04 ml, 14.7 mmol). The reaction mixture was stirred under reflux conditions for 15 h, filtered, evaporated and purified by column chromatography on silica gel (hexane/ethyl acetate 9:1) to yield a light yellow solid (3.25 g, 69%).

MS (ISP) 319.2 [(M−H)⁻].

General Procedure C

Preparation of 5-S-Substituted-(2-nitro-phenyl)-carbamic Acid tert.-Butyl Esters To a solution of the thiol (2.2 mmol) in DMF was added NaOMe-sol. (5.4M in MeOH, 0.41 mL, 2.2 mmol) followed by the (5-chloro- or -fluoro-2-nitro-phenyl)-carbamic acid tert.-butyl ester (2.0 mmol) and stirring was continued at 23°

C. until tlc indicated complete disappearance of the chloride or fluoride. Poured into ice-cold 5% citric acid, extracted with EtOAc, washed with sat. $NaHCO_3$-sol., brine, dried over $MgSO_4$. Removal of the solvent left an orange oil, which was purified by silica gel column chromatography with hexane/EtOAc to give the pure title compound.

General Procedure D

Preparation of 5-O-Substituted-2-nitro-phenylamines

To a suspension of KOH (85%, 3.62–7.96 g, 55–121 mmol) in DMSO (50 mL) was added the alcohol (125–500 mmol) and the mixture was stirred at 23° C. until all KOH had dissolved. The 5-chloro-or-fluoro-2-nitro-phenylamine (50 mmol) was added in small portions and the resulting dark red clear solution was stirred at 23–60° C. until tlc indicated complete disappearance of the chloride or fluoride. Poured into ice-cold 1N HCl or ice-cold sat. $NH_4Cl$-sol., the precipitate was filtered off, washed with water and dried in vacuum. In cases were the product did not precipitate, the mixture was extracted with EtOAc, washed with 1N HCl or sat. $NH_4Cl$-sol. and brine, dried over $MgSO_4$. Removal of the solvent left a dark red solid, which was—if necessary—purified by silica gel column chromatography with hexane/EtOAc to give the pure title compound.

Example D1

5-(2-Methoxy-ethoxy)-2-nitro-4-pyrrol-1-yl-phenylamine

The title compound was prepared from 5-chloro-2-nitro-4-pyrrol-1-yl-phenylamine (Example F3) (1.01 g, 4 mmol), 2-methoxyethanol (1.58 mL, 20 mmol) and KOH (316 mg, 4.8 mmol) in DMSO (5 mL) according to the general procedure E. Obtained as an orange solid (870 mg).

MS (ISN) 276 [(M–H)$^-$]; mp 115–118° C.

Example D2

5-Methoxy-2-nitro-4-pyrrol-1-yl-phenylamine

The title compound was prepared from 5-chloro-2-nitro-4-pyrrol-1-yl-phenylamine (Example F3) (5.94 g, 25 mmol), methanol (25 mL) and KOH (1.98 g, 30 mmol) in DMSO (25 mL) according to the general procedure E. Obtained as an orange solid (5.88 g).

MS (ISP) 234 [(M+H)$^+$].

Example D3

5-Methoxy-2-nitro-4-trifluoromethyl-phenylamine

The title compound was prepared from 5-chloro-2-nitro-4-trifluoromethyl-phenylamine [CAS-No. 35375-74-7] (4.61 g, 19.2 mmol) and KOH (2.78 g, 42.2 mmol) in MeOH (20 mL) and DMSO (40 mL) according to the general procedure E. Obtained as a yellow solid (4.18 g).

MS (ISN) 235 [(M–H)$^-$]; mp 56° C.

Example D4

5-Ethoxy-2-nitro-4-trifluoromethyl-phenylamine

The title compound was prepared from 5-chloro-2-nitro-4-trifluoromethyl-phenylamine [CAS-No. 35375-74-7] (7.06 g, 29.3 mmol) and KOH (4.26 g, 64.6 mmol) in EtOH (30 mL) and DMSO (60 mL) according to the general procedure E. Obtained as a yellow solid (4.20 g).

MS (ISN) 249 [(M–H)$^-$]; mp 95° C.

General Procedure E

Preparation of 2-Nitro-5-pyrrol-1-yl-phenylamines

Method a: A solution of the 5-chloro-or-fluoro-2nitro-phenylamine (10 mmol), the pyrrole (40 mmol) and KOH (85%w/w, 990 mg, 15 mmol) in DMSO (8.6 mL) was stirred for at 80° C. under argon atmosphere until tlc indicated complete conversion of the chloride or fluoride [cf. *J. Med. Chem.* 1994, 37, 467]. Poured into ice-cold 1N HCl or ice-cold sat. $NH_4Cl$-sol., the precipitate was filtered off, washed with water and dried in vacuum. In cases were the product did not precipitate, the mixture was extracted with EtOAc, washed with 1N HCl or sat. $NH_4Cl$-sol. and brine, dried over $MgSO_4$. Removal of the solvent left a dark red solid, which was—if necessary—purified by silica gel column chromatography with hexane/EtOAc to give the pure title compound.

Method b: To solution of the pyrrole (10 mmol) dry DMF (20 mL) at 0° C. was added NaH (60% in mineral oil, 480 mg, 12 mmol) in 3 portions, followed by the 5-chloro-or fluoro-2-nitroaniline (10 mmol). The mixture was heated to 150° C. under argon atmosphere until tlc indicated complete conversion of the chloride or fluoride [cf. *J. Med. Chem.* 1992, 35, 4455]. Poured into ice-cold 1N HCl or ice-cold sat. $NH_4Cl$-sol., the precipitate was filtered off, washed with water and dried in vacuum. In cases were the product did not precipitate, the mixture was extracted with EtOAc, washed with 1N HCl or sat. $NH_4Cl$-sol. and brine, dried over $MgSO_4$. Removal of the solvent left a dark red solid, which was—if necessary—purified by silica gel column chromatography with hexane/EtOAc to give the pure title compound.

Example E1

2-Nitro-5-pyrrol-1-yl-phenylamine

The title compound was prepared from 5-chloro-2nitroaniline (1.73 g, 10 mmol), pyrrole (2.8 mL, 40 mmol) and KOH (85%, 990 mg, 15 mmol) in DMSO (8.6 mL) at 80° C. for 24 h according to the general procedure E (method a). Obtained as a brown solid (1.52 g).

MS (EI) 203 (M$^+$); mp >250° C. (dec.).

Example E2

1-(3-Amino-4-nitro-phenyl)-4-(2-chloro-phenyl)-1H-pyrrole-3-carbonitrile

The title compound was prepared from 5-chloro-2nitroaniline, 4-(o-Chlorophenyl)-pyrrole-3-carbonitrile [CAS-No. 74738-15-1] and NaH in DMF at 150° C. for 3 h according to the general procedure E (method b). Obtained as a yellow-brown solid (218 mg).

MS (ISN) 337 [(M–H)$^-$] and 339 [(M+2–H)$^-$]; mp 267–270° C. (dec.).

Example E3

1-(3-Amino-4-nitro-phenyl)-4-phenyl-1H-pyrrole-3-carbonitrile

Prepared from 5-chloro-2nitroaniline, 4-phenyl-pyrrole-3-carbonitrile [CAS-no. 40167-37-1] and NaH in DMF at 150° C. for 3 h according to the general procedure E (method b). Obtained as a dark red solid (168 mg).

MS (ISN) 303 [(M–H)$^-$]; mp 193–194° C.

General Procedure F

Preparation of 2-Nitro-4-(pyrrol-1-yl)-phenylamines or N-[5-(Pyrrol-1-yl)-2-nitro-phenyl]-acetamides by Condensation of 2-Nitro-1,4-phenylenediamines or N-[5-Amino-2-nitro-phenyl]-acetamides with 2,5-Dimethoxytetrahydrofurans [cf. J. Heterocycl. Chem. 1988, 25, 1003–1005]

A mixture of the 2-nitro-1,4-phenylenediamine or N-[5-amino-2-nitro-phenyl]-acetamide (25 mmol), the 2,5-dimethoxytetrahydrofuran (26–32.5 mmol) in HOAc (7–150 mL) was stirred at 60–120° C. until tlc indicated complete conversion of the amine. After cooling to 23° C., the mixture was poured into brine (500 mL) and extracted with EtOAc (3×200 mL). The combined organic layers were washed with brine (300 mL) and dried over MgSO$_4$. Removal of the solvent left a brown residue, which was purified by silica gel column chromatography with cyclohexane/EtOAc to give the title compound.

The acidic or basic hydrolysis reactions from the N-[5-(pyrrol-1-yl)-2-nitro-phenyl]-acetamides to produce the 2-nitro-5-(pyrrol-1-yl)-phenylamines are described with the specific examples.

Example F1

2-Nitro-4-pyrrol-1-yl-phenylamine

The title compound was prepared from 2-nitro-1,4-phenylenediamine (20 g, 131 mmol), 2,5-dimethoxytetrahydrofuran (18.3 mL, 135 mmol) in HOAc (37 mL) at 95° C. for 3 h according to the general procedure F. Obtained as a red solid (13.5 g).

MS (EI) 203 (M$^+$).

Example F2

4-Iodo-2-nitro-5-pyrrol-1-yl-phenylamine

The title compound was prepared from N-(5-amino-4-iodo-2-nitro-phenyl)-acetamide (228 mg, 0.71 mmol) [prepared from commercially available 5-chloro-2-nitroaniline by the following sequence: i.) iodination with iodine monochloride, NaOAc in HOAc according to Wilson, J. Gerald; Hunt, Frederick C. Aust. J. Chem. 1983, 36, 2317–25; ii.) nucleophilic aromatic substitution with NaN$_3$ in DMSO at 80° C. for 15 h; iii.) acetylation with AcCl in HOAc at 120° C. for 2 h according to Eur. J. Med. Chem. 1988, 23, 553; iv.) Staudinger-reduction with PPh$_3$/H$_2$O in THF at 23° C. for 1 h] and 2,5-dimethoxytetrahydrofuran (0.14 mL, 1.08 mmol) in HOAc (10 mL) at 95° C. for 2 h according to the general procedure F. Obtained as a yellow solid (221 mg). Deacetylation of this material (371 mg, 1.0 mmol) was perfomed by stirring with 1 N NaOH (2.0 mL, 2.0 mmol) in THF (3.4 mL) at 60° C. for 21 h. Obtained as a yellow solid (312 mg).

MS (ISN) 328 [(M−H)$^-$]; mp 150° C.

Example F3

5-Chloro-2-nitro-4-pyrrol-1-yl-phenylamine

The title compound was prepared from 5-chloro-2-nitro-1,4-phenylenediamine [CAS-no. 26196-45-2] (4.69 g, 25 mmol), 2,5-dimethoxytetrahydrofuran (4.2 mL, 32.5 mmol) in HOAc (150 mL) at 95° C. for 2 h according to the general procedure F. Obtained as a red solid (4.10 g).

MS (ISN) 236 (M$^+$) and 238 [(M+2−H)$^-$].

Example F4

1-(3-Amino-4-nitro-phenyl)-1H-pyrrole-3-carbaldehyde

The title compound was prepared from 4-nitro-3-phenylendiamine and 2,5-dimethoxy-3-tetrahydrofuran-carboxaldehyde [CAS-no. 50634-05-4] in HOAc/toluene at 95° C. for 3 h according to the general procedure F. Obtained as an orange-brown solid (80 mg).

MS (EI) 231 (M$^+$).

Example F5

[1-(3-Amino-4-nitro-phenyl)-1H-pyrrol-3-yl]-methanol

The title compound was prepared from 1-(3-amino-4-nitro-phenyl)-1H-pyrrole-3-carbaldehyde (Example F4) by reduction with 2 eq. NaBH$_4$ in EtOH at 23° C. for 30 min. Obtained as a brown solid (20 mg).

MS (EI) 233 (M$^+$).

Example F6

2-Nitro-5-(3-phenyl-pyrrol-1-yl)-phenylamine

The title compound was prepared from N-(5-amino-2-nitro-phenyl)-acetamide [prepared from commercially available 5-chloro-2-nitroaniline by the following sequence: i.) nucleophilic aromatic substitution with NaN$_3$ in DMSO at 80° C. for 15 h; ii.) acetylation with AcCl in HOAc at 120° C. for 2 h according to Eur. J. Med. Chem. 1988, 23, 553; iii.) Staudinger-reduction with PPh$_3$/H$_2$O in THF at 23° C. for 1 h] and 2,5-dimethoxy-3-phenyl-tetrahydro-furan [CAS-no. 207119-66-2] in HOAc at 60° C. for 2 days according to the general procedure F. Obtained as a brown solid (414 mg). Deacetylation of this material was perfomed by stirring with 25% HCl in THF at 80° C. for 90 min. Obtained as a brown solid (179 mg).

MS (ISN) 278 [(M−H)$^-$].

Example F7

5-(3-Methoxymethyl-pyrrol-1-yl)-2-nitro-phenylamine

The title compound was prepared from N-(5-amino-2-nitro-phenyl)-acetamide [prepared from commercially available 5-chloro-2-nitroaniline as described in Example F6] and 2,5-dimethoxy-3-methoxymethyl-tetrahydro-furan [prepared from (2,5-dimethoxy-tetrahydro-furan-3-yl)-methanol [CAS-no. 207119-66-2] by methylation with 2.1 eq. NaH (95%) and 5.5 eq. MeI in Et$_2$O at 0° C. for 2 h] in HOAc at 60° C. for 18 h according to the general procedure F. Obtained as a light yellow solid (86 mg). Deacetylation of this material was perfomed by stirring with 2 eq. 2 N NaOH-sol. in 1,4-dioxane at 60° C. for 2 h. Obtained as a yellow solid (69 mg).

MS (ISN) 246 [(M−H)$^-$].

Example F8

5-(2-Methoxymethyl-pyrrol-1-yl)-2-nitro-phenylamine

The title compound was prepared from N-(5-amino-2-nitro-phenyl)-acetamide [prepared from commercially available 5-chloro-2-nitroaniline as described in Example F6] and 2,5-dimethoxy-2-methoxymethyl-tetrahydro-furan

[CAS-no. 98560-90-8] in HOAc at 60° C. for 2 h according to the general procedure F. Obtained as a light brown solid (620 mg). Deacetylation of this material was perfomed by stirring with 2 eq. 2 N NaOH-sol. in 1,4-dioxane at 60° C. for 21 h. Obtained as a yellow solid (511 mg).

MS (ISN) 246 [(M−H)⁻].

Example F9

1-(3-Amino-4-nitro-phenyl)-1H-pyrrole-2-carboxylic Acid Methyl Ester

The title compound was prepared from N-(5-amino-2-nitro-phenyl)-acetamide [prepared from commercially available 5-chloro-2-nitroaniline as described in Example F6] and 2,5-dimethoxy-tetrahydro-furan-2-carboxylic acid methyl ester [CAS-no. 39658-49-6] in HOAc at 60° C. for 2 h according to the general procedure F. Obtained as a light yellow solid (757 mg). Deacetylation of this material was perfomed by stirring with 10 eq. NaOMe-sol. in MeOH at 23° C. for 1 h. Obtained as a yellow solid (594 mg).

MS (ISN) 260 [(M−H)⁻]; mp 156–158° C.

General Procedure G

Preparation of (5-Hydroxy-2-nitro-phenyl)-carbamic Acid tert.-Butyl Esters by Deallylation of (5-Allyloxy-2-nitro-phenyl)-carbamic Acid tert.-Butyl Esters Method a: A mixture of the (5-allyloxy-2-nitro-phenyl)-carbamic acid tert.-butyl ester, $(PPh_3)_3RhCl$ (5 mol %) and DABCO (20 mol %) in EtOH was refluxed for 2.5 h according to J. Org. Chem. 1973, 38, 3224. Added 5% citric acid, stirred at 23° C. for 15 min, extracted with EtOAc, washed with brine, dried over $MgSO_4$. Removal of the solvent left an orange solid, which was purified by silica gel column chromatography with hexane/EtOAc to give the title compound.

Method b: This Method is Also Used for the Deallylation of Allylesters.

A mixture of the (5-allyloxy-2-nitro-phenyl)-carbamic acid tert.-butyl ester or allyl ester (10 mmol) and $(PPh_3)_4Pd$ (116 mg, 1 mol %) in THF (50 mL) was degassed for 10 min. Then morpholine (8.71 mL, 100 mmol) was added and the mixture was stirred at 0° C. to 23° C. until tlc indicated complete conversion of the allyl-compound (more $(PPh_3)_4Pd$ in portions of 0.5 mol % could be added in 24 h intervals to achieve complete conversion). Diluted with EtOAc, washed with 5% citric acid or 1 M HCl and brine, dried over $MgSO_4$. Removal of the solvent in vacuum left a solid, which was—if necessary—purified by silica gel column chromatography with hexane/EtOAc to give the title compound.

General Procedure H

Preparation of 5-O-Substituted-(2-nitro-phenyl)-carbamic Acid tert.-Butyl Esters from (5-Hydroxy-2-nitro-phenyl)-carbamic Acid tert.-Butyl Esters A mixture of the (5-hydroxy-2-nitro-phenyl)-carbamic acid tert.-butyl ester (10 mmol), $KHCO_3$ (1.30 g, 13 mmol) and the appropriate alkylating reagent (20 mmol) were stirred in DMF (20 mL) at 23 to 60° C. until tlc indicated complete conversion. Dilution with EtOAc was followed by aqueous workup with 5% citric acid, sat. $NaHCO_3$-sol., brine and drying over $MgSO_4$. Removal of the solvent left a crude material, which was purified by silica gel column chromatography with hexane/EtOAc to give the title compound.

General Procedure I

Preparation of (5-tert.-Butoxycarbonylamino-4-nitro-phenyl)-acetic Acid Methyl Esters and (5-Cyanomethyl-4-iodo-2-nitro-phenyl)-carbamic Acid tert.-Butyl Esters Step a: Nucleophilic Aromatic Substitution with Malonic Esters To a solution of KOBut (0.56 g, 5.02 mmol) in DMSO (3 mL) was added dimethyl malonate (0.58 mL, 5.02 mmol) or ethyl cyanoacetate (0.54 mL, 5.02 mmol) followed by the (5-chloro-or -fluoro-2-nitro-phenyl)-carbamic acid tert.-butyl ester (2.51 mmol) and the resulting dark red clear solution was stirred at 100° C. until tlc indicated complete disappearance of the chloride or fluoride [cf. Org. Prep. Proc. Int. 1990,22, 636–638]. Poured into ice-cold 5% citric acid (100 mL), extracted with EtOAc (2×100 mL), washed with brine, dried over $MgSO_4$. Removal of the solvent left a yellow oil, which was purified by silica gel column chromatography with hexane/EtOAc to give the pure title compound as a yellow gum.

Step b: Decarboxylation Reaction.

A mixture of the above 2-(5-tert.-butoxycarbonylamino-4-nitro-phenyl)-malonic acid methyl ester (6.76 mmol), LiCl (573 mg, 13.52 mmol) and $H_2O$ (0.122 mL, 6.76 mmol) in DMSO (46 mL) was stirred at 100° C. to 120° C. until tlc indicated complete decarboxylation [cf. Synthesis 1993, 51]. Poured into ice-water, extracted twice with EtOAc, washed with brine, dried over $MgSO_4$. Removal of the solvent left a yellow oil, which was purified by silica gel column chromatography with hexane/EtOAc to give the pure title compound as a yellow solid.

General Procedure J

Preparation of the (2-Amino-phenyl)-carbamic Acid tert.-Butyl Esters by Reduction of (2-Nitro-phenyl)-carbamic Acid tert.-Butyl Esters Method a: Catalytic Hydrogenation.

A mixture of the nitro compound (1.0 mmol) in MeOH or EtOH and THF (1:1 ca. 20 mL) and 5–10% Palladium on carbon (20 mg) or Raney-Ni (20 mg) was stirred vigorously at 23° C. under hydrogen atmosphere until tlc indicated complete conversion. The catalyst was filtered off, washed thoroughly with MeOH or EtOH and THF (1:1), the solvent was removed in vacuum to give the title compound, which was generally pure enough for further transformations.

Method b: Reduction with $SnCl_2.2H_2O$.

A mixture of the nitro compound (1.0 mmol) and $SnCl_2.2H_2O$ (5.0 mmol) was either stirred in EtOH (30 mL) at 70–80° C. or alternatively in pyridine (3 mL) and DMF (12 mL) at 23° C. under Argon atmosphere until tlc indicated complete conversion [cf. Tetr. Lett. 1984, 25, 839]. The reaction mixture was brought to pH 8 by addition of sat. $NaHCO_3$-sol. and extracted with EtOAc (2×100 mL). The combined organic layer were washed with brine and dried over $Na_2SO_4$. Removal of the solvent left a yellow solid, which—if necessary—can be purified by silica gel column chromatography.

Method c: Reduction with Zn and $NH_4Cl$.

To a mixture of the nitro compound (1.0 mmol) in EtOH/THF/sat. $NH_4Cl$-sol. (1:1:1, 30 mL) was added Zinc dust (3.0 mmol) and the mixture was stirred at 70° C. under Argon atmosphere until tlc indicated complete conversion. Aqueous workup as described in method b.

Method d: Reduction with Fe and HOAc.

To a mixture of the nitro compound (1.0 mmol) in $THF/H_2O$ (4:1, 10–50 mL) was added Fe powder (6.0 mmol), followed by HOAc (10–12 drops) and the mixture was stirred at 70° C. under Argon atmosphere until tlc indicated complete conversion. Aqueous workup as described in method b.

Example J1

(2-Amino-5-morpholin-4-yl-4-trifluoromethyl-phenyl)-carbamic Acid tert.-Butyl Ester The title compound was prepared from (5-morpholin-4-yl-2-nitro-4-trifluoromethyl-phenyl)-carbamic acid tert.-butyl ester (Example B1) by hydrogenation with 10% Pd/C according to the general procedure J (method a). Obtained as an amorphous red substance (1.72 g).

MS (ISP) 362 [(M+H)$^+$].

Example J2

(2-Amino-4-pyrrol-1-yl-phenyl)-carbamic Acid tert.-Butyl Ester

The title compound was prepared from (2-nitro-4-pyrrol-1-yl-phenyl)-carbamic acid tert.-butyl ester (Example A2) by hydrogenation with 5% Pd/C according to the general procedure J (method a). Obtained as a white solid (9.06 g).

MS (ISP) 274 [(M+H)$^+$].

Example J3

[2-Amino-5-(2-methoxy-ethoxy)-4-pyrrol-1-yl-phenyl]-carbamic Acid tert.-Butyl Ester The title compound was prepared from [5-(2-methoxy-ethoxy)-2-nitro-4-pyrrol-1-yl-phenyl]-carbamic acid tert.-butyl ester (Example A3) by hydrogenation with Raney-Nickel according to the general procedure J (method a). Obtained as an orange solid (196 mg).

MS (ISP) 348 [(M+H)$^+$]; mp 117–119° C.

Example J4

(2-Amino-5-methoxy-4-pyrrol-1-yl-phenyl)-carbamic Acid tert.-Butyl Ester

The title compound was prepared from (5-methoxy-2-nitro-4-pyrrol-1-yl-phenyl)-carbamic acid tert.-butyl ester (Example A4) (5.52 g, 16.6 mmol) by hydrogenation with 10% Pd/C according to the general procedure J (method a). Obtained as a light pink solid (4.1 g).

MS (ISP) 304 [(M+H)$^+$]; mp 134° C.

Example J5

[2-Amino-4-(2-tert.-butyl-pyrrol-1-yl)-5-methoxy-phenyl]-carbamic Acid tert.-Butyl Ester The title compound was prepared from [4-(2-tert.-butyl-pyrrol-1-yl)-5-methoxy-2-nitro-phenyl]-carbamic acid tert.-butyl ester (Example A5) (513 mg, 1.32 mmol) by hydrogenation with 10% Pd/C according to the general procedure J (method a). Obtained as a light brown gum (110 mg).

MS (ISP) 360 [(M+H)$^+$].

Example J6

(2-Amino-5-cyanomethyl-4-iodo-phenyl)-carbamic Acid tert.-Butyl Ester

The title compound was prepared from (5-morpholin-4-yl-2-nitro-4-trifluoromethyl-phenyl)-carbamic acid tert.-butyl ester (Example B1) (1.33 g, 3.3 mmol) by reduction with SnCl$_2$.2H$_2$O according to the general procedure J (method b). Obtained as a yellow solid (391 mg).

MS (EI) 373 (M$^+$); mp 152–154° C.

Example J7

(2-Amino-5-thiomorpholin-4-yl-4-trifluoromethyl-phenyl)-carbamic Acid tert.-Butyl Ester The title compound was prepared from (2-nitro-5-thiomorpholin-4-yl-4-trifluoromethyl-phenyl)-carbamic acid tert.-butyl ester (Example B2) (1.2 g, 2.95 mmol) by reduction with SnCl$_2$.2H$_2$O according to the general procedure J (method b). Obtained as a yellow solid (978 mg).

MS (ISP) 378.3 [(M+H)$^+$]; mp 117–119° C.

Example J8

[2-Amino-5-(1,1-dioxo-1l 6-Thiomorpholin-4-yl)-4-trifluoromethyl-phenyl]-carbamic Acid tert.-Butyl Ester The title compound was prepared from [5-(1,1-dioxo-1l 6-thiomorpholin-4-yl)-2-nitro-4-trifluoromethyl-phenyl]-carbamic acid tert.-butyl ester [prepared from (2-amino-5-thiomorpholin-4-yl-4-trifluoromethyl-phenyl)-carbamic acid tert.-butyl ester (Example B2) (2.4 g, 5.89 mmol) by oxidation with a 0.3M ammoniummolybdate solution (1.8 mL) and 30% H$_2$O$_2$ (13.6 mL) in acetone (14.7 mL) and H$_2$O (5.9 mL) from 0° C. to 23° C. for 1 h.] (2.4 g, 5.46 mmol) by reduction with SnCl$_2$.2H$_2$O according to the general procedure J (method b). Obtained as a yellow solid (2.15 g).

MS (ISP) 410.3 [(M+H)$^+$]; mp 161–164° C.

Example J9

(2-Amino-5-methoxy-4-trifluoromethyl-phenyl)-carbamic Acid tert.-Butyl Ester

The title compound was prepared from (5-methoxy-2-nitro-4-trifluoromethyl-phenyl)-carbamic acid tert.-butyl ester (Example A7) (5.79 g, 17.2 mmol) by hydrogenation with 10% Pd/C according to the general procedure J (method a). Obtained as a yellow solid (5.36 g).

MS (ISP) 307 [(M+H)$^+$]; mp 125° C.

Example J10

(2-Amino-5-fluoro-4-trifluoromethyl-phenyl)-carbamic Acid tert.-Butyl Ester

The title compound was prepared from (5-fluoro-2-nitro-4-trifluoromethyl-phenyl)-carbamic acid tert.-butyl ester (Example A8) (3.34 g, 10.3 mmol) by hydrogenation with 10% Pd/C according to the general procedure J (method a). Obtained as a yellow solid (2.93 g).

MS (ISP) 295 [(M+H)$^+$]; mp 107–109° C.

Example J11

(2-Amino-5-ethoxy-4-trifluoromethyl-phenyl)-carbamic Acid tert.-Butyl Ester

The title compound was prepared from (5-ethoxy-2-nitro-4-trifluoromethyl-phenyl)-carbamic acid tert.-butyl ester (Example A9) (5.52 g, 15.8 mmol) by hydrogenation with 10% Pd/C according to the general procedure J (method a). Obtained as a yellow solid (3.84 g).

MS (ISP) 321 [(M+H)$^+$]; mp 53° C.

Example J12

(2-Amino-4-cyano-5-morpholin-4-yl-phenyl)-carbamic Acid tert-Butyl Ester

The title compound was prepared from (4-cyano-5-morpholin-4-yl-2-nitro-phenyl)-carbamic acid tert-butyl ester (Example B3) (5.01 g, 14.4 mmol) by reduction with $SnCl_2.2H_2O$ according to the general procedure J (method b). Obtained as a pink solid (4.18 g, 91%).

MS (ISP) 319.4 [(M+H)$^+$]; mp 153° C.

Example J13

(2-Amino-4-cyano-5-thiomorpholin-4-yl-phenyl)-carbamic Acid tert-Butyl Ester The title compound was prepared from (4-cyano-2-nitro-5-thiomorpholin-4-yl-phenyl)-carbamic acid tert-butyl ester (Example B4) (2.08 g, 5.71 mmol) by reduction with $SnCl_2.2H_2O$ according to the general procedure J (method b). Obtained as an off-white solid (1.83 g, 96%).

MS (ISP) 335.4 [(M+H)$^+$]; mp 169° C.

Example J14

(2-Amino-5-chloro-4-trifluoromethyl-phenyl)-carbamic Acid tert-Butyl Ester

The title compound was prepared from (5-chloro-2-nitro-4-trifluoromethyl-phenyl)-carbamic acid tert-butyl ester (Example A11) (7.00 g, 20.5 mmol) by reduction with $SnCl_2.2H_2O$ according to the general procedure J (method b). Obtained as a yellow solid (3.13 g, 49%).

MS (ISP) 309.3 [(M−H)$^−$]; mp 170° C.

Example J15

(2-Amino-5-methyl-4-trifluoromethyl-phenyl)-carbamic Acid tert-Butyl Ester

The title compound was prepared from (5-methyl-2-nitro-4-trifluoromethyl-phenyl)-carbamic acid tert-butyl ester (Example B5) (3.40 g, 10.6 mmol) by hydrogenation with 10% Pd/C according to the general procedure J (method a). Obtained as light gray solid (3.0 g, 97%).

MS (ISP) 291.2 [(M+H)$^+$]; mp 174° C.

The following examples relate to the preparation of the ethyl or tert.-butyl 3-aryl-3-oxo-propionates (formula IVa), which serve as building blocks in the synthesis of the target compounds (Synthetic Scheme K):

General Procedure K
Method a) Preparation of Ethyl or tert.-Butyl 3-Aryl-3-oxo-propionates The ethyl or tert.-butyl 3-aryl-3-oxo-propionates were prepared from the aryl acid chlorides and ethyl or tert.-butyl malonate potassium salt [CAS-no. 6148-64-7 and 75486-33-8] with Et$_3$N and MgCl$_2$ in CH$_3$CN at 0° C. to 23° C. according to *Synthesis* 1993, 290. If the free aryl carboxylic acid was employed in this reaction, it was activated by treatment with ethyl chloroformate and Et$_3$N in THF/CH$_3$CN at 0° C. prior to reaction with the malonate salt.

Method b) Preparation of tert.-Butyl 3-Aryl-3-oxo-propionates

The tert.-butyl 3-aryl-3-oxo-propionates were alternatively prepared from the methyl or ethyl aryl esters by treatment with lithium tert.-butyl acetate [prepared by treatment of tert.-butyl acetate with lithium diisopropylamide in THF at −78° C.] in the presence of lithium tert.-butoxide according to *Synthesis* 1985, 45. If the product contained residual starting material after workup, thus could be removed by selective saponification with LiOH in THF/MeOH/H$_2$O at 23° C.

Method c) Preparation of 3-Aryl-3-oxo-propionic Acids

The 3-aryl-3-oxo-propionic acids were prepared from the aryl acid chlorides and bis(trimethylsilyl)malonate with Et$_3$N and LiBr in CH$_3$CN at 0° C. according to *Synth. Commun.* 1985, 15, 1039 (method c1) or with n-BuLi in ether at −60° C. to 0° C. according to *Synthesis* 1979, 787 (method c2).

Example K1

3-oxo-3-(3-[1,2,3]Triazol-1-yl-phenyl)-propionic Acid Ethyl Ester

The title compound was prepared from 3-[1,2,3]triazol-1-yl-benzoic acid, prepared by refluxing of methyl 3-azidobenzoate [CAS-No. 93066-93-4] in trimethylsilylacetylene, followed by saponification with aqueous NaOH in refluxing EtOH] by activation with ethyl chloroformate/Et$_3$N and reaction with ethyl malonate potassium salt with Et$_3$N and MgCl$_2$ in CH$_3$CN according to general procedure K (method a). Obtained as a light yellow solid (2.22 g).

MS (EI) 259 (M$^+$); mp 72–74° C.

Example K2

3-(3-Cyano-phenyl)-3-oxo-propionic Acid tert.-Butyl Ester

The title compound was prepared from methyl 3-cyanobenzoate [CAS-No. 13531-48-1] by treatment with lithium tert.-butyl acetate according to general procedure K (method b). Obtained as a light brown oily semisolid.

MS (EI) 245 (M$^+$).

Example K3

3-(2-Cyano-pyridin-4-yl)-3-oxo-propionic Acid tert.-Butyl Ester

The title compound was prepared from 2-cyano-isonicotinic acid ethyl ester [CAS-No. 58481-14-4] by treatment with lithium tert.-butyl acetate according to general procedure K (method b). Obtained as a light brown solid (7.70 g).

MS (ISN) 245 [(M−H)$^−$].

Example K4

3-[3-(3-Methyl-isoxazol-5-yl)-phenyl]-3-oxo-propionic Acid tert.-Butyl Ester The title compound was prepared from ethyl 3-(3-methyl-isoxazol-5-yl)-benzoate [prepared by reaction of ethyl 3-ethynylbenzoate [CAS-No. 178742-95-5] with a mixture of NCS, acetaldoxime, Et$_3$N and cat. amount of pyridine in CHCl$_3$ at 50° C. according to *Tetrahedron* 1984, 40, 2985–2988] by treatment with lithium tert.-butyl acetate according to general procedure K (method b). Obtained as a yellow solid (2.54 g).

MS (ISP) 302 [(M+H)$^+$]; mp 50–56° C.

Example K5

(RS)-3-oxo-3-{3-[5-(Tetrahydro-pyran-2-yloxymethyl)-[1,2,3]triazol-1-yl]-phenyl}-propionic Acid tert.-Butyl Ester The title compound was prepared from (RS)-3-[5-(tetrahydro-pyran-2-yloxymethyl)-[1,2,3]triazol-1-yl]- benzoic acid methyl ester [prepared by the following sequence: i.) methyl 3-azidobenzoate [CAS-No. 93066-93-4] (15.55 g, 88 mmol) and (RS)-tert.-butyl-dimethyl-[3-(tetrahydro-pyran-2-yloxy)-prop-1-ynyl]-silane [CAS-No. 135294-85-8] (33.50 g, 132 mmol) were heated to 60° C. for 10 days; ii.) The obtained material (48.2 g, ca. 88 mmol) was stirred in TBAF (300 mL, 1M in THF) at 70° C. for 6 days and subsequently refluxed in N HCl (400 mL) for 2 h; iii.) The obtained material (16.15 g, 74 mmol) was stirred in MeOH (400 mL) and conc. H2SO4 (30 mL) at 23° C. for 11 days. iv.) Part of the obtained material (4.60 g, 19.7 mmol) was reacted with 3,4-dihydro-2H-pyran (2.67 mL, 29.5 mmol) and cat. amount p-TsOH.H$_2$O in DCM (38 mL) at 23° C. for 20 h.] (6.20 g, 19.5 mmol) by treatment with lithium tert.-butyl acetate according to general procedure K (method b). Obtained as a yellow oil (8.47 g).

MS (ISP) 402 [(M+H)$^+$].

Example K6

3-[2-(3-Methyl-isoxazol-5-yl)-pyridin-4-yl]-3-oxo-propionic Acid tert.-Butyl Ester The title compound was prepared from 2-(3-methyl-isoxazol-5-yl)-isonicotinic acid methyl ester [prepared by i.) reaction of 2-iodo-isonicotinic acid methyl ester [CAS-No. 134579-47-8] with trimethylsilylacetylene according to general procedure H; ii.) desilylation by reaction with cat. K$_2$CO$_3$ in MeOH at 0° C. for 4 h; iii.) cycloadditon with a mixture of NCS, acetaldoxime, Et$_3$N and cat. amount of pyridine in CHCl$_3$ at 50° C. according to *Tetrahedron* 1984, 40, 2985–2988] by treatment with lithium tert.-butyl acetate according to general procedure K (method b). Obtained as a brown solid (5.17 g). MS (EI) 302 (M$^+$); $^{mp}$ 59–67° C.

Example K7

3-[3-(2-Methyl-2H-pyrazol-3-yl)-phenyl]-3-oxo-propionic Acid tert.-Butyl Ester

The title compound was prepared from 3-(2-methyl-2H-pyrazol-3-yl)-benzoic acid methyl ester [prepared by i.) reaction of 1-(3-bromo-phenyl)-3-dimethylamino-propenone [CAS-No. 163852-04-8] with methylhydrazine in EtOH at 23° C. for 2.5 days; ii.) chromatographic separation of the obtained isomers; iii.) treatment of the clean isomer with n-BuLi in THF at −78° C. for 1 h, followed by quenching with a stream of CO$_2$ and subsequent esterification with MeOH and conc. H$_2$SO$_4$ at 23° C. for 48 h.] by treatment with lithium tert.-butyl acetate according to general procedure K (method b). Obtained as a yellow oil (5.96 g).

MS (EI) 300 (M$^+$).

Example K8

3-[3-(5-Dimethylaminomethyl-[1,2,3]triazol-1-yl)-phenyl]-3-oxo-propionic Acid tert.-Butyl Ester The title compound was prepared from 3-(5-dimethylaminomethyl-[1,2,3]triazol-1-yl)-benzoic acid methyl ester [prepared from methyl 3-azidobenzoate following the synthetic steps i.) to iii.) as described in the preparation of Example K5 and reacting the obtained product with SOCl$_2$ in THF at 0 to 23° C. for 1 h, followed by addition of dimethylamine (7.9 M in H$_2$O) and stirring at 23 to 70° C. for 1 h.] (2.14 g, 8.22 mmol) by treatment with lithium tert.-butyl acetate according to general procedure K (method b). Obtained as a yellow oil (2.90 g).

MS (ISP) 345 [(M+H)$^+$].

Example K9

3-[3-(3-Methoxymethyl-isoxazol-5-yl)-phenyl]-3-oxo-propionic Acid tert.-Butyl Ester The title compound was prepared from methyl 3-(3-methoxymethyl-isoxazol-5-yl)-benzoate [prepared by reaction of ethyl 3-ethynylbenzoate [CAS-No. 178742-95-5] with a mixture of NCS, 2-methoxyacetaldoxime [CAS-No. 71494-93-4], Et$_3$N and cat. amount of pyridine in CHCl$_3$ at 50° C. according to *Tetrahedron* 1984, 40, 2985–2988] by treatment with lithium tert.-butyl acetate according to general procedure K (method b). Obtained as a light yellow liquid (1.548 g).

MS (EI) 331 (M$^+$).

Example K10

(RS)-3-oxo-3-{3-[3-(Tetrahydro-pyran-2-yloxymethyl)-isoxazol-5-yl]-phenyl}-propionic Acid tert.-Butyl Ester The title compound was prepared from (RS)-3-[3-(tetrahydro-pyran-2-yloxymethyl)-isoxazol-5-yl]-benzoic acid methyl ester [prepared by the following sequence: i.) 4-(3-bromo-phenyl)-2,4-dioxo-butyric acid ethyl ester [CAS-No. 151646-31-0] (7.55 g, 23 mmol) and hydroxylamine hydrochloride (4.74 g, 68 mmol) were refluxed in EtOH for 1 h; ii.) The obtained ester (5.94 g, 20 mmol) was reduced with LiAlH$_4$ (761 mg, 20 mmol) in THF at −10° C. for 1 h; iii.) The obtained alcohol (4.90 g, 19 mmol) was reacted with 3,4-dihydro-2H-pyran and cat. amount p-TsOH.H$_2$O in DCM at 23° C. for 20 h. iv.) The obtained THP-ether (5.24 g, 15 mmol) was treated with n-BuLi at −78° C. for 45 min, followed by a stream of CO$_2$. v.) The obtained crude acid was stirred in MeOH (90 mL) and conc. H$_2$SO$_4$ (6.5 mL) at 50° C. for 12 h. vi.) The obtained material (2.01 g, 8.62 mmol) was reacted with 3,4-dihydro-2H-pyran (1.17 mL, 12.9 mmol) and cat. amount p-TsOH.H$_2$O in DCM (17 mL) at 23° C. for 5 h.] (2.44 g, 7.7 mmol) by treatment with lithium tert.-butyl acetate according to general procedure K (method b). Obtained as a yellow oil (3.06 g).

MS (ISP) 402 [(M+H)$^+$].

Example K11

(RS)-3-oxo-3-{3-[5-(Tetrahydro-pyran-2-yloxymethyl)-isoxazol-3-yl]-phenyl}-propionic Acid tert.-Butyl Ester The title compound was prepared from (RS)-3-[5-(tetrahydro-pyran-2-yloxymethyl)-isoxazol-3-yl]-benzoic acid methyl ester [prepared from (Z)-3-(hydroxyimino-methyl)-benzoic acid methyl ester [CAS-No. 91186-80-0] by treatment with NCS, cat. amount pyridine in CHCl$_3$ followed by addition of (RS)-tetrahydro-2-(2-propynyloxy)-2H-pyran and slow addition of Et$_3$N in CHCl$_3$ at 23° C.] by treatment with lithium tert.-butyl acetate according to general procedure K (method b). Obtained as a yellow oil (3.00 g).

MS (ISN) 400.5 [(M−H)$^-$].

Example K12

3-oxo-3-(3-Pyrazol-1-yl-phenyl)-propionic Acid tert.-Butyl Ester

The title compound was prepared from 3-pyrazol-1-yl-benzoic acid methyl ester [CAS-No. 168618-35-7] by treatment with lithium tert.-butyl acetate according to general procedure K (method b). Obtained as a yellow oil (5.00 g).

MS (EI) 286 (M+).

Example K13

3-oxo-3-(3-[1,2,3]Triazol-1-yl-phenyl)-propionic Acid tert.-Butyl Ester

The title compound was prepared from 3-[1,2,3]triazol-1-yl-benzoic acid [prepared by refluxing of methyl 3-azidobenzoate [CAS-No. 93066-93-4] in trimethylsilylacetylene, followed by saponification with aqueous NaOH in refluxing EtOH] (10.0 g, 52.86 mmol) by activation with ethyl chloroformate/Et$_3$N and reaction with mono tert.-butyl malonate potassium salt with Et$_3$N and MgCl$_2$ in CH$_3$CN according to general procedure K (method a). Obtained as an orange oil (11.55 g).

MS (ISP) 288 [(M+H)+].

Example K14

(RS)-3-oxo-3-{3-[5-(Tetrahydro-pyran-2-yloxymethyl)-[1,2,4]triazol-1-yl]-phenyl}-propionic Acid tert.-Butyl Ester The title compound was prepared from (RS)-3-[5-(tetrahydro-pyran-2-yloxymethyl)-[1,2,4]triazol-1-yl]-benzoic acid methyl ester [prepared by the following sequence: i.) methyl 3-(1H-1,2,4-triazol-1-yl)-benzoate, [CAS-No. 167626-27-9] (39.4 g, 194 mmol) was heated in 36% formaldehyde-water (250 ml) in an autoclave for 41 h at 150° C. Cristallisation from water and ethyl acetate/hexane (1:1) yielded a light brown solid (24.3 g, 54%) mp 164° C.; ii.) The obtained material (24.3 g, 104 mmol) was reacted with 3,4-dihydro-2H-pyran (29.3 mL, 320 mmol) and cat. amount p-TsOH.H$_2$O in dichloromethane (360 mL)/THF (300 ml) at 23° C. for 20 h. Purification by column chromatography on silica gel (toluene/ethyl acetate 1:1) gave a light brown oil.] (16.6 g, 52.3 mmol) by treatment with lithium tert.-butyl acetate according to general procedure K (method b). Obtained as a light yellow oil (14.3 g, 68%).

MS (ISP) 400.4 [(M–H)−].

Example K15

3-oxo-3-(3-[1,2,4]Triazol-1-yl-phenyl)-propionic Acid tert-Butyl Ester

The title compound was prepared from methyl 3-[1,2,4]triazol-1-yl-benzoate [CAS-No. 167626-27-9] by treatment with lithium tert.-butyl acetate according to general procedure K (method b). Obtained as an orange liquid (2.41 g).

MS (EI) 287 (M+).

Example K16

3-(3-Imidazol-1-yl-phenyl)-3-oxo-propionic Acid tert-Butyl Ester

The title compound was prepared from methyl 3-(1H-imidazol-1-yl)benzoate [prepared from 3-(1H-imidazol-1-yl)benzoic acid (*J. Med. Chem.* 1987, 30, 1342; CAS-No. [108035-47-8] by refluxing in conc. H$_2$SO$_4$/MeOH] by treatment with lithium tert.-butyl acetate according to general procedure K (method b). Obtained as an orange-brown oil.

MS (ISP) 287 [(M+H)+].

Example K17

3-oxo-[3-[(5-Methyl-oxazol-4-yl)-phenyl]-propionic Acid tert.-Butyl Ester

Methyl 3-(2-Bromo-propionyl)-benzoate

Bromine (4.6 ml) was dropped at 20–30° C. over 20 min. to a solution of methyl 3-propionyl-benzoate (17.24 g) in diethyl ether (0.15 L). Stirring was continued for 10 min. and the reaction mixture was then evaporated in vacuum to give methyl 3-(2-bromo-propionyl)-benzoate (25.5 g) as a yellow oil.

Methyl 3-[5-Methyl-oxazol-4-yl]-benzoate

A mixture of methyl 3-(2-bromo-propionyl)-benzoate (5.42 g) and formamide (3.6 ml) was heated to 130° C. for 5 h. The mixture was cooled and partitioned between H$_2$O and AcOEt. The organic layer was dried over Na$_2$SO$_4$ and evaporated and the residue was purified by chromatography on silica gel (AcOEt/hexane 1:4 as eluent) to give 1.8 g methyl 3-[5-methyl-oxazol-4-yl]-benzoate as white solid.

3-([5-Methyl-oxazol-4-yl]-phenyl)-3-oxo-propionic Acid tert.-Butyl Ester

Methyl 3-[5-methyl-oxazol-4-yl]-benzoate was treated with lithium tert.-butyl acetate according to the general procedure K (method b) to give 3-([5-methyl-oxazol-4-yl]-phenyl)-3-oxo-propionic acid tert.-butyl ester as a pale-yellow oil.

Example K18

Methyl 3-[2-Hydroxymethyl-5-methyl-thiazol-4-yl]-benzoate

A solution of methyl 3-(2-bromo-propionyl)-benzoate (2.7 g) and 2-(tert.-butyl-carbonyloxy)thioacetamide (2.1 g) in EtOH (20 mL) was heated at reflux for 8 h. The mixture was partitioned between H$_2$O and AcOEt. The organic layer was dried and evaporated. The residue was dissolved in MeOH (20 ml), NaOMe (0.54 g) was added, and the mixture was heated to 60° C. for 1 h. The mixture was diluted with AcOEt and then washed with 3N HCl and brine. The organic layer was dried and evaporated and the residue was crystallized from AcOEt to give methyl 3-[2-hydroxymethyl-5-methyl-thiazol-4-yl]-benzoate (1.17 g) as white solid.

Methyl 3-[5-Methyl-2-(tetrahydro-pyran-2-yloxymethyl)-thiazol-4-yl]-benzoate

A mixture of the above material (1.1 g), dihydropyrane (0.73 mL) and p-toluenesulfonic acid hydrate (0.08 g) in AcOEt (10 mL) was stirred at 20° C. for 20 h. The solution was diluted with AcOEt, washed with 5% NaHCO$_3$ solution and with brine, dried and evaporated in vacuum. The residual oil was purified by chromatography on silica gel using AcOEt/hexane (1:3) as eluent to give methyl 3-[5-methyl-2-(tetrahydro-pyran-2-yloxymethyl)-thiazol-4-yl]-benzoate (1.65 g) as a pale-yellow oil.

3-oxo-3-[3-[5-Methyl-2-(tetrahydro-pyran-2-yloxymethyl)-thiazol-4-yl]-phenyl]-propionic Acid tert.-Butyl Ester The above material was treated with lithium tert.-butyl acetate according to general procedure K (method b) to give 3-oxo-3-[3-[5-methyl-2-(tetrahydro-pyran-2-yloxymethyl)-thiazol-4-yl]-phenyl]-propionic acid tert.-butyl ester as a pale-yellow oil.

Example K19

3-oxo-3-[3-[4-(Tetrahydro-pyran-2-yloxymethyl)-thiazol-2-yl]-phenyl]-propionic Acid tert-Butyl Ester

3-(4-Hydroxymethyl-thiazol-2-yl)-benzoic Acid Methyl Ester

A mixture of 3-thiocarbamoyl-benzoic acid methyl ester (7.8 g), 1,3-dichloro-2-propanone (8.4 g) and NaHCO$_3$ (8.4 g) in 1,4-dioxane (180 mL) was heated to 60° C. for 24 h. The reaction mixture was cooled to 20° C. and added to a stirred solution of NaOMe (5.4 g) in MeOH (200 mL). Stirring was continued for 0.5 h. The mixture was poured into ice-cold 2N HCl (200 mL) and the product was extracted with AcOEt. The organic layer was washed with brine, dried and evaporated in vacuum. The residue was crystallized from CH$_2$Cl$_2$/hexane to give 3-(4-hydroxymethyl-thiazol-2-yl)-benzoic acid methyl ester (7.5 g) as light-brown crystals.

3-[4-(Tetrahydro-pyran-2-yloxymethyl)-thiazol-2-yl]-benzoic Acid Methyl Ester

A mixture of the above material (7.5 g), dihydropyrane (4.1 mL) and p-toluenesulfonic acid hydrate (0.19 g) in AcOEt (50 mL) was stirred at 20° C. for 1 h. The solution was diluted with AcOEt, washed with 5% NaHCO$_3$ solution and with brine, dried over Na$_2$SO$_4$ and evaporated in vacuum. The residual oil was purified by chromatography on silica gel using AcOEt/hexane (1:2) as eluent to give 3-[4-(tetrahydro-pyran-2-yloxymethyl)-thiazol-2-yl]-benzoic acid methyl ester (9.6 g) as a pale-yellow oil.

3-oxo-3-[3-[4-(Tetrahydro-pyran-2-yloxymethyl)-thiazol-2-yl]-phenyl]-propionic Acid tert-Butyl Ester A sample of the above material (3.3 g) was treated with lithium tert.-butyl acetate according to general procedure K (method b) to give 3-oxo-3-[3-[4-(tetrahydro-pyran-2-yloxymethyl)-thiazol-2-yl]-phenyl]-propionic acid tert-butyl ester (3.25 g) as a pale-yellow oil.

MS (ISP) 418.2 [(M+H)$^+$].

The following examples relate to the preparation of the 6-aryl-2,2-dimethyl-[1,3]dioxin-4-ones (formula IV), which serve as building blocks in the synthesis of the target compounds (Synthetic Scheme K):

General Procedure L

Preparation of 6-Aryl-2,2-dimethyl-[1,3]dioxin-4-ones

Method a)

The 6-aryl-2,2-dimethyl-[1,3]dioxin-4-ones were prepared from 3-aryl-3-oxo-propionic acids and catalytic amount of conc. H$_2$SO$_4$ or trifluoroacetic acid (TFA) in isopropenyl acetate at 23° C. according to *Chem. Pharm. Bull.* 1983, 31, 1896.

The final products were purified by silica gel column chromatography with hexane/EtOAc.

Method b)

The 6-aryl-2,2-dimethyl-[1,3]dioxin-4-ones were prepared from the tert.-butyl 3-aryl-3-oxo-propionates by treatment with trifluoroacetic anhydride (TFAA) in a mixture of TFA and acetone at 23° C. according to *Tetrahedron Lett.* 1998, 39, 2253. The final products were if necessary purified by silica gel column chromatography with hexane/EtOAc.

Example L1

3-(2,2-Dimethyl-6-oxo-6H-[1,3]dioxin-4-yl)-benzonitrile

The 3-(3-cyano-phenyl)-3-oxo-propionic acid was prepared from 3-cyanobenzoyl chloride (828 mg, 5 mmol) and bis(trimethylsilyl)malonate (2.56 mL, 10 mmol) with n-BuLi (1.6M in hexane, 6.25 mL) in ether at −60° C. to 0° C. according to general procedure K (method c2). The crude material (1.04 g) was transformed into the title compound by stirring in isopropenyl acetate and TFA according to general procedure L (method a). Obtained as a light yellow solid (0.8 g).

MS (EI) 229 (M$^+$); mp 138° C. (dec.).

Example L2

4-(2,2-Dimethyl-6-oxo-6H-[1,3]dioxin-4-yl)-pyridine-2-carbonitrile

The title compound was prepared from 3-(2-cyano-pyridin-4-yl)-3-oxo-propionic acid tert.-butyl ester (Example M10) by stirring in TFA/acetone with TFAA according to general procedure L (method b). Obtained as a brown solid (3.30 g).

MS (EI) 230 (M$^+$); mp 132° C. (dec.).

Example L3

6-(3-Imidazol-1-yl-phenyl)-2,2-dimethyl-[1,3]dioxin-4-one

The 3-(3-imidazol-1-yl-phenyl)-3-oxo-propionic acid was prepared from 3-(1H-imidazol-1-yl)benzoyl chloride hydrochloride [prepared by treatment of 3-(1H-imidazol-1-yl)-benzoic acid (*J. Med. Chem.* 1987,30, 1342; CAS-No. [108035-47-8] with SOCl$_2$) and bis(trimethylsilyl)malonate with Et$_3$N and LiBr in CH$_3$CN at 0° C. according to general procedure K (method c1). The crude material was transformed into the title compound by stirring in isopropenyl acetate and conc. H$_2$SO$_4$ according to general procedure L (method a). Obtained as an orange semisolid (617 mg).

MS (EI) 270 (M$^+$).

Example L4

6-(3-Iodo-phenyl)-2,2-dimethyl-[1,3]dioxin-4-one

The 3-(3-iodo-phenyl)-3-oxo-propionic acid was prepared from 3-iodobenzoyl chloride (21.0 g, 78.8 mmol) and bis(trimethylsilyl)malonate (21.0 mL, 82.8 mmol) with Et$_3$N (23 mL, 165.5 mmol) and LiBr (7.54 g, 86.7 mmol) in CH$_3$CN at 0° C. according to general procedure K (method c1). The crude material (21.9 g) was transformed into the title compound by stirring in isopropenyl acetate and conc. H$_2$SO$_4$ according to general procedure L (method a). Obtained as a yellow solid (9.6 g).

MS (EI) 330 (M$^+$); mp 79–80° C. (dec.).

Example L5

2,2-Dimethyl-6-(3-oxazol-2-yl-phenyl)-[1,3]dioxin-4-one

The 3-(3-oxazol-2-yl-phenyl)-3-oxo-propionic acid was prepared from 3-oxazol-2-yl-benzoyl chloride [prepared by the following sequence: i.) To a solution of isophthalic acid monomethyl ester (5.83 g) in DMF (150 mL) were added at −35° C. 88% 1-hydroxy-benzotriazole (7.83 g) and N-(3-dimethylaminopropyl)-N'-ethylcarbodiimide hydrochloride (9.78 g) and the mixture was stirred for 10 min. A solution of amino-acetaldehyde dimethylacetal (4.53 mL) in DMF (30 mL) was added dropwise over 10 min. The mixture was allowed to warm up to 0° C. over 2 h, diluted with H$_2$O and extracted with EtOAc. The organic layer was washed successively with 5% aqueous citric acid, sat. NaHCO$_3$-solution and brine, dried over Na$_2$SO$_4$ and evaporated in vacuum to give 3-[N-(2,2-dimethoxy-ethyl)-aminocarbonyl]-benzoic acid methyl ester (8.2 g) as an oil. ii.) To a solution of this material (5.4 g) in THF (40 mL) was added 6N HCl (10 mL). After being stirred 20° C. for 2 h, the mixture was partitioned between EtOAc and brine. The organic layer was dried and evaporated to give 3-[N-(2-oxo-ethyl)-aminocarbonyl]-benzoic acid methyl ester (4.0 g) as an oil. iii.) A solution of this material (4.0 g) in dichloromethane (35 mL) was added at 20° C. to a solution of iodine (9.1 g) and triphenylphosphine (9.4 g) in dichloromethane (350 mL). The brown solution was stirred at 20° C. for 0.5 h and subsequently washed with 0.1M sodium thiosulfate solution and H$_2$O, dried over Na$_2$SO$_4$ and evaporated to give 3-oxazol-2-yl-benzoic acid methyl ester (1.05 g) as light-brown solid, mp. 64–70° C. iv.) A mixture of this material (0.41 g), EtOH (4 mL) and 2N KOH (2 mL) was heated to 80° C. for 1.5 h. The solution was diluted with H$_2$O and washed with diethylether. The aqueous layer was acidified with 3N HCl and the product was extracted with EtOAc to give 3-oxazol-2-yl-benzoic acid (0.28 g) as a light-brown solid, mp. 187–188° C. v.) This carboxylic acid (4.2 g) was heated with thionyl chloride in toluene and the resulting carboxylic acid chloride was used directly in the next step.] (4.4 g) and bis(trimethylsilyl)malonate with n-BuLi in ether at −60° C. to 0° C. according to general procedure K (method c2). The crude material was transformed into the title compound by stirring in isopropenyl acetate and conc. H$_2$SO$_4$ according to general procedure L (method a). Obtained as pale-yellow crystals (1.8 g).

MS (EI) 271 (M$^+$); mp 115–119° C. (dec.).

Example L6

5-[3-(2,2-Dimethyl-6-oxo-6H-[1,3]dioxin-4-yl)-phenyl]-oxazole-4-carboxylic Acid Ethyl Ester The 5-(3-carboxyacetyl-phenyl)-oxazole-4-carboxylic acid ethyl ester was prepared from 5-(3-chlorocarbonyl-phenyl)-oxazole-4-carboxylic acid ethyl ester [prepared by the following sequence: i.) A mixture of isophthalic acid monoallyl ester (8.2 g), thionyl chloride (4.4 mL) and DMF (0.1 mL) in toluene (50 mL) was heated to 90° C. for 2 h. The mixture was evaporated in vacuum to give 3-chlorocarbonyl-benzoic acid allyl ester (9.0 g) as a light-yellow oil. ii.) To a solution of this material (9.0 g) and isocyano-acetic acid ethyl ester (4.4 mL) in THF (60 mL) was added at 0° C. Et$_3$N (14.0 mL). The mixture was stirred at 20° C. for 2.5 h and then evaporated in vacuum. The residue was partitioned between EtOAc and brine and the organic layer was dried and evaporated in vacuum. The residual oil was chromatographed on silica gel using EtOAc/hexane as eluent to give 5-(3-allyloxycarbonyl-phenyl)-oxazole-4-carboxylic acid ethyl ester (6.9 g) as a pale-yellow oil. iii.) This material (6.9 g) was subjected to the palladium-catalysed allylester cleavage according to general procedure G (method b) to give 5-(3-carboxy-phenyl)-oxazole-4-carboxylic acid ethyl ester (6.9 g) as light brown crystals, mp 190–192° C. iv.) This carboxylic acid (2.6 g) was heated with thionyl chloride in toluene and the resulting carboxylic acid chloride was used directly in the next step.] (2.8 g) and bis(trimethylsilyl)malonate with n-BuLi in ether at −60° C. to 0° C. according to general procedure K (method c2). The crude material was transformed into the title compound by stirring in isopropenyl acetate and conc. H$_2$SO$_4$ according to general procedure L (method a). Obtained as pale-yellow crystals (1.4 g).

MS (EI) 343 (M$^+$); mp 131–132° C. (dec.).

Example L7

2-[3-(2,2-Dimethyl-6-oxo-6H-[1,3]dioxin-4-yl)-phenyl]-oxazole-4-carboxylic Acid Methyl Ester The 2-(3-carboxyacetyl-phenyl)-oxazole-4-carboxylic acid methyl ester was prepared from 2-(3-chlorocarbonyl-phenyl)-oxazole-4-carboxylic acid methyl ester [prepared by the following sequence: i.) To a solution of isophthalic acid (16.6 g) and 1,1,3,3-tetramethyl-guanidine (27.7 mL) in DMSO (75 mL) was added at 0° C. allyl bromide (18.6 mL) and the mixture was stirred at 20° C. for 6 h. The mixture was diluted with EtOAc and washed with 2N HCl and brine. The organic layer was dried and evaporated. The remaining oil (21.5 g) was dissolved in DMSO (40 mL) and, after the addition of LiOH hydrate (2.8 g) and H$_2$O (1 mL), the mixture was heated to 60° C. for 3 h. The solution was diluted with EtOAc and then extracted with 5% NaHCO$_3$-solution. The aqueous layer was acidified with 25% HCl and the precipitated product was extracted with EtOAc to give isophthalic acid monoallyl ester (23.1 g) as white crystals. ii.) To a solution of this material (15.5 g) in DMF (350 mL) were added at −35° C. 88% 1-hydroxy-benzotriazole (15.4 g) and N-(3-dimethylaminopropyl)-N'-ethylcarbodiimide hydrochloride (19.2 g) and the mixture was stirred for 30 min. L-Serine methyl ester hydrochloride (14.0 g) was added at −50° C. followed by the addition of a solution of NEt$_3$ (12.5 mL) in DMF (50 mL) over 2 min. The mixture was allowed to warm up to 20° C. over 2 h and stirring was continued for 19 h. The mixture was diluted with H$_2$O and extracted with EtOAc. The organic layer was washed successively with 0.5 N HCl, sat. NaHCO$_3$-solution and brine, dried over Na$_2$SO$_4$ and evaporated in vacuum to give (S)-3-[N-(1-methoxycarbonyl-2-hydroxy)-aminocarbonyl]-benzoic acid allyl ester (20.6 g) as a crystallizing oil. iii.) To a solution of this material (20.6 g) in THF (0.4 L) was added methoxycarbonylsulfamoyl-triethylammonium hydroxide inner salt (17.6 g) and the mixture was stirred at 70° C. for 1 h. The mixture was evaporated in vacuum and the residue was purified by chromatography using EtOAc/hexane (1:1) as eluent to give (S)-2-(3-allyloxycarbonyl-phenyl)-4,5-dihydro-oxazole-4-carboxylic acid methyl ester (16.7 g) as a yellow oil. iv.) To a solution of this material (14.7 g) in a mixture of acetonitrile (75 mL) and pyridine (75 mL) was added at 0° C. CCl$_4$ (14.4 mL) and subsequently DBU (15.0 mL). The mixture was stirred at 20° C. for 0.5 h, diluted with EtOAc and washed with 2N HCl and brine. The organic layer was dried and evaporated to give 2-(3-allyloxycarbonyl-phenyl)-oxazole-4-carboxylic acid methyl ester (10.1 g) as light-brown crystals, mp 104–107° C. v.) This material (10.1 g) was subjected to the palladium-catalysed allylester cleavage according to general procedure G (method b) to give 2-(3-carboxy-phenyl)-oxazole-4-carboxylic acid methyl ester (7.0 g) as light-brown crystals, mp 209–210° C. (dec.). vi.) This carboxylic acid (1.26 g) was heated with thionyl chloride in toluene and the resulting carboxylic acid chloride was used directly in the next step.] (1.35 g) and bis(trimethylsilyl)malonate with n-BuLi in ether at −60° C. to 0° C. according to general procedure K (method c2). The crude material was transformed into the title compound by stirring in isopropenyl acetate and conc. H$_2$SO$_4$ according to general procedure L (method a). Obtained as pale-yellow crystals (1.4 g).

MS (EI) 329 (M$^+$); mp 141–142° C. (dec.).

Example L8

4-[3-(2,2-Dimethyl-6-oxo-6H-[1,3]dioxin-4-yl)-phenyl]-thiazole-2-carboxylic Acid Ethyl Ester The 4-(3-carboxyacetyl-phenyl)-thiazole-2-carboxylic acid ethyl ester was prepared from 4-(3-chlorocarbonylphenyl)-thiazole-2-carboxylic acid ethyl ester [prepared by the following sequence: i.) A mixture of 3-(2-bromo-acetyl)-benzoic acid [CAS-no. 62423-73-8] (2.43 g) and ethyl thiooxamate [CAS-no. 16982-21-1] (1.6 g) in THF (40 mL) was heated to 60° C. for 4 h and then partitioned between EtOAc and brine. The organic layer was dried and evaporated and the residue was crystallized from EtOAc/hexane to give 4-(3-carboxy-phenyl)-thiazole-2-carboxylic acid ethyl ester (2.2 g) as off-white crystals, mp 225–228° C. ii.) This carboxylic acid (2.1 g) was heated with thionyl chloride in toluene and the resulting carboxylic acid chloride was used directly in the next step.] (2.24 g) and bis(trimethylsilyl) malonate with n-BuLi in ether at −60° C. to 0° C. according to general procedure K (method c2). The crude material was transformed into the title compound by stirring in isopropenyl acetate and conc. $H_2SO_4$ according to general procedure L (method a). Obtained as yellow oil (2.7 g).

MS (EI) 359 ($M^+$).

Example L9

2,2-Dimethyl-6-(3-[1,2,3]triazol-1-yl-phenyl)-[1,3]dioxin-4-one

The title compound was prepared from 3-oxo-3-(3-[1,2,3]triazol-1-yl-phenyl)-propionic acid tert.-butyl ester (Example K13) by stirring in TFA/acetone with TFAA according to general procedure L (method b). Obtained as a beige solid (7.80 g).

MS (EI) 271 ($M^+$); mp 144–147° C. (dec.).

General Procedure M

Preparation of {2-[3-Aryl-3-oxo-propionylamino]-phenyl}-carbamic Acid tert.-Butyl Ester by Reaction of (2-Amino-phenyl)-carbamic Acid tert.-Butyl Esters with Ethyl or tert.-Butyl 3-Aryl-3-oxo-propionates or 6-Aryl-2,2-dimethyl-[1,3]dioxin-4-ones A mixture of the (2-amino-phenyl)-carbamic acid tert.-butyl ester or (1.0–1.2 mmol) and (1.0–1.5 mmol) of the ethyl or tert.-butyl 3-aryl-3-oxo-propionate or 6-aryl-2,2-dimethyl-[1,3]dioxin-4-one was heated in toluene (4–8 mL) to 80° C. to 120° C. until tlc indicated complete consumption of the minor component. The solution was allowed to cool to 23° C., whereupon the product generally crystallized (in cases where crystallization failed to appear it was induced by addition of hexane or ether, alternatively the reaction mixture was directly subjected to silica gel column chromatography). The solid was filtered off, washed with ether or mixtures of ether/hexane and dried in vacuum to give the {2-[3-aryl-3-oxo-propionylamino]-phenyl}-carbamic acid tert.-butyl esters, which was used directly in the following step or—if necessary—was purified by recrystallization or by silica gel column chromatography.

Example M1

(RS)-[5-Morpholin-4-yl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (201 mg, 0.5 mmol) according to the general procedure M. Obtained as an amorphous off-white substance (223 mg).

MS (ISP) 689 [$(M+H)^+$].

Example M2

{2-[3-(2-Cyano-pyridin-4-yl)-3-oxo-propionylamino]-5-morpholin-4-yl-4-trifluoromethyl-phenyl}-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and 3-(2-cyano-pyridin-4-yl)-3-oxo-propionic acid tert.-butyl ester (Example K3) (123 mg, 0.5 mmol) according to the general procedure M. Obtained as an off-white solid (137 mg).

MS (ISP) 534 [$(M+H)^+$]; mp 128° C.

Example M3

(2-{3-[3-(3-Methyl-isoxazol-5-yl)-phenyl]-3-oxo-propionylamino}-5-morpholin-4-yl-4-trifluoromethyl-phenyl)-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and 3-[3-(3-methyl-isoxazol-5-yl)-phenyl]-3-oxo-propionic acid tert.-butyl ester (Example K4) (151 mg, 0.5 mmol) according to the general procedure M. Obtained as an amorphous yellow substance (117 mg).

MS (ISP) 589 [$(M+H)^+$].

Example M4

(3-(3-Cyano-phenyl)-N-(2-nitro-5-pyrrol-1-yl-phenyl)-3-oxo-propionamide

The title compound was prepared from 2-nitro-4-pyrrol-1-yl-phenylamine (Example E1) (203 mg, 1.0 mmol) and 3-(2,2-dimethyl-6-oxo-6H-[1,3]dioxin-4-yl)-benzonitrile (Example L1) (309 mg, 1.1 mmol) according to the general procedure M. Obtained as a brown solid (117 mg).

MS (ISN) 373 [$(M-H)^-$]; mp 206° C. (dec.).

Example M5

{2-[3-(3-Cyano-phenyl)-3-oxo-propionylamino]-4-pyrrol-1-yl-phenyl}-carbamic Acid tert-Butyl Ester The title compound was prepared from (2-amino-4-pyrrol-1-yl-phenyl)-carbamic acid tert.-butyl ester (Example J2) (137 mg, 0.5 mmol) and 3-(2,2-dimethyl-6-oxo-6H-[1,3]dioxin-4-yl)-benzonitrile (Example L1) (115 mg, 0.5 mmol) according to the general procedure M. Obtained as a light red solid (139 mg).

MS (ISN) 443 [$(M-H)^-$].

Example M6

N-{5-[3-(2-Chloro-phenyl)-4-cyano-pyrrol-1-yl]-2-nitro-phenyl}-3-(3-cyano-phenyl)-3-oxo-propionamide The title compound was prepared from 1-(3-amino-4-nitro-phenyl)-4-(2-chloro-phenyl)-1H-pyrrole-3- carbonitrile (Example E2) and 3-(2,2-dimethyl-6-oxo-6H-[1,3]dioxin-4-yl)-benzonitrile (Example L1) according to the general procedure M. Obtained as an orange-brown solid (203 mg).

MS (ISN) 508 [(M−H)⁻] and 510 [(M+2−H)⁻]; mp 229–232° C.

Example M7

3-(3-Cyano-phenyl)-N-[5-(3-cyano-4-phenyl-pyrrol-1-yl)-2-nitro-phenyl]-3-oxo-propionamide The title compound was prepared from 1-(3-amino-4-nitro-phenyl)-4-phenyl-1H-pyrrole-3-carbonitrile (Example E3) (254 mg, 0.835 mmol) and 3-(2,2-dimethyl-6-oxo-6H-[1,3]dioxin-4-yl)-benzonitrile (Example L1) (210 mg, 0.919 mmol) according to the general procedure M. Obtained as an orange solid (287 mg).

MS (ISN) 474 [(M−H)⁻].

Example M8

3-(3-Iodo-phenyl)-N-(2-nitro-4-pyrrol-1-yl-phenyl)-3-oxo-propionamide

The title compound was prepared from 2-nitro-4-pyrrol-1-yl-phenylamine (Example E1) (610 mg, 3 mmol) and 6-(3-iodo-phenyl)-2,2-dimethyl-[1,3]dioxin-4-one (Example L4) (1.49 g, 4.5 mmol) according to the general procedure M. Obtained as a brown solid (876 mg).

MS (ISN) 474 [(M−H)⁻]; mp 193–196° C.

Example M9

3-(3-Cyano-phenyl)-N-(4-iodo-2-nitro-5-pyrrol-1-yl-phenyl)-3-oxo-propionamide

The title compound was prepared from 4-iodo-2-nitro-5-pyrrol-1-yl-phenylamine (Example F2) (329 mg, 1.0 mmol) and 3-(2,2-dimethyl-6-oxo-6H-[1,3]dioxin-4-yl)-benzonitrile (Example L1) (252 mg, 1.1 mmol) according to the general procedure M. Obtained as a yellow solid (436 mg).

MS (EI) 500 (M⁺); mp 183° C.

Example M10

[2-[3-(3-Cyano-phenyl)-3-oxo-propionylamino]-5-(2-methoxy-ethoxy)-4-pyrrol-1-yl-phenyl]-carbamic Acid tert.-Butyl Ester The title compound was prepared from [2-amino-5-(2-methoxy-ethoxy)-4-pyrrol-1-yl-phenyl]-carbamic acid tert.-butyl ester (Example J3) (186 mg, 0.54 mmol) and 3-(2,2-dimethyl-6-oxo-6H-[1,3]dioxin-4-yl)-benzonitrile (Example L1) (153 mg, 0.67 mmol) according to the general procedure M. Obtained as a beige solid (179 mg).

MS (EI) 518 (M⁺); mp 102–130° C.

Example M11

3-(3-Cyano-phenyl)-N-[5-(3-hydroxymethyl-pyrrol-1-yl)-2-nitro-phenyl]-3-oxo-propionamide The title compound was prepared from [1-(3-amino-4-nitro-phenyl)-1H-pyrrol-3-yl]-methanol (Example F5) and 3-(2,2-dimethyl-6-oxo-6H-[1,3]dioxin-4-yl)-benzonitrile (Example L1) according to the general procedure M. Obtained as an orange solid (77 mg).

MS (ISN) 403 [(M−H)⁻].

Example M12

3-(3-Cyano-phenyl)-N-[2-nitro-5-(3-phenyl-pyrrol-1-yl)-phenyl]-3-oxo-propionamide The title compound was prepared from 2-nitro-5-(3-phenyl-pyrrol-1-yl)-phenylamine (Example F6) and 3-(2,2-dimethyl-6-oxo-6H-[1,3]dioxin-4-yl)-benzonitrile (Example L1) according to the general procedure M. Obtained as an orange solid (267 mg).

MS (ISN) 449 [(M−H)⁻].

Example M13

3-(3-Cyano-phenyl)-N-[5-(3-methoxymethyl-pyrrol-1-yl)-2-nitro-phenyl]-3-oxo-propionamide The title compound was prepared from 5-(3-methoxymethyl-pyrrol-1-yl)-2-nitro-phenylamine (Example F7) and 3-(2,2-dimethyl-6-oxo-6H-[1,3]dioxin-4-yl)-benzonitrile (Example L1) according to the general procedure M. Obtained as a yellow solid (102 mg).

MS (ISN) 417 [(M−H)⁻].

Example M14

3-(3-Cyano-phenyl)-N-[5-(2-methoxymethyl-pyrrol-1-yl)-2-nitro-phenyl]-3-oxo-propionamide The title compound was prepared from 5-(2-methoxymethyl-pyrrol-1-yl)-2-nitro-phenylamine (Example F8) and 3-(2,2-dimethyl-6-oxo-6H-[1,3]dioxin-4-yl)-benzonitrile (Example L1) according to the general procedure M. Obtained as a light brown solid (620 mg).

MS (ISN) 417 [(M−H)⁻].

Example M15

1-{3-[3-(3-Cyano-phenyl)-3-oxo-propionylamino]-4-nitro-phenyl}-1H-pyrrole-2-carboxylic Acid Methyl Ester The title compound was prepared from 1-(3-amino-4-nitro-phenyl)-1H-pyrrole-2-carboxylic acid methyl ester (Example F9) and 3-(2,2-dimethyl-6-oxo-6H-[1,3]dioxin-4-yl)-benzonitrile (Example L1) according to the general procedure M. Obtained as a yellow solid (840 mg).

MS (ISN) 431 [(M−H)⁻]; mp 161–170° C.

Example M16

3-(3-Imidazol-1-yl-phenyl)-N-(2-nitro-5-pyrrol-1-yl-phenyl)-3-oxo-propionamide

The title compound was prepared from 2-nitro-4-pyrrol-1-yl-phenylamine (Example E1) (163 mg, 0.8 mmol) and 6-(3-imidazol-1-yl-phenyl)-2,2-dimethyl-[1,3]dioxin-4-one (Example L3) (261 mg, 1.0 mmol) according to the general procedure M. Obtained as a dark brown solid (249 mg).

MS (ISP) 416 [(M+H)⁺].

Example M17

{2-[3-(3-Imidazol-1-yl-phenyl)-3-oxo-propionylamino]-4-pyrrol-1-yl-phenyl}-carbamic Acid tert.-Butyl Ester The title compound was prepared from (2-amino-4-pyrrol-1-yl-phenyl)-carbamic acid tert.-butyl ester (Example J2) (1.37 g, 5.0 mmol) and 6-(3-imidazol-1-yl-phenyl)-2,2-dimethyl-[1,3]dioxin-4-one (Example L3) (1.28 g, 4.75 mmol) according to the general procedure M. Obtained as a light brown foam (1.78 g).

MS (ISP) 486 [(M+H)$^+$].

Example M18

{2-[3-(3-Cyano-phenyl)-3-oxo-propionylamino]-5-methoxy-4-pyrrol-1-yl-phenyl}-carbamic Acid tert.-Butyl Ester The title compound was prepared from (2-amino-5-methoxy-4-pyrrol-1-yl-phenyl)-carbamic acid tert.-butyl ester (Example J4) (303 mg, 1.0 mmol) and 3-(2,2-dimethyl-6-oxo-6H-[1,3]dioxin-4-yl)-benzonitrile (Example L1) (252 mg, 1.1 mmol) according to the general procedure M. Obtained as an off-white solid (257 mg).

MS (ISP) 475 [(M+H)$^+$]; mp 190° C.

Example M19

{4-(2-tert.-Butyl-pyrrol-1-yl)-2-[3-(3-cyano-phenyl)-3-oxo-propionylamino]-5-methoxy-phenyl}-carbamic Acid tert.-Butyl Ester The title compound was prepared from [2-amino-4-(2-tert.-butyl-pyrrol-1-yl)-5-methoxy-phenyl]-carbamic acid tert.-butyl ester (Example J5) (89 mg, 0.25 mmol) and 3-(2,2-dimethyl-6-oxo-6H-[1,3]dioxin-4-yl)-benzonitrile (Example L1) (63 mg, 0.275 mmol) according to the general procedure M. Obtained as an off-white solid (72 mg).

MS (ISP) 531 [(M+H)$^+$]; mp 172° C.

Example M20

{2-[3-oxo-3-(3-[1,2,3]Triazol-1-yl-phenyl)-propionylamino]-4-pyrrol-1-yl-phenyl}-carbamic Acid tert.-Butyl Ester The title compound was prepared from (2-amino-4-pyrrol-1-yl-phenyl)-carbamic acid tert.-butyl ester (Example J2) and 3-oxo-3-(3-[1,2,3]triazol-1-yl-phenyl)-propionic acid ethyl ester (Example K1) according to the general procedure M. Obtained as a light yellow solid (140 mg).

MS (ISP) 487 [(M+H)$^+$]; mp 81–84° C.

Example M21

{5-Cyanomethyl-2-[3-(3-imidazol-1-yl-phenyl)-3-oxo-propionylamino]-4-iodo-phenyl}-carbamic Acid tert.-Butyl Ester The title compound was prepared from (2-amino-5-cyanomethyl-4-iodo-phenyl)-carbamic acid tert.-butyl ester (Example J6) (363 mg, 0.973 mmol) and 6-(3-imidazol-1-yl-phenyl)-2,2-dimethyl-[1,3]dioxin-4-one (Example L3) (411 mg, 1.52 mmol) according to the general procedure M. Obtained as a yellow oil (523 mg).

MS (ISP) 586.0 [(M+H)$^+$].

Example M22

(2-{3-[3-(2-Methyl-2H-pyrazol-3-yl)-phenyl]-3-oxo-propionylamino}-5-morpholin-4-yl-4-trifluoromethyl-phenyl)-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and 3-[3-(2-methyl-2H-pyrazol-3-yl)-phenyl]-3-oxo-propionic acid tert.-butyl ester (Example K7) (150 mg, 0.5 mmol) according to the general procedure M. Obtained as an amorphous yellow substance (114 mg).

MS (ISN) 586.0 [(M−H)$^−$].

Example M23

(RS)-[5-Morpholin-4-yl-2-(3-oxo-3-{3-[3-(tetrahydro-pyran-2-yloxymethyl)-isoxazol-yl]-phenyl}-propionylamino)-4-trifluoromethyl-phenyl]-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and (RS)-3-oxo-3-{3-[3-(tetrahydro-pyran-2-yloxymethyl)-isoxazol-5-yl]-phenyl}-propionic acid tert.-butyl ester (Example K10) (201 mg, 0.5 mmol) according to the general procedure M. Obtained as an amorphous yellow substance (57 mg).

MS (ISP) 689.0 [(M+H)$^+$].

Example M24

(2-{3-[3-(5-Dimethylaminomethyl-[1,2,3]triazol-1-yl)-phenyl]-3-oxo-propionylamino}-5-morpholin-4-yl-4-trifluoromethyl-phenyl)-carbamic Acid tert.-Butyl Ester The title compound was prepared from (2-amino-5-morpholin-4-yl-4-trifluoromethyl-phenyl)-carbamic acid tert.-butyl ester (Example J1) (181 mg, 0.5 mmol) and 3-[3-(5-dimethylaminomethyl-[1,2,3]triazol-1-yl)-phenyl]-3-oxo-propionic acid tert.-butyl ester (Example K8) (172 mg, 0.5 mmol) according to the general procedure M. Obtained as an amorphous yellow substance (179 mg).

MS (ISN) 630 [(M−H)$^−$].

Example M25

(2-{3-[3-(3-Methyl-isoxazol-5-yl)-phenyl]-3-oxo-propionylamino}-5-thiomorpholin-4-yl-4-trifluoromethyl-phenyl)-carbamic Acid tert.-Butyl Ester The title compound was prepared from (2-amino-5-thiomorpholin-4-yl-4-trifluoromethyl-phenyl)-carbamic acid tert.-butyl ester (Example J7) (189 mg, 0.5 mmol) and 3-[3-(3-methyl-isoxazol-5-yl)-phenyl]-3-oxo-propionic acid tert.-butyl ester (Example K4) (170 mg, 0.56 mmol) according to the general procedure M. Obtained as a yellow solid (302 mg).

MS (ISN) 603.0 [(M−H)$^−$].

Example M26

{2-[3-(2-Cyano-pyridin-4-yl)-3-oxo-propionylamino]-5-thiomorpholin-4-yl-4-trifluoromethyl-phenyl}-carbamic Acid tert.-Butyl Ester The title compound was prepared from (2-amino-5-thiomorpholin-4-yl-4-trifluoromethyl-phenyl)-carbamic acid tert.-butyl ester (Example J7) (189 mg, 0.5 mmol) and 3-(2-cyano-pyridin-4-yl)-3-oxo-propionic acid tert.-butyl ester (Example K3) (150 mg, 0.61 mmol) according to the general procedure M. Obtained as a yellow solid (273 mg).

MS (ISN) 548.1 [(M−H)$^−$]; mp 53–55° C.

Example M27

(RS)-[5-(1,1-Dioxo-11 6-Thiomorpholin-4-yl)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic Acid tert.-Butyl Ester The title compound was prepared from [2-amino-5-(1,1-dioxo-11 6-thiomorpholin-4-yl)-4-trifluoromethyl-phenyl]-carbamic acid tert.-butyl ester (Example J8) and (RS)-3-oxo-3-{3-[3-(tetrahydro-pyran-2-yloxymethyl)-isoxazol-5-yl]-phenyl}-propionic acid tert.-butyl ester (Example K10) according to the general procedure M. Obtained as a light yellow foam (235 mg).

MS (ISP) 737.2 [(M+H)$^+$].

Example M28

{2-[3-(2-Cyano-pyridin-4-yl)-3-oxo-propionylamino]-5-methoxy-4-trifluoromethyl-phenyl}-carbamic Acid tert.-Butyl Ester The title compound was prepared from (2-amino-5-methoxy-4-trifluoromethyl-phenyl)-carbamic acid tert.-butyl ester (Example J9) (306 mg. 1.0 mmol) and 3-(2-cyano-pyridin-4-yl)-3-oxo-propionic acid tert.-butyl ester (Example K3) (246 mg, 1.0 mmol) according to the general procedure M. Obtained as a yellow solid (333 mg).

MS (ISP) 479 [(M+H)$^+$]; mp 92–119° C.

Example M29

(5-Methoxy-2-{3-[3-(3-methyl-isoxazol-5-yl)-phenyl]-3-oxo-propionylamino}-4-trifluoromethyl-phenyl)-carbamic Acid tert.-Butyl Ester The title compound was prepared from (2-amino-5-methoxy-4-trifluoromethyl-phenyl)-carbamic acid tert.-butyl ester (Example J9) (306 mg. 1.0 mmol) and 3-[3-(3-methyl-isoxazol-5-yl)-phenyl]-3-oxo-propionic acid tert.-butyl ester (Example K4) (301 mg, 1.0 mmol) according to the general procedure M. Obtained as an off-white solid (301 mg).

MS (ISP) 534 [(M+H)$^+$]; mp 176° C.

Example M30

(RS)-5-Methoxy-2-(3-oxo-3-{3-[5-(tetrahydro-pyran-2-yloxymethyl)-[1,2,3]triazol-yl]-phenyl}-propionylamino)-4-trifluoromethyl-phenyl]-carbamic Acid tert.-Butyl Ester The title compound was prepared from (2-amino-5-methoxy-4-trifluoromethyl-phenyl)-carbamic acid tert.-butyl ester (Example J9) (306 mg. 1.0 mmol) and (RS)-3-oxo-3-{3-[5-(tetrahydro-pyran-2-yloxymethyl)-[1,2,3]triazol-1-yl]-phenyl}propionic acid tert.-butyl ester (Example K5) (401 mg, 1.0 mmol) according to the general procedure M. Obtained as an amorphous yellow substance (446 mg).

MS (ISN) 632 [(M−H)$^−$].

Example M31

(RS)-[5-Morpholin-4-yl-2-(3-oxo-3-{3-[5-(tetrahydro-pyran-2-yloxymethyl)-isoxazol-3-yl]-phenyl}-propionylamino)-4-trifluoromethyl-phenyl]-carbamic Acid tert.-Butyl Ester The title compound was prepared from (2-amino-5-morpholin-4-yl-4-trifluoromethyl-phenyl)-carbamic acid tert.-butyl ester (Example J1) and (RS)-3-oxo-3-{3-[5-(tetrahydro-pyran-2-yloxymethyl)-isoxazol-3-yl]-phenyl}-propionic acid tert.-butyl ester (Example K11) according to the general procedure M. Obtained as a light yellow foam (774 mg).

MS (ISN) 687.2 [(M−H)$^−$].

Example M32

{5-Morpholin-4-yl-2-[3-oxo-3-(3-pyrazol-1-yl-phenyl)-propionylamino]-4-trifluoromethyl-phenyl}-carbamic Acid tert.-Butyl Ester The title compound was prepared from (2-amino-5-morpholin-4-yl-4-trifluoromethyl-phenyl)-carbamic acid tert.-butyl ester (Example J1) (361 mg, 1.0 mmol) and 3-oxo-3-(3-pyrazol-1-yl-phenyl)-propionic acid tert.-butyl ester (Example K12) (286 mg, 1.0 mmol) according to the general procedure M. Obtained as a light yellow amorphous substance (367 mg).

MS (ISN) 572 [(M−H)$^−$].

Example M33

{5-Morpholin-4-yl-2-[3-oxo-3-(3-[1,2,4]triazol-4-yl-phenyl)-propionylamino]-4-trifluoromethyl-phenyl}-carbamic Acid tert.-Butyl Ester The title compound was prepared from (2-amino-5-morpholin-4-yl-4-trifluoromethyl-phenyl)-carbamic acid tert.-butyl ester (Example J1) (434 mg, 1.2 mmol) and 3-oxo-3-(3-[1,2,4]triazol-4-yl-phenyl)-propionic acid ethyl ester [CAS-No. 335255-97-5] (259 mg, 1.0 mmol) according to the general procedure M. Obtained as an off-white solid (372 mg).

MS (ISP) 457.4 [(M+H)$^+$]; mp 151–160° C.

Example M34

(RS)-[5-Fluoro-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic Acid tert.-Butyl Ester The title compound was prepared from (2-amino-5-fluoro-4-trifluoromethyl-phenyl)-carbamic acid tert.-butyl ester (Example J10) (294 mg. 1.0 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (442 mg, 1.1 mmol) according to the general procedure M. Obtained as an orange solid (509 mg).

MS (ISN) 620.1 [(M−H)$^−$]; mp 42–45° C.

Example M35

(RS)-[5-Ethoxy-2-(3-oxo-3-{3-[5-(tetrahydro-pyran-2-yloxymethyl)-[1,2,3triazol-1-yl]-phenyl}-propionylamino)-4-trifluoromethyl-phenyl]-carbamic Acid tert.-Butyl Ester The title compound was prepared from (2-amino-5-ethoxy-4-trifluoromethyl-phenyl)-carbamic acid tert.-butyl ester (Example J11) (641 mg. 2.0 mmol) and (RS)-3-oxo-3-{3-[5-(tetrahydro-pyran-2-yloxymethyl)-[1,2,3]triazol-1-yl]-phenyl}-propionic acid tert.-butyl ester (Example K5) (803 mg, 2.0 mmol) according to the general procedure M. Obtained as an amorphous yellow substance (916 mg).

MS (ISN) 646 [(M−H)$^−$].

Example M36

{2-[3-(2-Cyano-pyridin-4-yl)-3-oxo-propionylamino]-5-ethoxy-4-trifluoromethyl-phenyl}-carbamic Acid tert.-Butyl Ester The title compound was prepared from (2-amino-5-ethoxy-4-trifluoromethyl-phenyl)-carbamic acid tert.-butyl ester (Example J11) (160 mg. 0.5 mmol) and 3-(2-cyano-pyridin-4-yl)-3-oxo-propionic acid tert.-butyl ester (Example K3) (123 mg, 0.5 mmol) according to the general procedure M. Obtained as a yellow solid (159 mg).

MS (ISN) 491 [(M−H)⁻]; mp 51° C.

Example M37

{5-Ethoxy-2-[3-oxo-3-(3-[1,2,3]triazol-1-yl-phenyl)-propionylamino]-4-trifluoromethyl-phenyl}-carbamic Acid tert.-Butyl Ester The title compound was prepared from (2-amino-5-ethoxy-4-trifluoromethyl-phenyl)-carbamic acid tert.-butyl ester (Example J11) (240 mg. 0.75 mmol) and 2,2-dimethyl-6-(3-[1,2,3]triazol-1-yl-phenyl)-[1,3]dioxin-4-one (Example L9) (215 mg, 0.75 mmol) according to the general procedure M. Obtained as an off-white solid (245 mg).

MS (ISN) 532 [(M−H)⁻]; mp 175° C.

Example M38

{5-Methoxy-2-[3-oxo-3-(3-[1,2,3]triazol-1-yl-phenyl)-propionylamino]-4-trifluoromethyl-phenyl}-carbamic Acid tert.-Butyl Ester The title compound was prepared from (2-amino-5-methoxy-4-trifluoromethyl-phenyl)-carbamic acid tert.-butyl ester (Example J9) (306 mg. 1.0 mmol) and 2,2-dimethyl-6-(3-[1,2,3]triazol-1-yl-phenyl)-[1,3]dioxin-4-one (Example L9) (271 mg, 1.0 mmol) according to the general procedure M. Obtained as a yellow solid (394 mg).

MS (ISN) 518.1 [(M−H)⁻].

Example M39

{2-[3-(2-Cyano-pyridin-4-yl)-3-oxo-propionylamino]-5-methyl-4-trifluoromethyl-phenyl}-carbamic Acid tert.-Butyl Ester The title compound was prepared from (2-amino-5-methyl-4-trifluoromethyl-phenyl)-carbamic acid tert.-butyl ester (Example J15) and 3-(2-cyano-pyridin-4-yl)-3-oxo-propionic acid tert.-butyl ester (Example K3) according to the general procedure M. Obtained as a light yellow solid (250 mg).

MS (ISN) 461.2 [(M−H)⁻]; mp 181° C. (dec.).

Example M40

{5-Cyano-2-[3-(3-cyano-phenyl)-3-oxo-propionylamino]-4-morpholin-4-yl-phenyl}-carbamic Acid tert-Butyl Ester The title compound was prepared from (2-amino-4-cyano-5-morpholin-4-yl-phenyl)-carbamic acid tert-butyl ester (Example J12) (318 mg, 1.0 mmol) and 3-(3-cyano-phenyl)-3-oxo-propionic acid tert-butyl ester (Example K2) (245 mg, 1.0 mmol) according to the general procedure M. Obtained as a light brown foam (290 mg, 59%).

MS (ISP) 490.3 [(M+H)⁺].

Example M41

(RS)-[4-Cyano-5-morpholin-4-yl-2-(3-oxo-3-{3-[5-(tetrahydro-pyran-2-yloxymethyl)-[1,2,3]triazol-1-yl]-phenyl}-propionylamino)-phenyl]-carbamic Acid tert-Butyl Ester The title compound was prepared from (2-amino-4-cyano-5-morpholin-4-yl-phenyl)-carbamic acid tert-butyl ester (Example J12) (318 mg, 1.0 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (402 mg, 1.0 mmol) according to the general procedure M. Obtained as a light brown foam (370 mg, 57%).

MS (ISP) 644.2 [(M−H)⁻].

Example M42

(4-Cyano-2-{3-[3-(3-methyl-isoxazol-5-yl)-phenyl]-3-oxo-propionylamino}-5-morpholin-4-yl-phenyl)-carbamic Acid tert-Butyl Ester The title compound was prepared from (2-amino-4-cyano-5-morpholin-4-yl-phenyl)-carbamic acid tert-butyl ester (Example J12) (318 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (400 mg, 73%).

MS (ISP) 544.3 [(M−H)⁻].

Example M43

(4-Cyano-2-{3-[3-(3-methyl-isoxazol-5-yl)-phenyl]-3-oxo-propionylamino}-5-morpholin-4-yl-phenyl)-carbamic Acid tert-Butyl Ester The title compound was prepared from (2-amino-4-cyano-5-thiomorpholin-4-yl-phenyl)-carbamic acid tert-butyl ester (Example J13) (334 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a light brown foam (440 mg, 78%).

MS (ISP) 562.3 [(M+H)⁺].

Example M44

(RS)-[5-Chloro-2-(3-oxo-3-{3-[5-(tetrahydro-pyran-2-yloxymethyl)-[1,2,3]triazol-phenyl}-propionylamino)-4-trifluoromethyl-phenyl]-carbamic Acid tert-Butyl Ester The title compound was prepared from (2-amino-5-chloro-4-trifluoromethyl-phenyl)-carbamic acid tert-butyl ester (Example J14) (774 mg, 2.49 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (1.0 mg, 2.49 mmol) according to the general procedure M. Obtained as a light yellow foam (790 mg, 50%).

MS (ISP) 635.9 [(M−H)⁻].

Example M45

(5-Chloro-2-{3-[3-(3-methyl-isoxazol-5-yl)-phenyl]-3-oxo-propionylamino}-4-trifluoromethyl-phenyl)-carbamic Acid tert-Butyl Ester The title compound was prepared from (2-amino-5-chloro-4-trifluoromethyl-phenyl)-carbamic acid tert-butyl ester (Example J14) (311 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as an off-white solid (210 mg, 39%).

MS (ISP) 536.1 [(M−H)⁻]; mp 172° C.

Example M46

(RS)-[5-Methyl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic Acid tert-Butyl Ester The title compound was prepared from (2-amino-5-methyl-4-trifluoromethyl-phenyl)-carbamic acid tert-butyl ester (Example J15) (1.0 g, 3.44 mmol) and (RS)-3-oxo-3-{3-[5-(tetrahydro-pyran-2-yloxymethyl)-[1,2,3]triazol-1-yl]-phenyl}-propionic acid tert-butyl ester (Example K5) (1.38 g, 3.44 mmol) according to the general procedure M. Obtained as an off-white foam (910 mg, 43%).

MS (ISP) 616.1 [(M−H)⁻].

Example M47

(5-Methyl-2-{3-[3-(3-methyl-isoxazol-5-yl)-phenyl]-3-oxo-propionylamino}-4-trifluoromethyl-phenyl)-carbamic Acid tert-Butyl Ester The title compound was prepared from (2-amino-5-methyl-4-trifluoromethyl-phenyl)-carbamic acid tert-butyl ester (Example J15) (290 mg, 1.0 mmol) and 3-[3-(3-methyl-isoxazol-5-yl)-phenyl]-3-oxo-propionic acid tert-butyl ester (Example K4) (301 mg, 1.0 mmol) according to the general procedure M. Obtained as a white solid (240 mg, 46%).

MS (ISP) 516.2 [(M−H)⁻].

Example M48

{5-Chloro-2-[3-oxo-3-(3-[1,2,4]triazol-1-yl-phenyl)-propionylamino]-4-trifluoromethyl-1phenyl}-carbamic Acid tert-Butyl Ester The title compound was prepared from (2-amino-5-chloro-4-trifluoromethyl-phenyl)-carbamic acid tert-butyl ester (Example J14) (311 mg, 1.0 mmol) and 3-oxo-3-(3-[1,2,4]triazol-1-yl-phenyl)-propionic acid tert-butyl ester (Example K15) (287 mg, 1.0 mmol) according to the general procedure M. Obtained as a white foam (360 mg, 69%).

MS (ISP) 522.0 [(M−H)⁻].

Example M49

{5-Chloro-2-[3-(3-imidazol-1-yl-phenyl)-3-oxo-propionylamino]-4-trifluoromethyl-phenyl}-carbamic Acid tert-Butyl Ester The title compound was prepared from (2-amino-5-chloro-4-trifluoromethyl-phenyl)-carbamic acid tert-butyl ester (Example J14) (311 mg, 1.0 mmol) and 3-(3-imidazol-1-yl-phenyl)-3-oxo-propionic acid tert-butyl ester (Example K16) (286 mg, 1.0 mmol) according to the general procedure M. Obtained as a light yellow foam (160 mg, 31%).

MS (ISP) 521.0 [(M−H)⁻].

Example M50

{5-Chloro-2-[3-oxo-3-(3-[1,2,3]triazol-1-yl-phenyl)-propionylamino]-4-trifluoromethyl-phenyl}-carbamic Acid tert-Butyl Ester The title compound was prepared from (2-amino-5-chloro-4-trifluoromethyl-phenyl)-carbamic acid tert-butyl ester (Example J14) (311 mg, 1.0 mmol) 3-oxo-3-(3-[1,2,3]triazol-1-yl-phenyl)-propionic acid ethyl ester (Example K1) (259 mg, 1.0 mmol) according to the general procedure M. Obtained as a light yellow oil (340 mg, 65%).

MS (ISP) 522.0 [(M−H)⁻].

Example M51

{5-Methyl-2-[3-oxo-3-(3-[1,2,4]triazol-1-yl-phenyl)-propionylamino]-4-trifluoromethyl-phenyl}-carbamic Acid tert-Butyl Ester The title compound was prepared from (2-amino-5-methyl-4-trifluoromethyl-phenyl)-carbamic acid tert-butyl ester (Example J15) (290 mg, 1.0 mmol) and 3-oxo-3-(3-[1,2,4]triazol-1-yl-phenyl)-propionic acid tert-butyl ester (Example K15) (287 mg, 1.0 mmol) according to the general procedure M. Obtained as a white foam (420 mg, 83%).

MS (ISP) 502.1 [(M−H)⁻].

Example M52

{5-Methyl-2-[3-(3-imidazol-1-yl-phenyl)-3-oxo-propionylamino]-4-trifluoromethyl-phenyl}-carbamic Acid tert-Butyl Ester The title compound was prepared from (2-amino-5-methyl-4-trifluoromethyl-phenyl)-carbamic acid tert-butyl ester (Example J15) (290 mg, 1.0 mmol) and 3-(3-imidazol-1-yl-phenyl)-3-oxo-propionic acid tert-butyl ester (Example K16) (286 mg, 1.0 mmol) according to the general procedure M. Obtained as a light yellow foam (380 mg, 76%).

MS (ISP) 501.2 [(M−H)⁻].

Example M53

{5-Methyl-2-[3-oxo-3-(3-[1,2,3]triazol-1-yl-phenyl)-propionylamino]-4-trifluoromethyl-phenyl}-carbamic Acid tert-Butyl Ester The title compound was prepared from (2-amino-5-methyl-4-trifluoromethyl-phenyl)-carbamic acid tert-butyl ester (Example J15) (290 mg, 1.0 mmol) and 3-oxo-3-(3-[1,2,3]triazol-1-yl-phenyl)-propionic acid ethyl ester (Example K1) (259 mg, 1.0 mmol) according to the general procedure M. Obtained as a light yellow oil (300 mg, 60%).

MS (ISP) 502.1 [(M−H)⁻].

Example M54

{5-Methyl-2-[3-oxo-3-(3-pyrazol-1-yl-phenyl)-propionylamino]-4-trifluoromethyl-phenyl}-carbamic Acid tert-Butyl Ester The title compound was prepared (2-amino-5-methyl-4-trifluoromethyl-phenyl)-carbamic acid tert-butyl ester (Example J15) (290 mg, 1.0 mmol) and 3-oxo-3-(3-pyrazol-1-yl-phenyl)-propionic acid tert-butyl ester (Example K12) (286 mg, 1.0 mmol) according to the general procedure M. Obtained as a white solid (370 mg, 74%).

MS (ISP) 503.3 [(M+H)⁺]; mp 172° C.

Example M55

(RS)-[5-Chloro-2-(3-oxo-3-{3-[5-(tetrahydro-pyran-2-yloxymethyl)-[1,2,4]triazol-1-yl]-phenyl}-propionylamino)-4-trifluoromethyl-phenyl]-carbamic Acid tert-Butyl Ester The title compound was prepared from (2-amino-5-chloro-4-trifluoromethyl-phenyl)-carbamic acid tert-butyl ester (Example J14) (900 mg, 2.90 mmol) and (RS)-3-oxo-3-{3-[5-(tetrahydro-pyran-2-yloxymethyl)-[1,2,4]triazol-1-yl]-phenyl}-propionic acid tert-butyl ester (Example K14) (1.16 g, 2.90 mmol) according to the general procedure M. Obtained as a light yellow foam (790 mg, 43%).

MS (ISP) 635.3 [(M−H)⁻].

General Procedure N

Preparation of 4-Aryl-1,3-dihydro-benzo[b][1,4]diazepin-2-ones

A solution or suspension of the {2-[3-aryl-3-oxo-propionylamino]-phenyl}-carbamic acid tert-butyl ester or {2-[3-aryl-3-oxo-propionylamino]-phenyl}-carbamic acid tert-butyl ester (1.0 mmol) in $CH_2Cl_2$ (5 mL) [anisole or 1,3-dimethoxybenzene (5–15 mmol) can be added if necessary] was treated with TFA (0.5–5.0 mL) at 0° C. and stirring was continued at 23° C. until tlc indicated complete consumption of the starting material.

Workup procedure a: The solvent was removed in vacuum, the residue treated with little ether, whereupon it crystallized. The solid was stirred with sat. $NaHCO_3$-sol. or 1M $Na_2CO_3$-sol., filtered, washed with $H_2O$ and ether or mixtures of ether/THF/MeOH and was dried to give the title compound, which if necessary can be purified by crystallization from 1,4-dioxane or by silica gel column chromatography with cyclohexane/EtOAc or EtOAc/EtOH.

Workup procedure b: The reaction mixture was diluted with DCM or EtOAc, washed with sat. $NaHCO_3$-sol. or 1M $Na_2CO_3$-sol., brine and dried over $MgSO_4$ or $Na_2SO_4$. Removal of the solvent in vacuum left a material, which could be triturated with ether or mixtures of ether/THF/MeOH to give the title compound, or which if necessary can be purified by crystallization from 1,4-dioxane or by silica gel column chromatography with cyclohexane/EtOAc or EtOAc/EtOH.

Example 1

4-[3-(5-Hydroxymethyl-[1,2,3]triazol-1-yl)-phenyl]-7-morpholin-4-yl-8-trifluoromethyl-1,3-dihydro-benzo[b][1,4]diazepin-2-one The title compound was prepared from (RS)-[5-morpholin-4-yl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M1) by treatment with TFA in $CH_2Cl_2$ according to the general procedure N. Obtained as an off-white solid (51 mg).

MS (ISP) 487 [(M+H)$^+$]; mp 200° C.

Example 2

4-(8-Morpholin-4-yl-4-oxo-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-morpholin-4-yl-4-trifluoromethyl-phenyl}-carbamic acid tert.-butyl ester (Example M2) by treatment with TFA in $CH_2Cl_2$ according to the general procedure N. Obtained as a yellow solid (11 mg).

MS (ISP) 416 [(M+H)$^+$]; mp 220° C.

Example 3

4-[3-(3-Methyl-isoxazol-5-yl)-phenyl]-7-morpholin-4-yl-8-trifluoromethyl-1,3-dihydro-benzo[b][1,4]diazepin-2-one The title compound was prepared from (2-{3-[3-(3-methyl-isoxazol-5-yl)-phenyl]-3-oxo-propionylamino}-5-morpholin-4-yl-4-trifluoromethyl-phenyl)-carbamic acid tert.-butyl ester (Example M3) by treatment with TFA in $CH_2Cl_2$ according to the general procedure N. Obtained as an off-white solid (29 mg).

MS (ISP) 471 [(M+H)$^+$]; mp 170° C.

Example 4

3-(4-oxo-7-Pyrrol-1-yl-4,5-dihydro-3H-benzo[b][1,4]diazepin-2-yl)-benzonitrile

The title compound was prepared from {2-[3-(3-cyano-phenyl)-3-oxo-propionylamino]-4-pyrrol-1-yl-phenyl}-carbamic acid tert-butyl ester (Example M5) by treatment with TFA in $CH_2Cl_2$ according to the general procedure N. Obtained as a yellow solid (1.51 g).

Alternatively, the title compound was also prepared from (3-(3-cyano-phenyl)-N-(2-nitro-5-pyrrol-1-yl-phenyl)-3-oxo-propionamide (Example M4) by reductive cyclization with $SnCl_2.2H_2O$ in EtOH at 70° C. according to the general procedure J (method b). Obtained as an olive solid (161 mg).

MS (EI) 326 (M$^+$); mp 219° C.

Example 5

4-(2-Chloro-phenyl)-1-[2-(3-cyano-phenyl)-4-oxo-4,5-dihydro-3H-benzo[b][1,4]diazepin-7-yl]-1H-pyrrole-3-carbonitrile The title compound was prepared from N-{5-[3-(2-chloro-phenyl)-4-cyano-pyrrol-1-yl]-2-nitro-phenyl}-3-(3-cyano-phenyl)-3-oxo-propionamide (Example M6) by reductive cyclization with Fe/HOAc in THF/$H_2O$ at 80° C. according to the general procedure J (method d). Obtained as a brown solid (164 mg).

MS (EI) 461 (M$^+$) and 463 [(M+2)$^+$]; mp 252° C. (dec.).

Example 6

1-[2-(3-Cyano-phenyl)-4-oxo-4,5-dihydro-3H-benzo[b][1,4]diazepin-7-yl]-4-phenyl-1H-pyrrole-3-carbonitrile The title compound was prepared from 3-(3-cyano-phenyl)-N-[5-(3-cyano-4-phenyl-pyrrol-1-yl)-2-nitro-phenyl]-3-oxo-propionamide (Example M7) by reductive cyclization with Fe/HOAc in THF/$H_2O$ at 80° C. according to the general procedure J (method d). Obtained as a brown solid (206 mg).

MS (EI) 427 (M$^+$); mp 274° C. (dec.).

Example 7

4-(3-Iodo-phenyl)-8-pyrrol-1-yl-1,3-dihydro-benzo[b][1,4]diazepin-2-one

The title compound was prepared from 3-(3-iodo-phenyl)-N-(2-nitro-4-pyrrol-1-yl-phenyl)-3-oxo-propionamide (Example M8) by reductive cyclization with $SnCl_2.2H_2O$ in EtOH at 70° C. according to the general procedure J (method b). Obtained as an olive solid (624 mg).

MS (EI) 427 (M$^+$); mp 215–217° C. (dec.).

Example 8

3-(4-oxo-7-Pyrrol-1-yl-4,5-dihydro-3H-benzo[b][1,4]diazepin-2-yl)-benzamide

A mixture of 4-(3-iodo-phenyl)-8-pyrrol-1-yl-1,3-dihydro-benzo[b][1,4]diazepin-2-one (Example 7) (214 mg, 0.5 mmol), Pd(OAc)$_2$ (4 mg, 3 mol %), PPh$_3$ (8mg, 8 mol %) and HDMS (0.52 mL, 2.5 mmol) in DMF (2 mL) was stirred under CO atmosphere at 60° C. for 4 h. The mixture was taken up in EtOAc, washed with 1 N HCl, sat. NaHCO3-sol. and brine, dried over MgSO4. Removal of the solvent in vacuum left a dark brown solid, which was purified by silica gel column chromatography with EtOAc/MeOH 95:5. Obtained as a yellow-brown solid (97 mg).

MS (EI) 344 (M$^+$); mp 238–239° C. (dec.).

Example 9

3-(8-Iodo-4-oxo-7-pyrrol-1-yl-4,5-dihydro-3H-benzo[b][1,4]diazepin-2-yl)-benzonitrile The title compound was prepared from 3-(3-cyano-phenyl)-N-(4-iodo-2-nitro-5-pyrrol-1-yl-phenyl)-3-oxopropionamide (Example M9) by reductive cyclization with SnCl$_2$.2H$_2$O in EtOH at 70° C. according to the general procedure J (method b). Obtained as a yellow solid (344 mg).

MS (EI) 452 (M$^+$); mp 215° C.

Example 10

3-[8-(2-Methoxy-ethoxy)-4-oxo-7-pyrrol-1-yl-4,5-dihydro-3H-benzo[b][1,4]diazepin-2-yl]-benzonitrile The title compound was prepared from [2-[3-(3-cyano-phenyl)-3-oxo-propionylamino]-5-(2-methoxy-ethoxy)-4-pyrrol-1-yl-phenyl]-carbamic acid tert.-butyl ester (Example M10) by treatment with TFA in CH$_2$Cl$_2$ according to the general procedure N. Obtained as a beige solid (22 mg).

MS (EI) 400 (M$^+$); mp 189–195° C.

Example 11

3-[7-(3-Hydroxymethyl-pyrrol-1-yl)-4-oxo-4,5-dihydro-3H-benzo[b][1,4]diazepin-2-yl]-benzonitrile The title compound was prepared from 3-(3-cyano-phenyl)-N-[5-(3-hydroxymethyl-pyrrol-1-yl)-2-nitro-phenyl]-3-oxo-propionamide (Example M11) by reductive cyclization with Fe/HOAc in THF/H$_2$O at 60° C. according to the general procedure J (method d). Obtained as a brown solid (18 mg).

MS (EI) 356 (M$^+$).

Example 12

3-[4-oxo-7-(3-Phenyl-pyrrol-1-yl)-4,5-dihydro-3H-benzo[b][1,4]diazepin-2-yl]-benzonitrile The title compound was prepared from 3-(3-cyano-phenyl)-N-[2-nitro-5-(3-phenyl-pyrrol-1-yl)-phenyl]-3-oxo-propionamide (Example M12) by reductive cyclization with Fe/HOAc in THF/H$_2$O at 80° C. according to the general procedure J (method d). Obtained as a yellow solid (11 mg).

MS (EI) 402 (M$^+$).

Example 13

3-[7-(3-Methoxymethyl-pyrrol-1-yl)-4-oxo-4,5-dihydro-3H-benzo[b][1,5]diazepin-2-yl]-benzonitrile The title compound was prepared from 3-(3-cyano-phenyl)-N-[5-(3-methoxymethyl-pyrrol-1-yl)-2-nitro-phenyl]-3-oxo-propionamide (Example M13) by reductive cyclization with Fe/HOAc in THF/H$_2$O at 80° C. according to the general procedure J (method d). Obtained as a brown solid (62 mg).

MS (EI) 370 (M$^+$).

Example 14

3-[7-(2-Methoxymethyl-pyrrol-1-yl)-4-oxo-4,5-dihydro-3H-benzo[b][1,5]diazepin-2-yl]-benzonitrile The title compound was prepared from 3-(3-cyano-phenyl)-N-[5-(2-methoxymethyl-pyrrol-1-yl)-2-nitro-phenyl]-3-oxo-propionamide (Example M14) by reductive cyclization with Fe/HOAc in THF/H$_2$O at 80° C. according to the general procedure J (method d). Obtained as a brown solid (178 mg).

MS (EI) 370 (M$^+$); mp >197° C. (dec.).

Example 15

1-[2-(3-Cyano-phenyl)-4-oxo-4,5-dihydro-3H-benzo[b][1,4]diazepin-7-yl]-1H-pyrrole-2-carboxylic Acid Methyl Ester The title compound was prepared from 1-{3-[3-(3-cyano-phenyl)-3-oxo-propionylamino]-4-nitro-phenyl}-1H-pyrrole-2-carboxylic acid methyl ester (Example M15) by reductive cyclization with Fe/HOAc in THF/H$_2$O at 80° C. according to the general procedure J (method d). Obtained as a brown solid (323 mg).

MS (EI) 384 (M$^+$); mp >207° C. (dec.).

Example 16

4-(3-Imidazol-1-yl-phenyl)-8-pyrrol-1-yl-1,3-dihydro-benzo[b][1,4]diazepin-2-one The title compound was prepared from {2-[3-(3-imidazol-1-yl-phenyl)-3-oxo-propionylamino]-4-pyrrol-1-yl-phenyl}-carbamic acid tert.-butyl ester (Example M17) by treatment with TFA in CH$_2$Cl$_2$ according to the general procedure N. Obtained as a yellow solid (1.03 g).

Alternatively, the title compound was also prepared from 3-(3-imidazol-1-yl-phenyl)-N-(2-nitro-5-pyrrol-1-yl-phenyl)-3-oxo-propionamide (Example M16) by reductive cyclization with Fe/HOAc in THF/H$_2$O at 60° C. according to the general procedure J (method d). Obtained as a brown solid (100 mg).

MS (EI) 367 (M$^+$); mp 220° C.

Example 17

3-(8-Methoxy-4-oxo-7-pyrrol-1-yl-4,5-dihydro-3H-benzo[b][1,4]diazepin-2-yl)-benzonitrile The title compound was prepared from {2-[3-(3-cyano-phenyl)-3-oxo-propionylamino]-5-methoxy-4-pyrrol-1-yl-phenyl}-carbamic acid tert.-butyl ester (Example M18) by treatment with TFA in CH$_2$Cl$_2$ according to the general procedure N. Obtained as a yellow solid (10 mg).

MS (EI) 356 (M$^+$).

Example 18

3-[7-(2-tert.-Butyl-pyrrol-1-yl)-8-methoxy-4-oxo-4,5-dihydro-3H-benzo[b][1,4]diazepin-2-yl]-benzonitrile The title compound was prepared from {4-(2-tert.-butyl-pyrrol-1-yl)-2-[3-(3-cyano-phenyl)-3-oxo-propionylamino]-5-methoxy-phenyl}-carbamic acid tert.-butyl ester (Example M19) by treatment with TFA in CH$_2$Cl$_2$ according to the general procedure N. Obtained as a yellow solid (22 mg).

MS (EI) 412 (M$^+$); mp >250° C.

Example 19

2-[3-(4-oxo-7-Pyrrol-1-yl-4,5-dihydro-3H-benzo[b][1,4]diazepin-2-yl)-phenyl]-thiazole-4-carboxylic Acid Ethyl Ester A mixture of 3-(4-oxo-7-pyrrol-1-yl-4,5-dihydro-3H-benzo[b][1,4]diazepinthiobenzamide [prepared from 3-(4-oxo-7-pyrrol-1-yl-4,5-dihydro-3H-benzo[b][1,4]diazepin-2-yl)-benzonitrile (Example 4) as follows: To a solution of hexamethyldisilthiane (1.38 mL, 6.5 mmol) in 1,3-dimethyl-2-imidazolidinone (6 mL) was added at 23° C. sodium methoxide (0.34 g, 6.3 mmol). The mixture was stirred for 15 min. and the blue solution formed was then added to a solution of 3-(4-oxo-7-pyrrol-1-yl-4,5-dihydro-3H-benzo[b][1,4]diazepin-2-yl)-benzonitrile (Example 4) (0.98 g, 3 mmol) in 1,3-dimethyl-2-imidazolidinone (9 mL). The mixture was stirred for 3 h at 23° C. and then poured into H$_2$O (200 mL). The mixture was extracted with EtOAc, the organic layer was dried over Na₂SO₄ and evaporated in vacuum. The remaining oil was stirred for 0.5 h with H₂O (150 mL) and the precipitate formed was isolated by filtration and dried to give 3-(4-oxo-7-pyrrol-1-yl-4,5-dihydro-3H-benzo[b][1,4]diazepin-2-yl)-thiobenzamide (0.86 g) as light yellow solid, mp 198–201° C. (dec.), MS (ISN) 359.0 [(M−H)⁻].] (0.3 g, 0.84 mmol) and ethyl bromopyruvate (0.16 mL, 1.26 mmol) in ethanol (4 mL) was heated at reflux for 20 min. The solution was evaporated in vacuum and the residue was triturated with EtOAc to give the title compound (0.24 g) as a light-yellow solid.

MS (ISP) 455.2 [(M−H)⁻]; mp 198–201° C.

Example 20

4-[3-(4-Hydroxymethyl-thiazol-2-yl)-phenyl]-8-pyrrol-1-yl-1,3-dihydro-benzo[b][1,4]diazepin-2-one To a stirred suspension of 2-[3-(4-oxo-7-pyrrol-1-yl-4,5-dihydro-3H-benzo[b][1,4]diazepin-2-yl)-phenyl]-thiazole-4-carboxylic acid ethyl ester (Example 19) (0.34 g, 0.75 mmol) in THF (35 mL) was added at −20° C. over 40 min in 3 portions a 3.5 M solution of sodium dihydrido-bis(2-methoxyethoxy)aluminate in toluene (0.94 mL, 3.3 mmol). Stirring was continued at −20° C. for 20 min. and the reaction mixture was then poured into ice-cold 10% aqueous acetic acid. The product was extracted with EtOAc and the organic layer was washed successively with H₂O, sat. Na₂CO₃-solution and brine, dried over Na₂SO₄ and evaporated in vacuum. The residue was triturated with methanol to give the title compound (0.28 g) as light-yellow solid.

MS (ISN) 413.1 [(M−H)⁻]; mp 238–240° C.

Example 21

8-Pyrrol-1-yl-4-(3-[1,2,3]triazol-1-yl-phenyl)-1,3-dihydro-benzo[b][1,4]diazepin-2-one The title compound was prepared from {2-[3-oxo-3-(3-[1,2,3]triazol-1-yl-phenyl)-propionylamino]-4-pyrrol-1-yl-phenyl}-carbamic acid tert.-butyl ester (Example M20) by treatment with TFA in CH₂Cl₂ according to the general procedure N. Obtained as a light yellow solid (36 mg).

MS (ISP) 369 [(M+H)⁺]; mp 206–209° C.

Example 22

4-(3-Oxazol-2-yl-phenyl)-8-pyrrol-1-yl-1,3-dihydro-benzo[b][1,4]diazepin-2-one

The title compound was prepared from (2-amino-4-pyrrol-1-yl-phenyl)-carbamic acid tert.-butyl ester (Example J2) (137 mg) and 2,2-dimethyl-6-(3-oxazol-2-yl-phenyl)-[1,3]dioxin-4-one (Example L5) (271 mg) according to the general procedure M. The obtained material was deprotected and cyclized by treatment with TFA in CH₂Cl₂ according to the general procedure N. Obtained as a light yellow solid (83 mg).

MS (ISP) 369.2 [(M+H)⁺]; mp 251–253° C.

Example 23

5-[3-(4-oxo-7-Pyrrol-1-yl-4,5-dihydro-3H-benzo[b][1,4]diazepin-2-yl)-phenyl]-oxazole-4-carboxylic Acid Ethyl Ester The title compound was prepared from (2-amino-4-pyrrol-1-yl-phenyl)-carbamic acid tert.-butyl ester (Example J2) (164 mg) and 5-[3-(2,2-dimethyl-6-oxo-6H-[1,3]dioxin-4-yl)-phenyl]-oxazole-4-carboxylic acid ethyl ester (Example L6) (206 mg) according to the general procedure M. The obtained material was deprotected and cyclized by treatment with TFA in CH₂Cl₂ according to the general procedure N. Obtained as a light yellow solid (63 mg).

MS (ISP) 441.2 [(M+H)⁺]; mp 222–224° C.

Example 24

5-[3-(4-oxo-7-Pyrrol-1-yl-4,5-dihydro-3H-benzo[b][1,4]diazepin-2-yl)-phenyl]-oxazole-4-carboxylic Acid (2-Hydroxy-ethyl)-amide A solution of 5-[3-(4-oxo-7-pyrrol-1-yl-4,5-dihydro-3H-benzo[b][1,4]diazepin-2-yl)-phenyl]-oxazole-4-carboxylic acid ethyl ester (Example 23) (35mg) in 2-amino-ethanol (1 mL) was stirred at 50° C. for 4 h. The mixture was partitioned between H₂O and EtOAc. The organic layer was dried and evaporated in vacuum, and the residue was triturated with EtOAc to give the title compound (20 mg) as light-yellow solid.

MS (ISP) 456.4 [(M+H)⁺]; mp 228–230° C.

Example 25

2-[3-(4-oxo-7-Pyrrol-1-yl-4,5-dihydro-3H-benzo[b][1,4]diazepin-2-yl)-phenyl]-oxazole-4-carboxylic Acid Methyl Ester The title compound was prepared from (2-amino-4-pyrrol-1-yl-phenyl)-carbamic acid tert.-butyl ester (Example J2) (680 mg) and 2-[3-(2,2-dimethyl-6-oxo-6H-[1,3]dioxin-4-yl)-phenyl]-oxazole-4-carboxylic acid methyl ester (Example L7) (820 mg) according to the general procedure M. The obtained material was deprotected and cyclized by treatment with TFA in CH₂Cl₂ according to the general procedure N. Obtained as a light yellow solid (770 mg).

MS (ISP) 433.2 [(M+H)⁺]; mp 240–245° C. (dec.).

Example 26

4-[3-(4-Hydroxymethyl-oxazol-2-yl)-phenyl]-8-pyrrol-1-yl-1,3-dihydro-benzo[b][1,4]diazepin-2-one To a solution of 2-[3-(4-oxo-7-pyrrol-1-yl-4,5-dihydro-3H-benzo[b][1,4]diazepin-2-yl)-phenyl]-oxazole-4-carboxylic acid methyl ester (Example 25) (88 mg, 0.2 mmol) in THF (1.5 mL) were added successively MeOH (0.012 mL) and lithium borohydride (6.5 mg, 0.3 mmol). The mixture was stirred at 40° C. for 1 h and then partitioned between EtOAc and 1N HCl. The organic layer was washed with brine, dried and evaporated in vacuum. The residue was chromatographed on silica gel using EtOAc/hexane (1:2) as eluents to give the title compound (24 mg) as light-yellow solid.

MS (ISP) 399.4 [(M+H)⁺]; mp 240–242° C.

Example 27

2-[3-(4-oxo-7-Pyrrol-1-yl-4,5-dihydro-3H-benzo[b][1,4]diazepin-2-yl)-phenyl]-oxazole-4-carboxylic Acid Amide A suspension of 2-[3-(4-oxo-7-pyrrol-1-yl-4,5-dihydro-3H-benzo[b][1,4]diazepin-2-yl)-phenyl]-oxazole-4-carboxylic acid methyl ester (Example 25) (44mg) in a 5N solution (3 mL) of NH₃ in MeOH was stirred at 20° C. for 3 d. Insoluble material was filtered off and the solution was evaporated in vacuum. The residue was triturated with EtOAc to give the title compound (22 mg) as light-yellow solid.

S (ISP) 412.2 [(M+H)⁺]; mp 232–234° C.

Example 28

4-[3-(4-oxo-7-Pyrrol-1-yl-4,5-dihydro-3H-benzo[b][1,4]diazepin-2-yl)-phenyl]-thiazole-2-carboxylic Acid Ethyl Ester The title compound was prepared from (2-amino-4-pyrrol-1-yl-phenyl)-carbamic acid tert.-butyl ester (Example J2) (1.9 g) and 5-[3-(2,2-dimethyl-6-oxo-6H-[1,3]dioxin-4-yl)-phenyl]-thiazole-2-carboxylic acid ethyl ester (Example L8) (2.5 g) according to the general procedure M. The obtained material was deprotected and cyclized by treatment with TFA in $CH_2Cl_2$ according to the general procedure N. Obtained as a light yellow solid (0.85 g).

MS (ISP) 457.2 [(M+H)$^+$]; mp 213–215° C.

Example 29

4-[3-(3-Methyl-isoxazol-5-yl)-phenyl]-8-pyrrol-1-yl-1,3-dihydro-benzo[b][1,4]diazepin-2-one The title compound was prepared from (2-amino-4-pyrrol-1-yl-phenyl)-carbamic acid tert.-butyl ester (Example J2) (191 mg) and 3-[3-(3-methyl-isoxazol-5-yl)-phenyl]-3-oxo-propionic acid tert.-butyl ester (Example K4) (211 mg) according to the general procedure M. The obtained material was deprotected and cyclized by treatment with TFA in $CH_2Cl_2$ according to the general procedure N. Obtained as a light yellow solid (92 mg).

MS (ISP) 383.2 [(M+H)$^+$]; mp 248–250° C.

Example 30

4-[3-(4-oxo-7-Pyrrol-1-yl-4,5-dihydro-3H-benzo[b][1,4]diazepin-2-yl)-phenyl]-thiazole-2-carboxylic Acid Amide A sample of 4-[3-(4-oxo-7-pyrrol-1-yl-4,5-dihydro-3H-benzo[b][1,4]diazepin-2-yl)-phenyl]-thiazole-2-carboxylic acid ethyl ester (Example 28) (0.07 g) was reacted with ammonia in an analogous manner to the procedure described in Example 27 to give the title compound (0.05 g) as a light-yellow solid.

MS (ISP) 428.4[(M+H)$^+$]; mp 267–269° C.

Example 31

2-[3-(4-oxo-7-Pyrrol-1-yl-4,5-dihydro-3H-benzo[b][1,4]diazepin-2-yl)-phenyl]-oxazole-4-carboxylic Acid bis-(2-Hydroxy-ethyl)-amide A solution of 2-[3-(4-oxo-7-pyrrol-1-yl-4,5-dihydro-3H-benzo[b][1,4]diazepin-2-yl)-phenyl]-oxazole-4-carboxylic acid methyl ester (Example 25)(88 mg) in 2-(2-hydroxy-ethylamino)-ethanol (2 mL) was stirred at 50° C. for 6 h. The mixture was partitioned between $H_2O$ and EtOAc. The organic layer was dried and evaporated in vacuum, and the residue was triturated with EtOAc to give the title compound (32 mg) as light-yellow solid.

MS (ISP) 500.4 [(M+H)$^+$].

Example 32

4-[3-(4-oxo-7-Pyrrol-1-yl-4,5-dihydro-3H-benzo[b][1,4]diazepin-2-yl)-phenyl]-thiazole-2-carboxylic Acid (2-Hydroxy-ethyl)-amide A sample of 4-[3-(4-oxo-7-pyrrol-1-yl-4,5-dihydro-3H-benzo[b][1,4]diazepin-2-yl)-phenyl]-thiazole-2-carboxylic acid ethyl ester (Example 28) (0.26 g) was reacted with 2-amino-ethanol in an analogous manner to the procedure described in Example 34 to give the title compound (0.07 g) as a light-yellow solid.

MS (ISP) 472.3 [(M+H)$^+$]; mp 236–238° C.

Example 33

4-[3-(2-Hydroxymethyl-thiazol-4-yl)-phenyl]-8-pyrrol-1-yl-1,3-dihydro-benzo[b][1,4]diazepin-2-one A sample of 4-[3-(4-oxo-7-pyrrol-1-yl-4,5-dihydro-3H-benzo[b][1,4]diazepin-2-yl)-phenyl]-thiazole-2-carboxylic acid ethyl ester (Example 28) (0.14 g) was reacted with sodium dihydrido-bis(2-methoxyethoxy)aluminat in an analogous manner to the procedure described in Example 20 to give the title compound (0.03 g) as an off-white solid.

MS (ISP) 415.2 [(M+H)$^+$]; mp 185–190° C. (dec.).

Example 34

2-[3-(4-oxo-7-Pyrrol-1-yl-4,5-dihydro-3H-benzo[b][1,4]diazepin-2-yl)-phenyl]-oxazole-4-carboxylic Acid (2-Hydroxy-ethyl)-amide A solution of 2-[3-(4-oxo-7-pyrrol-1-yl-4,5-dihydro-3H-benzo[b][1,4]diazepin-2-yl)-phenyl]-oxazole-4-carboxylic acid methyl ester (Example 25) (88 mg) in 2-amino-ethanol (2 mL) was stirred at 50° C. for 2 h. The mixture was partitioned between EtOAc and $H_2O$, the organic layer was dried and evaporated in vacuum. The residue was chromatographed on silicag gel using EtOAc/hexane (1:1) as eluent and the purified product was triturated with $Et_2O$ to give the title compound (20 mg) as light-yellow solid.

MS (ISP) 456.4 [(M+H)$^+$]; mp 242–244° C.

Example 35

4-[3-(4-(Dimethylamino-methyl)-thiazol-2-yl)-phenyl]-8-pyrrol-1-yl-1,3-dihydro-benzo[b][1,4]diazepin-2-one A mixture of 4-[3-(4-(chloromethyl)-thiazol-2-yl)-phenyl]-8-pyrrol-1-yl-1,3-dihydro-benzo[b][1,4]diazepin-2-one {prepared as follows: A mixture of 3-(4-oxo-7-pyrrol-1-yl-4,5-dihydro-3H-benzo[b][1,4]diazepin-2-yl)-thiobenzamide [prepared as from 3-(4-oxo-7-pyrrol-1-yl-4,5-dihydro-3H-benzo[b][1,4]diazepin-2-yl)-benzonitrile (Example 4) as described in Example 19] (144 mg), 1,3-dichloro-2-propanone (76 mg) and sodium bicarbonate (50 mg) in 1,4-dioxane (3 mL) was heated to 60° C. for 15 h. The reaction mixture was cooled to 20° C. and diluted with $H_2O$ (20 mL). The precipitate was collected and dried to give 4-[3-(4-(chloromethyl)-thiazol-2-yl)-phenyl]-8-pyrrol-1-yl-1,3-dihydro-benzo[b][1,4]diazepin-2-one (154 mg) as a light-brown solid. MS (ISP) 427.4 [(M+H)$^+$].} (88 mg, 0.2 mmol) and potassium iodide (10 mg, 0.06 mmol) in a 33% solution of dimethylamine in methanol (1 mL, 5.5 mmol) was heated to 40° C. for 2 h. The mixture was evaporated in vacuum and the residue was chromatographed on silica gel using EtOAc/acetone (1:1) as eluent to give the title compound (31 mg) as a light-brown solid.

MS (ISP) 442.2 [(M+H)$^+$].

Example 36

4-[3-(4-Morpholin-4-ylmethyl-thiazol-2-yl)-phenyl]-8-pyrrol-1-yl-1,3-dihydro-benzo[b][1,4]diazepin-2-one A mixture of 4-[3-(4-(chloromethyl)-thiazol-2-yl)-phenyl]-8-pyrrol-1-yl-1,3-dihydro-benzo[b][1,4]diazepin-2- one (cf. Example 35) (65 mg, 0.15 mmol), morpholine (0.11 mL, 1.2 mmol) and potassium iodide (5 mg, 0.03 mmol) in methanol (1 mL) was heated to 40° C. for 1 h. The mixture was diluted with $H_2O$ and the precipitate formed was collected by filtration and chromatographed on silica gel using EtOAc/methanol (10:1) as eluent to give the title compound as a light-brown solid.

MS (ISP) 484.3 [(M+H)$^+$].

Example 37

[4-(3-Imidazol-1-yl-phenyl)-8-iodo-2-oxo-2,3-dihydro-1H-benzo[b][1,4]diazepin-7-yl]-acetonitrile The title compound was prepared from {5-cyanomethyl-2-[3-(3-imidazol-1-yl-phenyl)-3-oxo-propionylamino]-4-iodo-phenyl}-carbamic acid tert.-butyl ester (Example M21) (520 mg, 0.89 mmol) by treatment with TFA in $CH_2Cl_2$ according to the general procedure N. Obtained as a light pink solid (297 mg).

MS (EI) 467 (M$^+$); mp 243–245° C.

Example 38

4-[3-(2-Methyl-2H-pyrazol-3-yl)-phenyl]-7-morpholin-4-yl-8-trifluoromethyl-1,3-dihydro-benzo[b][1,4]diazepin-2-one The title compound was prepared from (2-{3-[3-(2-methyl-2H-pyrazol-3-yl)-phenyl]-3-oxo-propionylamino}-5-morpholin-4-yl-4-trifluoromethyl-phenyl)-carbamic acid tert.-butyl ester (Example M22) (100 mg, 0.17 mmol) by treatment with TFA in $CH_2Cl_2$ according to the general procedure N. Obtained as an off-white solid (32 mg).

MS (ISP) 470 [(M+H)$^+$]; mp 211° C.

Example 39

4-[3-(3-Hydroxymethyl-isoxazol-5-yl)-phenyl]-7-morpholin-4-yl-8-trifluoromethyl-1,3-dihydro-benzo[b][1,4]diazepin-2-one The title compound was prepared from (RS)-[5-morpholin-4-yl-2-(3-oxo-3-{3-[3-(tetrahydro-pyran-2-yloxymethyl)-isoxazol-5-yl]-phenyl}-propionylamino)-4-trifluoromethyl-phenyl]-carbamic acid tert.-butyl ester (Example M23) (57 mg, 0.08 mmol) by treatment with TFA in $CH_2Cl_2$ according to the general procedure N. Obtained as an off-white solid (11 mg).

MS (ISP) 487 [(M+H)$^+$]; mp 196° C.

Example 40

4-[3-(5-Dimethylaminomethyl-[1,2,3]triazol-1-yl)-phenyl]-7-morpholin-4-yl-8-trifluoromethyl-1,3-dihydro-benzo[b][1,4]diazepin-2-one The title compound was prepared from (2-{3-[3-(5-dimethylaminomethyl-[1,2,3]triazol-1-yl)-phenyl]-3-oxo-propionylamino}-5-morpholin-4-yl-4-trifluoromethyl-phenyl)-carbamic acid tert.-butyl ester (Example M24) (138 mg, 0.218 mmol) by treatment with TFA in $CH_2Cl_2$ according to the general procedure N. Obtained as a beige solid (37 mg).

MS (ISP) 514 [(M+H)$^+$]; mp 180° C.

Example 41

4-[3-(3-Methyl-isoxazol-5-yl)-phenyl]-7-thiomorpholin-4-yl-8-trifluoromethyl-1,3-dihydro-benzo[b][1,4]diazepin-2-one The title compound was prepared from (2-{3-[3-(3-methyl-isoxazol-5-yl)-phenyl]-3-oxo-propionylamino}-5-thiomorpholin-4-yl-4-trifluoromethyl-phenyl)-carbamic acid tert.-butyl ester (Example M25) (310 mg, 0.5 mmol) by treatment with TFA in $CH_2Cl_2$ according to the general procedure N. Obtained as a yellow solid (80 mg).

MS (ISP) 487.2 [(M+H)$^+$]; mp 230–233° C.

Example 42

4-(4-oxo-8-Thiomorpholin-4-yl-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-thiomorpholin-4-yl-4-trifluoromethyl-phenyl}-carbamic acid tert.-butyl ester (Example M26) (265 mg, 0.5 mmol) by treatment with TFA in $CH_2Cl_2$ according to the general procedure N. Obtained as a yellow solid (111 mg).

MS (EI) 431.1 (M$^+$); mp 195–199° C.

Example 43

7-(1,1-Dioxo-11 6-Thiomorpholin-4-yl)-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-(1,1-dioxo-11 6-thiomorpholin-4-yl)-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M27) by treatment with TFA in $CH_2Cl_2$ according to the general procedure N. Obtained as a light yellow solid (115 mg).

MS (ISP) 535.2 [(M+H)$^+$]; mp 216° C. (dec.).

Example 44

4-(8-Methoxy-4-oxo-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-methoxy-4-trifluoromethyl-phenyl}-carbamic acid tert.-butyl ester (Example M28) (293 mg, 0.61 mmol) by treatment with TFA in $CH_2Cl_2$ according to the general procedure N. Obtained as a yellow solid (180 mg).

MS (EI) 360 (M$^+$); mp 227° C.

Example 45

7-Methoxy-4-[3-(3-methyl-isoxazol-5-yl)-phenyl]-8-trifluoromethyl-1,3-dihydro-benzo[b][1,4]diazepin-2-one The title compound was prepared from (5-methoxy-2-{3-[3-(3-methyl-isoxazol-5-yl)-phenyl]-3-oxo-propionylamino}-4-trifluoromethyl-phenyl)-carbamic acid tert.-butyl ester (Example M29) (254 mg, 0.48 mmol) by treatment with TFA in $CH_2Cl_2$ according to the general procedure N. Obtained as an off-white solid (96 mg).

MS (ISP) 416 [(M+H)$^+$]; mp 225° C.

Example 46

4-[3-(5-Hydroxymethyl-1,2,3]triazol-1-yl)-phenyl]-7-methoxy-8-trifluoromethyl-1,3-dihydro-benzo[b][1,4]diazepin-2-one The title compound was prepared from (RS)-[5-methoxy-2-(3-oxo-3-{3-[5-(tetrahydro-pyran-2-yloxymethyl)-[1,2,3]

triazol-1-yl]-phenyl}-propionylamino)-4-trifluoromethyl-phenyl]-carbamic acid tert.-butyl ester (Example M30) (404 mg, 0.64 mmol) by treatment with TFA in CH$_2$Cl$_2$ according to the general procedure N. Obtained as a yellow solid (134 mg).

MS (ISP) 432 [(M+H)$^+$]; mp 225° C.

Example 47

7-Methoxy-4-[3-(5-pyrrolidin-1-ylmethyl-[1,2,3]triazol-1-yl)-phenyl]-8-trifluorometyl-1,3-dihydro-benzo[b][1,4]diazepin-2-one The title compound was prepared from 4-[3-(5-hydroxymethyl-[1,2,3]triazol-1-yl)-phenyl]-7-methoxy-8-trifluoromethyl-1,3-dihydro-benzo[b][1,4]diazepin-2-one (Example 46) (86 mg, 0.2 mmol) by treatment with SOCl$_2$ (0.044 mL, 0.6 mmol) in CH$_2$Cl$_2$ (2 mL) from 23° C. to reflux for 15 min, followed by evaporation to dryness. The crude chloride was dissolved in DMF (2 mL) and stirred with cat. amount of NaI and pyrrolidine (0.17 mL, 2.0 mmol) at 23° C. until tlc indicated complete conversion of the chloride. The reaction mixture was taken up in EtOAc, washed with water and brine, dried over Na$_2$SO$_4$. Removal of the solvent in vacuum left a yellow semisolid, which was purified by silica gel column chromatography. Obtained as a yellow solid (47 mg).

MS (ISP) 485 [(M+H)$^+$]; mp 215° C.

Example 48

4-[3-(5-Hydroxymethyl-isoxazol-3-yl)-phenyl]-7-morpholin-4-yl-8-trifluoromethyl-1,3-dihydro-benzo[b][1,4]diazepin-2-one The title compound was prepared from (RS)-[5-morpholin-4-yl-2-(3-oxo-3-{3-[5-(tetrahydro-pyran-2-yloxymethyl)-isoxazol-3-yl]-phenyl}-propionylamino)-4-trifluoromethyl-phenyl]-carbamic acid tert.-butyl ester (Example M31) by treatment with TFA in CH$_2$Cl$_2$ according to the general procedure N. Obtained as a white solid (386 mg).

MS (ISP) 467.3 [(M+H)$^+$]; mp 237–238° C.

Example 49

7-Morpholin-4-yl-4-(3-pyrazol-1-yl-phenyl)-8-trifluoromethyl-1,3-dihydro-benzo[b][1,4]diazepin-2-one The title compound was prepared from {5-morpholin-4-yl-2-[3-oxo-3-(3-pyrazol-1-yl-phenyl)-propionylamino]-4-trifluoromethyl-phenyl}-carbamic acid tert.-butyl ester (Example M32) (322 mg, 0.56 mmol) by treatment with TFA in CH$_2$Cl$_2$ according to the general procedure N. Obtained as an off-white solid (146 mg).

MS (ISP) 456 [(M+H)$^+$]; mp 166° C.

Example 50

7-Morpholin-4-yl-4-(3-[1,2,4]triazol-4-yl-phenyl)-8-trifluoromethyl-1,3-dihydro-benzo[b][1,4]diazepin-2-one The title compound was prepared from {5-morpholin-4-yl-2-[3-oxo-3-(3-[1,2,4]triazol-4-yl-phenyl)-propionylamino]-4-trifluoromethyl-phenyl}-carbamic acid tert.-butyl ester (Example M33) (360 mg, 0.627 mmol) by treatment with TFA in CH$_2$Cl$_2$ according to the general procedure N. Obtained as a yellow solid (176 mg).

MS (ISP) 457.4 [(M+H)$^+$]; mp 233–236° C.

Example 51

7-Fluoro-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-fluoro-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M34) (489 mg, 0.787 mmol) by treatment with TFA in CH$_2$Cl$_2$ according to the general procedure N. Obtained as a light yellow solid (87 mg).

MS (ISN) 418.1 [(M–H)$^-$]; mp 197–199° C.

Example 52

7-Ethoxy-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-ethoxy-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert.-butyl ester (Example M35) (876 mg, 1.35 mmol) by treatment with TFA in CH$_2$Cl$_2$ according to the general procedure N. Obtained as a yellow solid (360 mg).

MS (ISP) 446 [(M+H)$^+$]; mp 214° C.

Example 53

4-(8-Ethoxy-4-oxo-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-ethoxy-4-trifluoromethyl-phenyl}-carbamic acid tert-butyl ester (Example M36) (133 mg, 0.27 mmol) by treatment with TFA in CH$_2$Cl$_2$ according to the general procedure N. Obtained as an off-white solid (28 mg).

MS (ISN) 373 [(M–H)$^-$]; mp 233° C.

Example 54

4-[3-(5-Cyclopropylaminomethyl-[1,2,3]triazol-1-yl)-phenyl]-7-ethoxy-8-trifluoromethyl-1,3-dihydro-benzo[b][1,4]diazepin-2-one The title compound was prepared from 7-ethoxy-4-[3-(5-hydroxymethyl-[1,2,3]triazol-1-yl)-phenyl]-8-trifluoromethyl-1,3-dihydro-benzo[b][1,4]diazepin-2-one (Example 52) (134 mg, 0.3 mmol) by treatment with SOCl$_2$ (3 eq.) and cyclopropylamine (10 eq.) as described in Example 47. Obtained as a yellow solid (55 mg).

MS (ISN) 483 [(M–H)$^-$]; mp 80° C.

Example 55

7-Ethoxy-4-(3-{5-](2,2,2-trifluoro-ethylamino)-methyl]-[1,2,3]triazol-1-yl}-phenyl)-8-trifluoromethyl-1,3-dihydro-benzo[b][1,4]diazepin-2-one The title compound was prepared from 7-ethoxy-4-[3-(5-hydroxymethyl-[1,2,3]triazol-1-yl)-phenyl]-8-trifluoromethyl-1,3-dihydro-benzo[b][1,4]diazepin-2-one (Example 52) (134 mg, 0.3 mmol) by treatment with $SOCl_2$ (3 eq.) and 2,2,2-trifluoroethylamine (20 eq.) as described in Example 47. Obtained as an off-white solid (57 mg).

MS (ISP) 527 [(M+H)+]; mp 135° C.

Example 56

7-Ethoxy-4-(3-[1,2,3]triazol-1-yl-phenyl)-8-trifluoromethyl-1,3-dihydro-benzo[b][1,4]diazepin-2-one The title compound was prepared from {5-ethoxy-2-[3-oxo-3-(3-[1,2,3]triazol-1-yl-phenyl)-propionylamino]-4-trifluoromethyl-phenyl}-carbamic acid tert.-butyl ester (Example M37) (203 mg, 0.38 mmol) by treatment with TFA in $CH_2Cl_2$ according to the general procedure N. Obtained as an off-white solid (148 mg).

MS (ISP) 416 [(M+H)+]; mp 215° C.

Example 57

7-Methoxy-4-(3-[1,2,3]triazol-1-yl-phenyl)-8-trifluoromethyl-1,3-dihydro-benzo[b][1,4]diazepin-2-one The title compound was prepared from {5-methoxy-2-[3-oxo-3-(3-[1,2,3]triazol-1-yl-phenyl)-propionylamino]-4-trifluoromethyl-phenyl}-carbamic acid tert.-butyl ester (Example M38) (394 mg, 0.758 mmol) by treatment with TFA in $CH_2Cl_2$ according to the general procedure N. Obtained as a light brown solid (169 mg).

MS (ISN) 400.3 [(M−H)−].

Example 58

4-(8-Methyl-4-oxo-7-trifluoromethyl-4,5-dihydro-3H-benzo[b][1,4]diazepin-2-yl)-pyridine-2-carbonitrile The title compound was prepared from {2-[3-(2-cyano-pyridin-4-yl)-3-oxo-propionylamino]-5-methyl-4-trifluoromethyl-phenyl}-carbamic acid tert.-butyl ester (Example M39) by treatment with TFA in $CH_2Cl_2$ according to the general procedure N. Obtained as a light yellow solid (113 mg).

MS (ISN) 343.0 [(M−H)−]; mp 235° C.

Example 59

2-(3-Cyano-phenyl)-8-morpholin-4-yl-4-oxo-4,5-dihydro-3H-benzo[b][1,4]diazepine-7-carbonitrile The title compound was prepared from {5-Cyano-2-[3-(3-cyano-phenyl)-3-oxo-propionylamino]-4-morpholin-4-yl-phenyl}-carbamic acid tert-butyl ester (Example M40) (0.28 g, 0.57 mmol) by treatment with TFA in $CH_2Cl_2$ according to the general procedure N. Obtained as a yellow solid (130 mg, 61%).

MS (ISP) 372.2 [(M+H)+]; mp 259° C.

Example 60

2-[3-(5-Hydroxymethyl-[1,2,3]triazol-1-yl)-phenyl]-8-morpholin-4-yl-4-oxo-4,5-dihydro-3H-benzo[b][1,4]diazepine-7-carbonitrile The title compound was prepared from (RS)-[4-cyano-5-morpholin-4-yl-2-(3-oxo-3-{3-[5-(tetrahydro-pyran-2-yloxymethyl)-[1,2,3]triazol-1-yl]-phenyl}-propionylamino)-phenyl]-carbamic acid tert-butyl ester (Example M41) (0.36 g, 0.56 mmol) by treatment with TFA in $CH_2Cl_2$ according to the general procedure N. Obtained as a yellow solid (152 mg, 61%).

MS (ISP) 444.3 [(M+H)+]; mp 180° C.

Example 61

2-[3-(3-Methyl-isoxazol-5-yl)-phenyl]-8-morpholin-4-yl-4-oxo-4,5-dihydro-3H-benzo[b][1,4]diazepine-7-carbonitrile The title compound was prepared from (4-cyano-2-{3-[3-(3-methyl-isoxazol-5-yl)-phenyl]-3-oxo-propionylamino}-5-morpholin-4-yl-phenyl)-carbamic acid tert-butyl ester (Example M42) (0.39 g, 0.71 mmol) by treatment with TFA in $CH_2Cl_2$ according to the general procedure N. Obtained as a light yellow solid (215 mg, 70%).

MS (ISP) 428.5 [(M+H)+]; mp 252° C.

Example 62

2-[3-(3-Methyl-isoxazol-5-yl)-phenyl]-4-oxo-8-thiomorpholin-4-yl-4,5-dihydro-3H-benzo[b][1,4]diazepine-7-carbonitrile The title compound was prepared from (4-cyano-2-{3-[3-(3-methyl-isoxazol-5-yl)-phenyl]-3-oxo-propionylamino}-5-morpholin-4-yl-phenyl)-carbamic acid tert-butyl ester (Example M42) (0.43 g, 0.77 mmol) by treatment with TFA in $CH_2Cl_2$ according to the general procedure N. Obtained as a light yellow solid (280 mg, 82%).

MS (ISP) 444.3 [(M+H)+]; mp 245° C.

Example 63

7-Chloro-4-[3-(5-hydroxymethyl-[1,2,3]triazol-1-yl)-phenyl]-8-trifluoromethyl-1,3-dihydro-benzo[b][1,4]diazepin-2-one The title compound was prepared from (RS)-[5-chloro-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester (Example M44) (0.79 g, 1.24 mmol) by treatment with TFA in $CH_2Cl_2$ according to the general procedure N. Obtained as an off-white solid (350 mg, 65%).

MS (ISP) 436.4 [(M+H)+]; mp 198° C.

Example 64

7-Chloro-4-[3-(5-hydroxymethyl-[1,2,4]triazol-1-yl)-phenyl]-8-trifluoromethyl-1,3-dihydro-benzo[b][1,4]diazepin-2-one The title compound was prepared from (RS)-[5-chloro-2-(3-oxo-3-{3-[5-(tetrahydro-pyran-2-yloxymethyl)-[1,2,4]triazol-1-yl]-phenyl}-propionylamino)-4-trifluoromethyl-phenyl]-carbamic acid tert-butyl ester (Example M55) (0.78 g, 1.22 mmol) by treatment with TFA in $CH_2Cl_2$ according to the general procedure N. Obtained as a light brown solid (370 mg, 70%).

MS (ISP) 436.4 [(M+H)+]; mp 212° C.

Example 65

7-Chloro-4-[3-(3-methyl-isoxazol-5-yl)-phenyl]-8-trifluoromethyl-1,3-dihydro-benzo[b][1,4]diazepin-2-one The title compound was prepared from (5-chloro-2-{3-[3-(3-methyl-isoxazol-5-yl)-phenyl]-3-oxopropionylamino}-4-trifluoromethyl-phenyl)-carbamic acid tert-butyl ester (Example M45) (0.20 g, 0.37 mmol) by treatment with TFA in CH$_2$Cl$_2$ according to the general procedure N. Obtained as an off-white solid (131 mg, 84%).

MS (ISP) 418.1 [(M–H)$^-$]; mp 252° C.

Example 66

7-Chloro-4-[3-(5-cyclopropylaminomethyl-[1,2,4]triazol-1-yl)-phenyl]-8-trifluoromethyl-1,3-dihydro-benzo[b][1,4]diazepin-2-one The title compound was prepared from 7-chloro-4-[3-(5-hydroxymethyl-[1,2,4]triazol-1-yl)-phenyl]-8-trifluoromethyl-1,3-dihydro-benzo[b][1,4]diazepin-2-one (Example 63) (218 mg, 0.50 mmol) by reaction with thionylchloride in dichloromethane and subsequent treatment of the corresponding chloride with cyclopropylamine in DMF as described in Example 47. Obtained as an off-white solid (135 mg, 57%).

MS (ISP) 475.3 [(M+H)$^+$]; mp 191° C.

Example 67

7-Chloro-4-[3-(5-cyclopropylaminomethyl-[1,2,3]triazol-1-yl)-phenyl]-8-trifluoromethyl-1,3-dihydro-benzo[b][1,4]diazepin-2-one The title compound was prepared from 7-chloro-4-[3-(5-hydroxymethyl-[1,2,3]triazol-1-yl)-phenyl]-8-trifluoromethyl-1,3-dihydro-benzo[b][1,4]diazepin-2-one (Example 63) (218 mg, 0.50 mmol) by reaction with thionylchloride in dichloromethane and subsequent treatment of the corresponding chloride with cyclopropylamine in DMF as described in Example 47. Obtained as a light yellow solid (130 mg, 55%).

MS (ISP) 475.3 [(M+H)$^+$]; mp 206° C.

Example 68

4-[3-(5-Hydroxymethyl-[1,2,3]triazol-1-yl)-phenyl]-7-methyl-8-trifluoromethyl-1,3-dihydro-benzo[b][1,4]diazepin-2-one The title compound was prepared from (RS)-[5-methyl-2-(3-oxo-3-{3-[5-(tetrahydro-pyran-2-yloxymethyl)-[1,2,3]triazol-1-yl]-phenyl}-propionylamino)-4-trifluoromethyl-phenyl]-carbamic acid tert-butyl ester (Example M46) (0.90 g, 1.46 mmol) by treatment with TFA in CH$_2$Cl$_2$ according to the general procedure N. Obtained as an off-white solid (400 mg, 66%).

MS (ISP) 416.4 [(M+H)$^+$]; mp 215° C.

Example 69

4-[3-(5-Cyclopropylaminomethyl-[1,2,3]triazol-1-yl)-phenyl]-7-methyl-8-trifluoromethyl-1,3-dihydro-benzo[b][1,4]diazepin-2-one Prepared from 4-[3-(5-hydroxymethyl-[1,2,3]triazol-1-yl)-phenyl]-7-methyl-8-trifluoromethyl-1,3-dihydro-benzo[b][1,4]diazepin-2-one (Example 68) (208 mg, 0.50 mmol) by reaction with thionylchloride in dichloromethane and subsequent treatment of the corresponding chloride with cyclopropylamine in DMF according to the method described in Example 47. Obtained as a light yellow solid (155 mg, 68%).

MS (ISP) 455.3 [(M+H)$^+$]; mp 181° C.

Example 70

7-Methyl-4-[3-(3-methyl-isoxazol-5-yl)-phenyl]-8-trifluoromethyl-1,3-dihydro-benzo[b][1,4]diazepin-2-one The title compound was prepared from (5-methyl-2-{3-[3-(3-methyl-isoxazol-5-yl)-phenyl]-3-oxo-propionylamino}-4-trifluoromethyl-phenyl)-carbamic acid tert-butyl ester (Example M47) (0.23 g, 0.44 mmol) by treatment with TFA in CH$_2$Cl$_2$ according to the general procedure N. Obtained as an off-white solid (157 mg, 88%).

MS (ISP) 398.1 [(M–H)$^-$]; mp 240° C.

Example 71

7-Chloro-4-(3-[1,2,4]triazol-1-yl-phenyl)-8-trifluoromethyl-1,3-dihydro-benzo[b][1,4]diazepin-2-one The title compound was prepared from {5-chloro-2-[3-oxo-3-(3-[1,2,4]triazol-1-yl-phenyl)-propionylamino]-4-trifluoromethyl-phenyl}-carbamic acid tert-butyl ester (Example M48) (0.35 g, 0.67 mmol) by treatment with TFA in CH$_2$Cl$_2$ according to the general procedure N. Obtained as a light yellow solid (211 mg, 78%).

MS (ISP) 406.4 [(M+H)$^+$]; mp 258° C.

Example 72

7-Chloro-4-(3-imidazol-1-yl-phenyl)-8-trifluoromethyl-1,3-dihydro-benzo[b][1,4]diazepin-2-one The title compound was prepared from {5-chloro-2-[3-(3-imidazol-1-yl-phenyl)-3-oxo-propionylamino]-4-trifluoromethyl-phenyl]-carbamic acid tert-butyl ester (Example M49) (0.15 g, 0.29 mmol) by treatment with TFA in CH$_2$Cl$_2$ according to the general procedure N. Obtained as a light yellow solid (55 mg, 47%).

MS (ISP) 405.4 [(M+H)$^+$]; mp 225° C.

Example 73

7-Chloro-4-(3-[1,2,3]triazol-1-yl-phenyl)-8-trifluoromethyl-1,3-dihydro-benzo[b][1,4]diazepin-2-one The title compound was prepared from {5-chloro-2-[3-oxo-3-(3-[1,2,3]triazol-1-yl-phenyl)-propionylamino]-4-trifluoromethyl-phenyl}-carbamic acid tert-butyl ester (Example M50) (0.33 g, 0.63 mmol) by treatment with TFA in CH$_2$Cl$_2$ according to the general procedure N. Obtained as a light yellow solid (152 mg, 60%).

MS (ISP) 406.4 [(M+H)$^+$]; mp 219° C.

Example 74

7-Methyl-4-(3-[1,2,4]triazol-1-yl-phenyl)-8-trifluoromethyl-1,3-dihydro-benzo[b][1,4]diazepin-2-one The title compound was prepared from {5-methyl-2-[3-oxo-3-(3-[1,2,4]triazol-1-yl-phenyl)-propionylamino]-4-trifluoromethyl-phenyl}-carbamic acid tert-butyl ester (Example M51) (0.41 g, 0.81 mmol) by treatment with TFA in CH$_2$Cl$_2$ according to the general procedure N. Obtained as an off-white solid (255 mg, 81%).

MS (ISP) 386.3 [(M+H)$^+$]; mp 241° C.

Example 75

4-(3-Imidazol-1-yl-phenyl)-7-methyl-8-trifluoromethyl-1,3-dihydro-benzo[b][1,4]diazepin-2-one The title compound was prepared from {2-[3-(3-imidazol-1-yl-phenyl)-5-methyl-3-oxo-propionylamino]-4- trifluoromethyl-phenyl}-carbamic acid tert-butyl ester (Example M52) (0.37 g, 0.74 mmol) by treatment with TFA in CH$_2$Cl$_2$ according to the general procedure N. Obtained as an off-white solid (249 mg, 88%).

MS (ISP) 385.3 [(M+H)$^+$]; mp 212° C.

Example 76

7-Methyl-4-(3-[1,2,3]triazol-1-yl-phenyl)-8-trifluoromethyl-1,3-dihydro-benzo[b][1,4]diazepin-2-one The title compound was prepared from {5-methyl-2-[3-oxo-3-(3-[1,2,3]triazol-1-yl-phenyl)-propionylamino]-4-trifluoromethyl-phenyl}-carbamic acid tert-butyl ester (Example M53) (0.29 g, 0.58 mmol) by treatment with TFA in CH$_2$Cl$_2$ according to the general procedure N. Obtained as an off-white solid (143 mg, 64%).

MS (ISP) 386.3 [(M+H)$^+$]; mp 237° C.

Example 77

7-Methyl-4-(3-pyrazol-1-yl-phenyl)-8-trifluoromethyl-1,3-dihydro-benzo[b][1,4]diazepin-2-one The title compound was prepared from {5-methyl-2-[3-oxo-3-(3-pyrazol-1-yl-phenyl)-propionylamino]-4-trifluoromethyl-phenyl}-carbamic acid tert-butyl ester (Example M54) (0.36 g, 0.72 mmol) by treatment with TFA in CH$_2$Cl$_2$ according to the general procedure N. Obtained as a white solid (182 mg, 66%).

MS (ISP) 385.2 [(M+H)$^+$]; mp 235° C.

Example 78

Acetic Acid 2-[3-(4-oxo-7-Pyrrol-1-yl-4,5-dihydro-3H-benzo[b][1,4]diazepin-2-yl)-phenyl]-oxazol-4-ylmethyl Ester
4-[3-(4-Chloromethyl-oxazol-2-yl)-phenyl]-8-pyrrol-1-yl-1,3-dihydro-benzo[b][1,4]diazepin-2-one A suspension of 4-[3-(4-hydroxymethyl-oxazol-2-yl)-phenyl]-8-pyrrol-1-yl-1,3-dihydro-benzo[b][1,4]diazepin-2-one (Example 26) (1.0 g) in CH$_2$Cl$_2$ (15 mL) and thionyl chloride (0.27 mL) was heated with stirring to 40° C. for 0.5 h and subsequently cooled in the ice bath. The solid was isolated by filtration and washed with CH$_2$Cl$_2$ to give 4-[3-(4-chloromethyl-oxazol-2-yl)-phenyl]-8-pyrrol-1-yl-1,3-dihydro-benzo[b][1,4]diazepin-2-one (1.0 g) as yellow crystals.
Acetic Acid 2-3-(4-oxo-7-Pyrrol-1-yl-4,5-dihydro-3H-benzo[b][1,4]diazepin-2-yl)-phenyl}-oxazol-4-ylmethyl Ester A mixture of 4-[3-(4-chloromethyl-oxazol-$^2$-yl)-phenyl]-8-pyrrol-1-yl-1,3-dihydro-benzo[b][1,4]diazepin-2-one (146 mg), AcOK (52 mg) and KI (6 mg) in N,N-dimethylformamide (1 mL) was heated to 100° C. for 0.5 h. The mixture was cooled and diluted with H$_2$O. The precipitate formed was isolated by filtration and purified by chromatography on silica gel using AcOEt/CH$_2$Cl$_2$ (2:1, v/v) as eluent to give the title compound (45 mg) as yellow solid.

MS (ISP) 458.3 [(M+NH4)$^+$]; mp 206–207° C.

Example 79

4-[3-(4-Methylaminomethyl-oxazol-2-yl)-phenyl]-8-pyrrol-1-yl-1,3-dihydro-benzo[b][1,4]diazepin-2-one A mixture of 4-[3-(4-chloromethyl-oxazol-2-yl)-phenyl]-8-pyrrol-1-yl-1,3-dihydro-benzo[b][1,4]diazepin-2-one (Example 78a) (125 mg) and potassium iodide (5 mg) in a 8M solution of methylamine in ethanol (1.5 mL) was stirred at 20° C. for 16 h. H$_2$O (20 mL) was added and the precipitated collected by filtration and purified by chromatography on silica gel using MeOH as eluent. The product was stirred with 20% aqueous MeOH (10 mL) the pH of the mixture being set to 11 by addition of 1N NaOH solution, and the solid was isolated by filtration to give the title compound (54 mg) as yellow solid.

S (ISP) 412.3 [(M+H)$^+$]; mp 182–183° C.

Example 80

4-[3-(4-Dimethylaminomethyl-oxazol-2-yl)-phenyl]-8-pyrrol-1-yl-1,3-dihydro-benzo[b][1,4]diazepin-2-one A mixture of 4-[3-(4-chloromethyl-oxazol-2-yl)-phenyl]-8-pyrrol-1-yl-1,3-dihydro-benzo[b][1,4]diazepin-2-one (Example 78a) (125 mg) and KI (5 mg) in a 5.6M solution of dimethylamine in EtOH (1.5 mL) was stirred at 20° C. for 16 h. H$_2$O (20 mL) was added and the precipitate was collected by filtration and purified by chromatography on silica gel using MeOH as eluent. The product was stirred with 20% aqueous MeOH (10 mL) the pH of the mixture being set to 11 by addition of 1N NaOH solution, and the solid was isolated by filtration to give the title compound (50 mg) as yellow solid.

MS (ISP) 426.5 [(M+H)$^+$]; mp 172–175° C.

Example 81

4-[3-(4-Morpholin-4-ylmethyl-oxazol-2-yl)-phenyl]-8-pyrrol-1-yl-1,3-dihydro-benzo[b][1,4]diazepin-2-one A mixture of 4-[3-(4-chloromethyl-oxazol-2-yl)-phenyl]-8-pyrrol-1-yl-1,3-dihydro-benzo[b][1,4]diazepin-2-one (Example 78a) (125 mg), morpholine (0.25 mL) and KI (5 mg) in EtOH (1 mL) was stirred at 60° C. for 2 h. in H$_2$O (20 mL) was added to the cooled solution and the precipitate was collected by filtration and purified by chromatography on silica gel using MeOH as eluent. The product was stirred with 20% aqueous MeOH (10 mL) the pH of the mixture being set to 11 by addition of 1N NaOH solution, and solid was subsequently isolated by filtration to give the title compound (60 mg) as yellow solid.

MS (ISP) 468.3 [(M+H)$^+$]; mp. 166–167° C.

Example 82

4-(4-oxo-7-Pyrrol-1-yl-4,5-dihydro-3H-benzo[b][1,4]diazepin-2-yl)-pyridine-2-carbonitrile A mixture of (2-amino-4-pyrrol-1-yl-phenyl)-carbamic acid tert-butyl ester (Example J2) (0.14 g) and 3-(2-cyano-pyridin-4-yl)-3-oxo-propionic acid tert-butyl ester (Example K3) (0.14 g) in toluene (1.5 mL) was heated to 100° C. for 4 h, a fine precipitate being formed. The mixture was cooled and the precipitae was isolated by filtration. A solution of this solid in CH$_2$Cl$_2$ (2.5 mL) and TFA (2.5 mL) was stirred for 0.5 h at 20° C. and then evaporated in vacuum. The residual oil was dissolved in AcOEt and the solution was washed with saturated Na$_2$CO$_3$ solution and with brine, dried over Na$_2$SO$_4$ and evaporated in vacuum. The solid residue was triturated with CH$_2$Cl$_2$ to give the title compound (0.06 g) as light-yellow crystals.

MS (ISN) 325.8 [(M−H)$^-$]; mp 243–244° C.

Example 83

7-Methyl-4-[3-(5-methyl-oxazol-4-yl)-phenyl]-8-trifluoromethyl-1,3-dihydro-benzo[b][1,4]diazepin-2-one A mixture of (2-amino-5-methyl-4-trifluoromethyl-phenyl)-carbamic acid tert-butyl ester (Example J15) (0.145 g) and 3-oxo-[3-[(5-methyl-oxazol-4-yl)-phenyl]-propionic acid tert.-butyl ester (Example K17) (0.26 g) in toluene (1.5 mL) was heated to 100° C. for 8 h. The mixture was cooled and evaporated in vacuum. A solution of the residue in a mixture of $CH_2Cl_2$ (2.5 mL) and TFA (2.5 mL) was stirred for 0.5 h at 20° C. The mixture was evaporated in vacuum, the residual oil was dissolved in AcOEt and the solution was washed with saturated $NaHCO_3$ solution and with brine, dried over $Na_2SO_4$ and evaporated in vacuum. The residue was crystallized from $CH_2Cl_2$ to give the title compound (0.12 g) as white crystals.

MS (ISP) 444.0 [(M+H)$^+$]; mp. 241–242° C.

Example 84

4-[3-(2-Hydroxymethyl-5-methyl-thiazol-4-yl)-phenyl]-7-methyl-8-trifluoromethyl-1,3-dihydro-benzo[b][1,4]diazepin-2-one A mixture of (2-amino-5-methyl-4-trifluoromethyl-phenyl)-carbamic acid tert-butyl ester (Example J15) (0.145 g) and 3-[3-[5-methyl-2-(tetrahydro-pyran-2-yloxymethyl)-thiazol-4-yl]-phenyl]-3-oxo-propionic acid tert.-butyl ester (Example K18) (0.18 g) in toluene (1.5 mL) was heated to 100° C. for 8 h. The mixture was cooled and evaporated in vacuum. A solution of the residue in a mixture of $CH_2Cl_2$ (2.5 mL) and trifluoroacetic acid (2.5 mL) was stirred for 0.5 h at 20° C. The mixture was evaporated in vacuum, the residual oil was dissolved in AcOEt and the solution was washed with saturated $NaHCO_3$ solution and with brine, dried over $Na_2SO_4$ and evaporated in vacuum. The residue was triturated with $CH_2Cl_2$ to give the title compound (0.07 g) as white crystals.

MS (ISN) 444.0 [(M−H)$^-$]; mp 214–217° C.

Example 85

4-[3-(4-Hydroxymethyl-thiazol-2-yl)-phenyl]-7-methyl-8-trifluoromethyl-1,3-dihydro-benzo[b][1,4]diazepin-2-one A mixture of (2-amino-5-methyl-4-trifluoromethyl-phenyl)-carbamic acid tert-butyl ester (Example J15) (0.145 g) and 3-oxo-3-[3-[4-(tetrahydro-pyran-2-yloxymethyl)-thiazol-2-yl]-phenyl]-propionic acid tert.-butyl ester (Example K19) (0.23 g) in toluene (2 mL) was heated to 100° C. for 5 h. The mixture was cooled and evaporated in vacuum. A solution of the residue in a mixture of $CH_2Cl_2$ (2 mL) and TFA (2 mL) was stirred for 0.5 h at 20° C. The mixture was evaporated in vacuum, the residual oil was dissolved in AcOEt and the solution was washed with saturated $NaHCO_3$ solution and with brine, dried over $Na_2SO_4$ and evaporated in vacuum. The residue was crystallized from $CH_2Cl_2$/hexane to give the title compound (0.04 g) as light-brown crystals.

MS (ISP) 430.0 [(M−H)$^-$].

Example I

Tablets of the following composition are produced in a conventional manner:

| mg/Tablet | |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

| mg/Tablet | |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

| mg/Capsule | |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:
1. A compound of formula

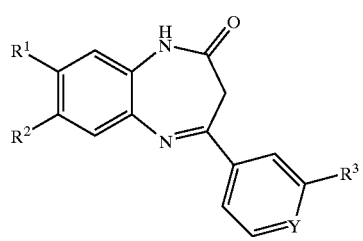

I wherein
  $R^1$ is selected from the group consisting of cyano,
    fluoro-lower alkyl,
    lower alkoxy,
    fluoro-lower alkoxy,
    unsubstituted pyrrol-1-yl, and pyrrol-1-yl substitued by between one to three substituents selected from the group consisting of
      fluoro, chloro, cyano, unsubstituted phenyl, or phenyl substituted by a substituent selected from the group consisting of halogen,
      —$(CH_2)_{1-4}$-hydroxy, fluoro-lower alkyl, lower alkyl,
      —$(CH_2)_n$-lower alkoxy,
      —$(CH_2)_n$—C(O)O—R", —$(CH_2)_{1-4}$—NR'R",
      hydroxy-lower alkoxy and
      —$(CH_2)_n$—CONR'R";
  $R^2$ is selected from the group consisting of
    halogen,
    hydroxy,
    lower alkyl,
    fluoro-lower alkyl,
    lower alkoxy,
    hydroxymethyl,
    hydroxyethoxy,
    lower alkoxy-(ethoxy)$_m$, wherein m=1 to 4,
    lower alkoxymethyl,
    cyanomethoxy,
    morpholine-4-yl,
    thiomorpholine-4-yl,
    1-oxothiomorpholine-4-yl,
    1,1-dioxothiomorpholine-4-yl,
    4-oxo-piperidine-1-yl
    4-alkoxy-piperidine-1-yl,
    4-hydroxy-piperidine-1-yl,
    4-hydroxyethoxy-piperidine-1-yl,
    4-lower alkyl-piperazine-1-yl,
    alkoxycarbonyl,
    2-dialkylamino-ethylsulfanyl,
    N,N-bis lower alkylamino lower alkyl,
    carbamoylmethyl,
    alkylsulfonyl
    lower alkoxycarbonyl-lower alkyl,
    alkylcarboxy-lower alkyl,
    carboxy-lower alkyl,
    alkoxycarbonylmethylsulfanyl,
    carboxymethylsulfanyl,
    1,4-dioxa-8-aza-spiro[4.5]dec-8-yl,
    carboxy-lower alkoxy,
    cyano-lower alkyl,
    2,3-dihydroxy-lower alkoxy,
    carbamoylmethoxy,
    2-oxo-[1,3]-dioxolan-4-yl-lower alkoxy,
    N-(2-hydroxy-lower alkyl)-N-lower alkyl amino,
    hydroxycarbamoyl-lower alkoxy,
    2,2-dimethyl-tetrahydro-[1,3]dioxolo[4,5c]-pyrrol-5-yl,
    lower alkoxy-carbamoyl-lower alkoxy,
    3R-hydroxy-pyrrolidin-1-yl,
    3,4-dihydroxy-pyrrolidin-1-yl,
    2-oxo-oxazolidin-3-yl,
    lower alkyl-carbamoylmethoxy,
    aminocarbamoyl-lower alkoxy, and, when $R^1$ is unsubstituted pyrrol-1-yl or
    pyrrol-1-yl substituted as defined above, hydrogen;
  Y is —CH= or =N—;
  $R^3$ is halogen,
    lower alkyl,
    fluoro-lower alkyl,
    lower alkoxy,
    cyano,
    —$(CH_2)_n$—C(O)—OR",
    —$(CH_2)_n$—C(O)—NR'R",
  or is an unsubstituted five-membered aromatic heterocycle or a five-membered aromatic heterocycle, substituted by halogen, fluoro-lower alkyl, fluoro-lower alkoxy, cyano, —$(CH_2)_n$—NR'R", —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, lower alkoxy, lower alkylthio, lower alkyl, or lower alkyl substituted by fluoro, hydroxy, lower alkoxy, cyano or carbamoyloxy;
  R' is selected from the group consisting of hydrogen,
    lower alkyl,
    $C_3$-$C_6$-cycloalkyl,
    fluoro-lower alkyl and
    2-lower alkoxy lower alkyl;
  R" is selected from the group consisting of hydrogen,
    lower alkyl,
    $C_3$-$C_6$-cycloalkyl,
    fluoro-lower alkyl,
    2-lower alkoxy lower alkyl,
    —$(CH_2)_{2-4}$-di-lower alkylamino,
    —$(CH_2)_{2-4}$-morpholinyl,
    —$(CH_2)_{2-4}$-pyrrolidinyl,
    —$(CH_2)_{2-4}$-piperidinyl and
    3-hydroxy-lower alkyl; and
  n is 0, 1, 2, 3 or 4;
or a pharmaceutically acceptable addition salt thereof.

2. A compound according to claim 1, wherein $R^1$ is trifluoromethyl.

3. A compound according to claim 2, wherein $R^2$ is morpholine.

4. A compound according to claim 3, wherein the compound is selected from the group consisting of
  4-(8-morpholin-4-yl-4-oxo-7-trifluoromethyl-4,5-dihydro-3H-benzo[b][1,4]diazepin-2-yl)-pyridine-2-carbonitrile,
  4-[3-(3-methyl-isoxazol-5-yl)-phenyl]-7-morpholin-4-yl-8-trifluoromethyl-1,3-dihydro-benzo[b][1,4]diazepin-2-one,
  4-[3-(2-methyl-2H-pyrazol-3-yl)-phenyl]-7-morpholin-4-yl-8-trifluoromethyl-1,3-dihydro-benzo[b][1,4]diazepin-2-one,
  4-[3-(3-hydroxymethyl-isoxazol-5-yl)-phenyl]-7-morpholin-4-yl-8-trifluoromethyl-1,3-dihydro-benzo[b][1,4]diazepin-2-one, and
  4-[3-(5-hydroxymethyl-isoxazol-3-yl)-phenyl]-7-morpholin-4-yl-8-trifluoromethyl-1,3-dihydro-benzo[b][1,4]diazepin-2-one.

5. A compound according to claim 2, wherein $R^2$ is thiomorpholine.

6. A compound according to claim 5, wherein the compounds are selected from the group consisting of
  4-[3-(3-methyl-isoxazol-5-yl)-phenyl]-7-thiomorpholin-4-yl-8-trifluoromethyl-1,3-dihydro-benzo[b][1,4]diazepin-2-one, and
  4-(4-oxo-8-thiomorpholin-4-yl-7-trifluoromethyl-4,5-dihydro-3H-benzo[b][1,4]diazepin-2-yl)-pyridine-2-carbonitrile.

7. A compound according to claim 2, wherein $R^2$ is lower alkoxy.

8. A compound according to claim 7, wherein the compound is selected from the group consisting of
  7-methoxy-4-[3-(3-methyl-isoxazol-5-yl)-phenyl]-8-trifluoromethyl-1,3-dihydro-benzo[b][1,4]diazepin-2-one,
  7-methoxy-4-[3-(5-pyrrolidin-1-ylmethyl-[1,2,3]triazol-1-yl)-phenyl]-8-trifluoromethyl-1,3-dihydro-benzo[b][1,4]diazepin-2-one, 4-(8-ethoxy-4-oxo-7-trifluoromethyl-4,5-dihydro-3H-benzo[b][1,4]diazepin-2-yl)-pyridine-2-carbonitrile, 4-[3-(5-cyclopropylaminomethyl-[1,2,3]triazol-1-yl)-phenyl]-7-ethoxy-8-trifluoromethyl-1,3-dihydro-benzo[b][1,4]diazepin-2-one, 7-ethoxy-4-(3-{5-[(2,2,2-trifluoro-ethylamino)-methyl]-[1,2,3]triazol-1-yl}-phenyl)-8-trifluoromethyl-1,3-dihydro-benzo[b][1,4]diazepin-2-one, 7-ethoxy-4-(3-[1,2,3]triazol-1-yl-phenyl)-8-trifluoromethyl-1,3-dihydro-benzo[b][1,4]diazepin-2-one, and 7-methoxy-4-(3-[1,2,3]triazol-1-yl-phenyl)-8-trifluoromethyl-1,3-dihydro-benzo[b][1,4]diazepin-2-one.

9. A compound according to claim 2, wherein $R^2$ is lower alkyl or halogen.

10. A compound according to claim 9, wherein the compound is selected from the group consisting of 4-(8-methyl-4-oxo-7-trifluoromethyl-4,5-dihydro-3H-benzo[b][1,4]diazepin-2-yl)-pyridine-2-carbonitrile, 7-chloro-4-[3-(3-methyl-isoxazol-5-yl)-phenyl]-8-trifluoromethyl-1,3-dihydro-benzo[b][1,4]diazepin-2-one, 7-chloro-4-[3-(5-cyclopropylaminomethyl-[1,2,3]triazol-1-yl)-phenyl]-8-trifluoromethyl-1,3-dihydro-benzo[b][1,4]diazepin-2-one, 4-[3-(5-cyclopropylaminomethyl-[1,2,3]triazol-1-yl)-phenyl]-7-methyl-8-trifluoromethyl-1,3-dihydro-benzo[b][1,4]diazepin-2-one, 7-methyl-4-[3-(3-methyl-isoxazol-5-yl)-phenyl]-8-trifluoromethyl-1,3-dihydro-benzo[b][1,4]diazepin-2-one, 7-chloro-4-(3-[1,2,4]triazol-1-yl-phenyl)-8-trifluoromethyl-1,3-dihydro-benzo[b][1,4]diazepin-2-one, 7-chloro-4-(3-imidazol-1-yl-phenyl)-8-trifluoromethyl-1,3-dihydro-benzo[b][1,4]diazepin-2-one, 7-chloro-4-(3-[1,2,3]triazol-1-yl-phenyl)-8-trifluoromethyl-1,3-dihydro-benzo[b][1,4]diazepin-2-one, 7-methyl-4-(3-[1,2,4]triazol-1-yl-phenyl)-8-trifluoromethyl-1,3-dihydro-benzo[b][1,4]diazepin-2-one, 4-(3-imidazol-1-yl-phenyl)-7-methyl-8-trifluoromethyl-1,3-dihydro-benzo[b][1,4]diazepin-2-one, 7-methyl-4-(3-[1,2,3]triazol-1-yl-phenyl)-8-trifluoromethyl-1,3-dihydro-benzo[b][1,4]diazepin-2-one, 4-[3-(2-hydroxymethyl-5-methyl-thiazol-4-yl)-phenyl]-7-methyl-8-trifluoromethyl-1,3-dihydro-benzo[b][1,4]diazepin-2-one, and 4-[3-(4-hydroxymethyl-thiazol-2-yl)-phenyl]-7-methyl-8-trifluoromethyl-1,3-dihydro-benzo[b][1,4]diazepin-2-one.

11. A compound according to claim 1, wherein $R^1$ is unsubstituted pyrrol-1-yl.

12. A compound according to claim 11, wherein $R^2$ is selected from the group consisting of hydrogen, halogen, lower alkoxy-ethoxy and lower alkoxy.

13. A compounds according to claim 12, wherein the compound is selected from the group consisting of 4-(3-iodo-phenyl)-8-pyrrol-1-yl-1,3-dihydro-benzo[b][1,4]diazepin-2-one, 4-(3-imidazol-1-yl-phenyl)-8-pyrrol-1-yl-1,3-dihydro-benzo[b][1,4]diazepin-2-one, 4-[3-(4-hydroxymethyl-thiazol-2-yl)-phenyl]-8-pyrrol-1-yl-1,3-dihydro-benzo[b][1,4]diazepin-2-one, 8-pyrrol-1-yl-4-(3-[1,2,3]triazol-1-yl-phenyl)-1,3-dihydro-benzo[b][1,4]diazepin-2-one, 4-(3-oxazol-2-yl-phenyl)-8-pyrrol-1-yl-1,3-dihydro-benzo[b][1,4]diazepin-2-one, 5-[3-(4-oxo-7-pyrrol-1-yl-4,5-dihydro-3H-benzo[b][1,4]diazepin-2-yl)-phenyl]-oxazole-4-carboxylic acid ethyl ester, 4-[3-(4-hydroxymethyl-oxazol-2-yl)-phenyl]-8-pyrrol-1-yl-1,3-dihydro-benzo[b][1,4]diazepin-2-one, and 4-[3-(3-methyl-isoxazol-5-yl)-phenyl]-8-pyrrol-1-yl-1,3-dihydro-benzo[b][1,4]diazepin-2-one.

14. A compound according to claim 1, wherein $R^1$ is substituted pyrrol-1-yl.

15. A compound according to claim 14, wherein $R^2$ is hydrogen or lower alkoxy.

16. A compound according to claim 15, wherein the compound is selected from the group consisting of 4-(2-chloro-phenyl)-1-[2-(3-cyano-phenyl)-4-oxo-4,5-dihydro-3H-benzo[b][1,4]diazepin-7-yl]-1H-pyrrole-3-carbonitrile, 3-[4-oxo-7-(3-phenyl-pyrrol-1-yl)-4,5-dihydro-3H-benzo[b][1,4]diazepin-2-yl]-benzonitrile, and 3-[7-(2-tert.-butyl-pyrrol-1-yl)-8-methoxy-4-oxo-4,5-dihydro-3H-benzo[b][1,4]diazepin-2-yl]-benzonitrile.

17. A compound according to claim 1, wherein $R^1$ is cyano.

18. A compound according to claim 1, wherein $R^2$ is morpholine or thiomorpholine.

19. A compound according to claim 1, wherein $R^3$ is cyano or substituted or unsubstituted five-membered aromatic heterocycle.

20. The compound, 4-(4-Oxo-7-pyrrol-1-yl-4,5-dihydro-3H-benzo[b][1,4]diazepin-2-yl)-pyridine-2-carbonitrile.

21. A pharmaceutical composition comprising at least one compound of formula 1 according to claim 1, or a pharmaceutically acceptable salt thereof, and a pharmaceutically acceptable excipient.

22. A process for preparing a compound of formula I according to claim 1 comprising a) reacting a compound of formula II

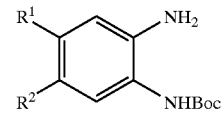

II with a compound of formula IV

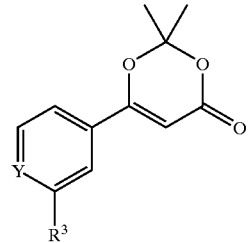

IV wherein R is lower alkyl, ethyl or tert.-butyl, thereby forming a compound of formula III

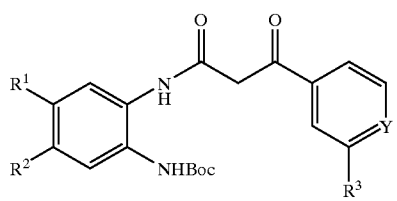 III then deprotecting the amino group and cyclizing, forming a compound of formula I

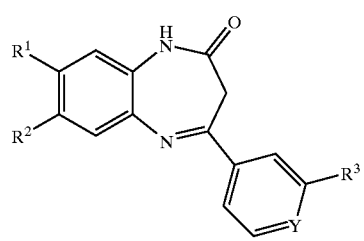 I wherein $R^1$, $R^2$, $R^3$ and Y are as described above.

23. A process for preparing a compound of formula I according to claim 1 comprising reacting a compound of formula II

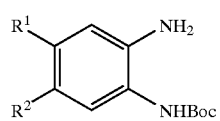 II with a compound of formula IVa

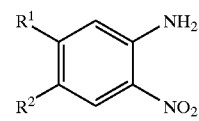 IVa wherein R is lower alkyl, ethyl or tert.-butyl, thereby forming a compound of formula III

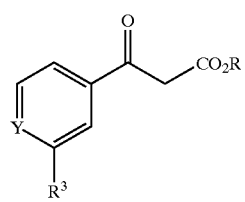 III deprotecting the amino group, then cyclizing, forming a compound of formula I

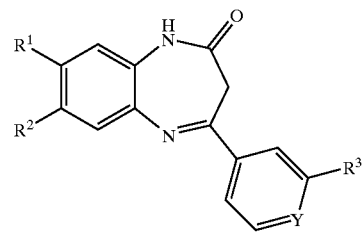 I wherein $R^1$, $R^2$, $R^3$ and Y are as described above.

24. A process for preparing a compound of formula I according to claim 1 comprising reacting a compound of formula VI

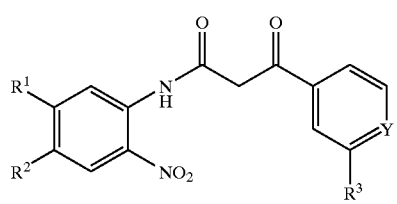 VI with a compound of formula IV

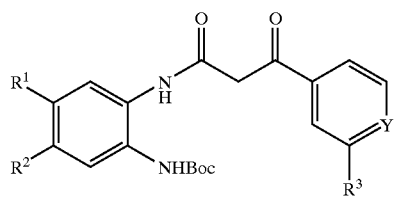 IV forming a compound of formula V

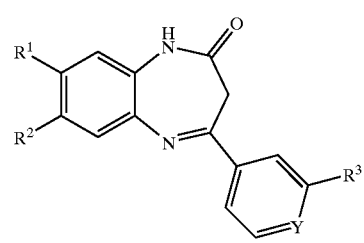 V then reducing the nitro group of formula V and cyclizing, forming a compound of formula I

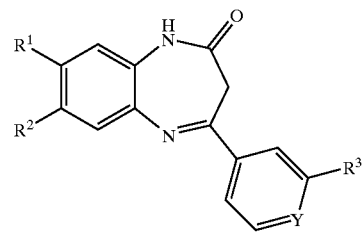 I wherein $R^1$, $R^2$, $R^3$ and Y are as described above.

* * * * *